United States Patent
Alexandrov et al.

(10) Patent No.: US 11,060,153 B2
(45) Date of Patent: Jul. 13, 2021

(54) FLUORESCENCE AMPLIFICATION METHOD FOR FORWARD GENETIC DISCOVERY OF FACTORS IN HUMAN MRNA DEGRADATION

(71) Applicant: Yale University, New Haven, CT (US)

(72) Inventors: Andrei Alexandrov, Woodbridge, CT (US); Joan Steitz, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/849,779

(22) Filed: Dec. 21, 2017

(65) Prior Publication Data

US 2018/0179601 A1 Jun. 28, 2018

Related U.S. Application Data

(60) Provisional application No. 62/438,205, filed on Dec. 22, 2016.

(51) Int. Cl.

| | |
|---|---|
| *C12Q 1/68* | (2018.01) |
| *C12Q 1/6897* | (2018.01) |
| *C12N 15/10* | (2006.01) |
| *C12N 9/50* | (2006.01) |
| *C12N 7/00* | (2006.01) |
| *C12Q 1/6883* | (2018.01) |

(52) U.S. Cl.
CPC ............. *C12Q 1/6897* (2013.01); *C12N 7/00* (2013.01); *C12N 9/506* (2013.01); *C12N 15/1048* (2013.01); *C12N 15/1058* (2013.01); *C12N 15/1086* (2013.01); *C12Q 1/6883* (2013.01); *C12Y 304/22044* (2013.01); *C07K 2319/60* (2013.01); *C07K 2319/95* (2013.01); *C12N 2740/15051* (2013.01); *C12N 2740/16043* (2013.01); *C12N 2770/34022* (2013.01)

(58) Field of Classification Search
CPC ...... C12Q 1/6897; C12Q 1/6883; C12N 7/00; C12N 9/506; C12N 15/1048; C12N 15/1058; C12N 15/1086; C12N 2740/15051; C12N 2740/16043; C12N 2770/34022; C12Y 304/22044; C07K 2319/60; C07K 2319/95

See application file for complete search history.

(56) References Cited

U.S. PATENT DOCUMENTS

2003/0086942 A1* 5/2003 Petersen ............... C07K 14/005
424/186.1
2006/0064770 A1* 3/2006 Frendewey ........ A01K 67/0275
800/18

FOREIGN PATENT DOCUMENTS

WO WO-2010034870 A1 * 4/2010 ............... C07K 7/06

OTHER PUBLICATIONS

Harbaugh et al (Proceedings of SPIE, 2008, vol. 7040, pp. 1-9). (Year: 2008).*
Waugh (Protein Experimental Purification, 2011, vol. 80, pp. 1-26). (Year: 2011).*
Rechsteiner and Rogers (TIBS, 1996, vol. 21, pp. 267-271).*
Park et al. Virology, 1995, vol. 210, pp. 194-201.*
Gurskaya et al. "Analysis of Nonsense-Mediated mRNA Decay at the Single-Cell Level Using Two Fluorescent Proteins" Methods Enzymol 2016, 572:291-314.
Pereverzev et al. "Method for quantitative analysis of nonsense-mediated mRNA decay at the single cell level" Sci Rep 2015, 5:7729.
Paillusson et al. "A GFP-based reporter system to monitor nonsense-mediated mRNA decay" Nucleic Acids Res 2005, 33:e54.
Nickless et al. "Intracellular calcium regulates nonsense-mediated mRNA decay" Nat Med 2014, 20:961-966.
Kurosaki et al. "Nonsense-mediated mRNA decay in humans at a glance" J Cell Sci 2016, 129:461-467.
Gardner "Hypoxic Inhibition of Nonsense-Mediated RNA Decay Regulates Gene Expression and the Integrated Stress Response" Mol Cell Biol 2008, 28:3729-3741.
Martin et al. "Hypoxic activation of ATR and the suppression of the initiation of DNA replication through cdc6 degradation" J Biol Chem 2010, 285:31944-31953.
Bachmair et al. "In vivo half-life of a protein is a function of its amino-terminal residue" Science 1986, 234:179-186.
Shalem et al. "Genome-Scale CRISPR-Cas9 Knockout Screening in Human Cells" Science 2014, 343:84-87.
Moffat et al. "A lentiviral RNAi library for human and mouse genes applied to an arrayed viral high-content screen" Cell 2006, 124:1283-1298.
Landrette et al. "piggyBac Transposon Somatic Mutagenesis with an Activated Reporter and Tracker (PB-SMART) for Genetic Screens in Mice" PLoS One 2011, 6:e26650.
Tuerk et al. "Systematic evolution of ligands by exponential enrichment: RNA ligands to bacteriophage T4 DNA polymerase" Science 1990, 249:505-510.
Raab et al. "Human tRNA genes function as chromatin insulators" EMBO J., 2012, 31:330-350.

(Continued)

*Primary Examiner* — Catherine S Hibbert
(74) *Attorney, Agent, or Firm* — Riverside Law LLP

(57) ABSTRACT

The present invention provides systems and methods for performing forward genetic screens in cells and methods of treating disease through inhibiting targets identified in a forward genetic screen as involved in a pathway associated with the disease. The invention involves the use of multiple tandem fluorescent reporter molecules separated by cleavage sites under the control of a single promoter to enhance the fluorescent readout from a cell screen.

9 Claims, 7 Drawing Sheets

Specification includes a Sequence Listing.

(56) References Cited

OTHER PUBLICATIONS

Lee et al. "Protecting a transgene expression from the HAC-based vector by different chromatin insulators" Cell. Mol. Life Sci., 2013, 70:3723-3737.

Zhang et al. "Intron function in the nonsense-mediated decay of beta-globin mRNA: Indications that pre-mRNA splicing in the nucleus can influence mRNA translation in the cytoplasm" RNA, 1998, 4:801-815.

* cited by examiner

SEQUENCE LISTING

<160> NUMBER OF SEQ ID NOS: 33

<210> SEQ ID NO 1
<211> LENGTH: 11503
<212> TYPE: DNA
<213> ORGANISM: Artificial Sequence
<220> FEATURE:
<223> OTHER INFORMATION: AVA2590, Launchpad, PuromycinR vector sequence

<400> SEQUENCE: 1

```
gtggcccgag agctgcatcc ggagtatcta gatggagttc cgcgttacat aacttacggt      60
aaatggcccg cctggctgac cgcccaacga cccccgccca ttgacgtcaa taatgactga     120
tgttcccata gtaacgccaa tagggacttt ccattgacgc taatgggagt ttgttttggc     180
accaaaatca acgggacttt ccaaaatgtc gtaataaccc cgccccgttg acgcaaatgg     240
gcggtaggcg tgtactctag aaggtctata taagcagagc tcgtttagtg aaccgtttat     300
actacttatc tggtctctct ggttagacca gatctgagcc tgggagctct ctggctaact     360
agggaaccca ctgcttaagc ctcaataaag cttgccttga gtgctcaaag tagtgtgtgc     420
ccgtctgttg tgtgactctg gtaactagag atccctcaga ccctttagt cagtgtggaa      480 aatctctagc agtggcgccc gaacagggac ttgaaagcga agtaaagcc agaggagatc      540 tctcgacgca ggactcggct tgctgaagcg cgcacggcaa gaggcgaggg gcggcgactg     600
gtgagtacgc caaaaatttt gactagcgga ggctagaagg agagagatgg gtgcgagagc     660
gtcggtatta agcgggggag aattagataa atgggaaaaa attcggttaa ggccaggggg     720
aaagaaacaa tataaactaa aacatatagt atgggcaagc agggagctag aacgattcgc     780
agttaatcct ggccttttag agacatcaga aggctgtaga caaatactgg gacagctaca     840
accatcccct cagacaggat cagaagaact tagatcatta tataatacaa tagcagtcct     900
ctattgtgtg catcaaagga tagatgtaaa agacaccaag gaagccttag ataagataga     960
ggaagagcaa aacaaaagta agaaaaaggc acagcaagca gcagctgaca caggaaacaa    1020
cagccaggtc agccaaaatt accctatagt gcagaacctc caggggcaaa tggtacatca    1080
ggccatatca cctagaactt taaatgcatg gtaaaagta gtagaagaga aggctttcag    1140
cccagaagta atacccatgt tttcagcatt atcagaagga gccaccccac aagatttaaa    1200
taccatgcta aacacagtgg ggggacatca agcagccatg caaatgttaa aagagaccat    1260
caatgaggaa gctgcagaat gggatagatt gcatccagtg catgcagggc ctattgcacc    1320
aggccagatg agagaaccaa ggggaagtga catagcagga actactagca aattaagaga    1380
acaatttgga aataataaaa caataatctt aagcaatcc tcaggagggg acccagaaat    1440
tgtaacgcac agttttaatt gtggagggga attttctac tgtaattcaa cacaactgtt      1500
taatagtact tggtttaata gtacttggag tactgaaggg tcaaataaca ctgaaggaag    1560
tgacacaatc acactcccat gcagaataaa acaatttata aacatgtggc aggaagtagg    1620
aaaagcaatg tatgcccctc ccatcagtgg acaaattaga tgttcatcaa atattactgg    1680
gctgctatta acaagagatg gtggtaataa caacaatggg tccgagatct tcagacctgg    1740
aggaggcgat atgagggaca attggagaag tgaattatat aaatataaag tagtaaaaat    1800
tgaaccatta ggagtagcac ccaccaaggc aaagagaaga gtggtgcaga gagaaaaaag    1860
agcagtggga ataggagctt tgttccttgg gttcttggga gcagcaggaa gcactatggg    1920
cgcacggtca atgacgctga cggtacaggc cagacaatta ttgtctgata tagtgcagca    1980
gcagaacaat ttgctgaggg ctattgaggc gcaacagcat ctgttgcaac tcacagtctg    2040
```

```
gggcatcaaa cagctccagg caagaatcct ggctgtggaa agatacctaa aggatcaaca    2100
gctcctgggg atttggggtt gctctggaaa actcatttgc accactgctg tgccttggaa    2160
tgctagttgg agtaataaat ctctggaaca gatttggaat aacatgacct ggatggagtg    2220
ggacagagaa attaacaatt acacaagctt aatacactcc ttaattgaag aatcgcaaaa    2280
ccagcaagaa aagaatgaac aagaattatt ggaattagat aaatgggctt gcggccggaa    2340
ttcacaaatg gcagtattca tccacaattt taaaagaaaa gggggattg ggggtacag     2400 tgcaggggaa agaatagtag acataatagc aacagacata caaactaaag aattacaaaa    2460
acaaattaca aaaattcaaa attttcgggt ttattacagg gacagcagag atccactttg    2520
ggcggccgcg cgaggcagct gtggaatgtg tgtcagttag ggtgtggaaa gtccccaggc    2580
tccccagcag gcagaagtat gcaaagcatg catctcaatt agtcagcaac caggtgtgga    2640
aagtccccag gctccccagc aggcagaagt atgcaaagca tgcatctcaa ttagtcagca    2700
accatagtcc cgcccctaac tccgcccatc ccgcccctaa ctccgcccag ttccgcccat    2760
tctccgcccc atggctgact aattttttttt atttatgcag aggccgaggc cgcctcggcc    2820
tctgagctat tccagaagta gtgaggaggc ttttttggag gctaccatgg agaagttcct    2880
attccgaagt tcctattctc tagaaagtat aggaacttca gcttggtcg accctcttaa     2940 gtaccacatt tgtagaggtt ttacttgctt taaaaaacct cccacacctc ccctgaacc     3000 tgaaacataa aatgaatgca attgttgttg ttaacttgtt tattgcagct tataatggtt    3060
acaaataaag caatagcatc acaaatttca caaataaagc attttttttca ctgcattcta   3120 gttgtggttt gtccaaactc atcgagctcg acttacttgt acagctcgtc catgccgaga    3180
gtgatcccgg cggcggtcac gaactccagc aggaccatgt gatcgcgctt ctcgttgggg    3240
tctttgctca gggcggactg ggtgctcagg tagtggttgt cgggcagcag cacggggccg    3300
tcgccgatgg gggtgttctg ctggtagtgg tcggcgagct gcacgctgcc gtcctcgatg    3360
ttgtggcgga tcttgaagtt caccttgatg ccgttcttct gcttgtcggc catgatatag    3420
acgttgtggc tgttgtagtt gtactccagc ttgtgcccca ggatgttgcc gtcctccttg    3480
aagtcgatgc ccttcagctc gatgcggttc accagggtgt cgccctcgaa cttcacctcg    3540
gcgcgggtct tgtagttgcc gtcgtccttg aagaagatgg tgcgctcctg gacgtagcct    3600
tcgggcatgg cggacttgaa gaagtcgtgc tgcttcatgt ggtcggggta gcggctgaag    3660
cactgcacgc cgtaggtcag ggtggtcacg agggtgggcc agggcacggg cagcttgccg    3720
gtggtgcaga tgaacttcag ggtcagcttg ccgtaggtgg catcgccctc gccctcgccg    3780
gacacgctga acttgtggcc gtttacgtcg ccgtccagct cgaccaggat gggcaccacc    3840
ccggtgaaca gctcctcgcc cttgctcacc atggtggact agttctagag cggaaacgct    3900
agagttttca cgacacctga aatggaagaa aaaaactttg aaccactgtc tgaggcttga    3960
gaatgaacca agatccaaac tcaaaaaggg caaattccaa ggagaattac atcaagtgcc    4020
aagctggcct aacttcagtc tccacccact cagtgtgggg aaactccatc gcataaaacc    4080 cctccccca acctaaagac gacgtactcc aaaagctcga gaactaatcg aggtgcctgg     4140
acggcgcccg gtactccgtg gagtcacatg aagcgacgc tgaggacgga aaggcccttt      4200
tcctttgtgt gggtgactca cccgcccgct ctcccgagcg ccgcgtcctc cattttgagc    4260
tccctgcagc agggccggga agcggccatc tttccgctca cgcaactggt gccgaccggg    4320
ccagcctgtt gccgcccagg gcggggcgat acacggcggc gcgaggccag gcaccagagc    4380
```

```
aggccggcca gcttgagact accccccgtcc gattctcggt ggccgcgctc gcaggccccg    4440
cctcgccgaa catgtgcgct gggacgcacg ggcccgtcg ccgccgcgg ccccaaaaac       4500
cgaaatacca gtgtgcagat cttggcccgc atttacaaga ctatcttgcc agaaaaaaag    4560
cgtcgcagca ggtcatcaaa aattttaaat ggctagagac ttatcgaaag cagcgagaca    4620
ggcgcgaagg tgccaccaga ttcgcacgcg gcggcccag cgcccaggcc aggcctcaac     4680
tcaagcacga ggcgaagggg ctccttaagc gcaaggcctc gaactctccc acccacttcc    4740
aacccgaagc tcgggatcaa gaatcacgta ctgcagccag gggcgtggaa gtaattcaag    4800
gcacgcaagg gccataaccc gtaaagaggc caggcccgcg ggaaccacac acggcactta    4860
cctgtgttct ggcggcaaac ccgttgcgaa aaagaacgtt cacggcgact actgcactta    4920
tatacggttc tcccccaccc tcgggaaaaa ggcggagcca gtacacgaca tcactttccc    4980
agtttacccc gcgccacttt ctctaggcac cggttcaatt gccgacccct ccccccaact    5040
tctcggggac tgtgggcgat gtgcgctctg cccactgacg ggcaccggag cctcacgcat    5100
gctcttctcc acctcagtga tgacgagagc gggcgggtga gggggcggga acgcagcgat    5160
ctctggggttc tacgttagtg ggagtttaac gacggtccct gggattcccc aaggcagggg    5220
cgagtccttt tgtatgaatt actctcagct ccggtcgggg cggttggggg gggtggtga     5280
cggggaggcc gcctggaagg gacgtgcaga atcttccctc taccattgct ggcttagctc    5340
caaagcttat cgatgataag ctgtcaaaca tgagaattgc tagcaattct accgggtagg    5400
ggaggcgctt tcccaaggc agtctggagc atgcgcttta gcagcccgc tgggcacttg      5460
gcgctacaca agtggcctct ggcctcgcac acattccaca tccatcggta ggcgccaacc    5520
ggctccgttc tttggtggcc ccttcgcgcc accttctact cctcccctag tcaggaagtt    5580
ccccccccgcc ccgcagctcg cgtcgtgcag gacgtgacaa atggaagtag cacgtctcac   5640
tagtctcgtg cagatggaca gcaccgctga gcaatggaag cgggtaggcc tttggggcag    5700
cggccaatag cagctttgct ccttcgcttt ctgggctcag aggctgggaa ggggtgggtc    5760
cgggggcggg ctcaggggcg ggctcagggg cggggcgggc gcccgaaggt cctccggagg    5820
cccggcattc tgcacgcttc aaaagcgcac gtctgccgcg ctgttctcct cttcctcatc    5880
tccgggcctt tcgacctgca gcccaagctt accatgaccg agtacaagcc cacggtgcgc    5940
ctcgccaccc gcgacgacgt ccccaggccc gtacgcaccc tcgccgccgc gttcgccgac    6000
taccccgcca cgcgccacac cgtcgatccg gaccgccaca tcgagcgggt caccgagctg    6060
caagaactct tcctcacgcg cgtcgggctc gacatcggca aggtgtgggt cgcggacgac    6120
ggcgccgcgg tggcggtctg gaccacgccg gagagcgtcg aagcggggc ggtgttcgcc     6180
gagatcggcc cgcgcatggc cgagttgagc ggttccggc tggccgcgca gcaacagatg      6240
gaaggcctcc tggcgccgca ccggcccaag gagcccgcgt ggttcctggc caccgtcggc    6300
gtctcgcccg accaccaggg caagggtctg ggcagcgccg tcgtgctccc cggagtggag    6360
gcggccgagc gcgccggggt gcccgccttc ctggagacct ccgcgcccg caacctcccc    6420
ttctacgagc ggctcggctt caccgtcacc gccgacgtcg aggtgcccga aggaccgcgc    6480
acctggtgca tgaccgcaa gcccggtgcc tgaggatccg aagttcctat tccgaagttc     6540
ctattctcta gaaagtatag gaacttcaga tccgcggact agtgaattcc agctgagcgc    6600
cggtcgctac cattaccagt tggtctggtg tcaaaaataa taataaccgg gcaggggga     6660
tctcgactct agaagcttgg tacctttaag accaatgact tacaaggcag ctgtagatct    6720
tagccacttt ttaaaagaaa aggggggact ggaagggcta attcactccc agggtctctc    6780
```

-continued

```
tggttagacc agatctgagc ctgggagctc tctggctaac tagggaaccc actgcttaag    6840
cctcataaag ctcgactgtg ccttctagtt gccagccatc tgttgtttgc ccctcccccg    6900
tgccttcctt gaccctggaa ggtgccactc ccactgtcct ttcctaataa aatgaggaaa    6960
ttgcatcgca ttgtctgagt aggtgtcatt ctattctggg gggtggggtg gggcaggaca    7020
gcaaggggga ggattgggaa gacaatagca ggcatgctgg ggatgcggtg ggctctatgg    7080
cttctgaggc ggaaagaacc agctggggct ctagggggta tccccacgcg ccctgtagcg    7140
gcgcattaag cgcggcgggt gtggtggtta cgcgcagcgt gaccgctaca cttgccagcg    7200
ccctagcgcc cgctcctttc gctttcttcc cttcctttct cgccacgttc gccggctgtg    7260
cgggagaacg gagttctatt atgactcaaa tcagtctccc caagcattcg gggatcagag    7320
tttttaagga taacttagtg tgtagggggc cagtgagttg gagatgaaag cgtagggagt    7380
cgaaggtgtc cttttgcgcc gagtcagttc ctgggtgggg ccacaagat cggatgagcc     7440
agtttatcaa tccgggggtg ccagctgatc catggagtgc agggtctgca aaatatctca    7500
agcactgatt gatcttaggt tttacaatag tgatgttacc ccaggaacaa tttggggaag    7560
gtcagaatct tgtagcctgt agctgcatga ctcctaaacc ataatttctt ttttgttttt    7620
tttttttat ttttgagaca gggtctcact ctgtcaccta ggctggagtg cagtggtgca    7680
atcacagctc actgcagcct caacgtcgta agctcaagcg atcctcccac ctcagcctgc    7740
ctggtagctg agactacaag cgacgcccca gttaattttt gtattttgg tagaggcagc     7800
gttttgccgt gtggccctgg ctggtctcga actcctgggc tcaagtgatc cagcctcagc    7860
ctcccaaagt gctgggacaa ccggggccag tcactgcacc tggccctaaa ccataatttc    7920
taatcttttg gctaatttgt tagtcctaca aaggcagtct agtccccagg caaaaagggg    7980
gtttgtttcg ggaagggct gttactgtct ttgtttcaaa ctataaacta agttcctcct     8040
aaacttagtt cggcctacac ccaggaatga acaaggagag cttggaggtt agaagcacga    8100
tggaattggt taggtcagat ctctttcact gtctgagtta aattttgca atggtggttc     8160
aaagactgcc cgcttctgac accagtcgct gcattaatga atcggccaac gcgcggggag    8220
aggcggtttg cgtattggcg ctcttccgct tcctcgctca ctgactcgct gcgctcggtc    8280
gttcggctgc ggcgagcggt atcagctcac tcaaaggcgg taatacggtt atccacagaa    8340
tcaggggata cgcaggaaa gaacatgtga gcaaaaggcc agcaaaaggc caggaaccgt     8400
aaaaaggccg cgttgctggc gttttttcat aggctccgcc cccctgacga gcatcacaaa    8460
aatcgacgct caagtcagag gtggcgaaac ccgacaggac tataaagata ccaggcgttt    8520
ccccctggaa gctccctcgt gcgctctcct gttccgaccc tgccgcttac cggatacctg    8580
tccgcctttc tcccttcggg aagcgtggcg ctttctcaat gctcacgctg taggtatctc    8640
agttcggtgt aggtcgttcg ctccaagctg ggctgtgtgc acgaaccccc cgttcagccc    8700
gaccgctgcg ccttatccgg taactatcgt cttgagtcca acccggtaag acacgactta    8760
tcgccactgg cagcagccac tggtaacagg attagcagag cgaggtatgt aggcggtgct    8820
acagagttct tgaagtggtg gcctaactac ggctacacta aggacagt atttggtatc      8880
tgcgctctgc tgaagccagt taccttcgga aaaagagttg gtagctcttg atccggcaaa    8940
caaaccaccg ctggtagcgg tggtttttt gtttgcaagc agcagattac gcgcagaaaa     9000
aaaggatctc aagaagatcc tttgatcttt tctacgggt ctgacgctca gtggaacgaa     9060
aactcacgtt aagggatttt ggtcatgaga ttatcaaaaa ggatcttcac ctagatcctt    9120
```

```
ttaaattaaa aatgaagttt taaatcaatc taaagtatat atgagtaaac ttggtctgac      9180
agttaccaat gcttaatcag tgaggcacct atctcagcga tctgtctatt tcgttcatcc      9240
atagttgcct gactccccgt cgtgtagata actacgatac gggagggctt accatctggc      9300
cccagtgctg caatgatacc gcgagaccca cgctcaccgg ctccagattt atcagcaata      9360
aaccagccag ccggaagggc cgagcgcaga agtggtcctg caactttatc cgcctccatc      9420
cagtctatta attgttgccg ggaagctaga gtaagtagtt cgccagttaa tagtttgcgc      9480
aacgttgttg ccattgctac aggcatcgtg gtgtcacgct cgtcgtttgg tatggcttca      9540
ttcagctccg gttcccaacg atcaaggcga gttacatgat cccccatgtt gtgcaaaaaa      9600
gcggttagct ccttcggtcc tccgatcgtt gtcagaagta agttggccgc agtgttatca      9660
ctcatggtta tggcagcact gcataattct cttactgtca tgccatccgt aagatgcttt      9720
tctgtgactg gtgagtactc aaccaagtca ttctgagaat agtgtatgcg gcgaccgagt      9780
tgctcttgcc cggcgtcaat acgggataat accgcgccac atagcagaac tttaaaagtg      9840
ctcatcattg gaaaacgttc ttcggggcga aaactctcaa ggatcttacc gctgttgaga      9900
tccagttcga tgtaacccac tcgtgcaccc aactgatctt cagcatcttt tactttcacc      9960
agcgtttctg ggtgagcaaa aacaggaagg caaaatgccg caaaaaaggg aataaggggcg     10020 acacggaaat gttgaatact catactcttc cttttttcaat attattgaag catttatcag     10080
ggttattgtc tcatgagcgg atacatattt gaatgtattt agaaaaataa acaaataggg     10140
gttccgcgca catttccccg aaaagtgcca cctgacgtct aagaaaccat tattatcatg     10200
acattaacct ataaaaatag gcgtatcacg aggcccttc  gtcttcaaga actgcctcgc     10260
gcgtttcggt gatgacggtg aaaacctctg acacatgcag ctcccggaga cggtcacagc     10320
ttgtctgtaa gcggatgccg ggagcagaca agcccgtcag ggcgcgtcag cgggtgttgg     10380
cgggtgtcgg ggcgcagcca tgacccagtc acgtagcgat agcggagtgt actggcttaa     10440
ctatgcggca tcagagcaga ttgtactgag agtgcaccat atgcggtgtg aaataccgca     10500
cagatgcgta aggagaaaat accgcatcag gcgccattcg ccattcaggc tgcgcaactg     10560
ttgggaaggg cgatcggtgc gggcctcttc gctattacgc cagcgcgggg aggcagagat     10620
tgcagtaagc tgagatcgca gcactgcact ccagcctggg cgacagagta agactctgtc     10680
tcaaaaataa aataaataaa tcaatcagat attccaatct tttccttat ttatttattt      10740 attttctatt ttggaaacac agtccttcct tattccagaa ttacacatat attctatttt     10800
tctttatatg ctccagtttt ttttagacct tcacctgaaa tgtgtgtata caaaatctag     10860
gccagtccag cagagcctaa aggtaaaaaa taaaataata aaaataaat aaaatctagc      10920 tcactccttc acatcaaaat ggagatacag ctgttagcat taaataccaa ataacccatc     10980
ttgtcctcaa taatttttaag cgcctctctc caccacatct aactcctgtc aaaggcatgt     11040
gccccttccg ggcgctctgc tgtgctgcca accaactggc atgtggactc tgcagggtcc     11100
ctaactgcca agccccacag tgtgccctga ggctgcccct tccttctagc ggctgccccc     11160
actcggcttt gctttcccta gtttcagtta cttgcgttca gccaaggtct gaaactaggt     11220
gcgcacagag cggtaagact gcgagagaaa gagaccagct ttacagggg  tttatcacag     11280 tgcaccctga cagtcgtcag cctcacaggg ggtttatcac attgcaccct gacagtcgtc     11340
agcctcacag ggggtttatc acagtgcacc cttacaatca ttccatttga ttcacaattt     11400
ttttagtctc tactgtgcct aacttgtaag ttaaatttga tcagaggtgt gttcccagag     11460
gggaaaacag tatatacagg gttcagtact atcgcatttc agg                        11503
```

<210> SEQ ID NO 2
<211> LENGTH: 15294
<212> TYPE: DNA
<213> ORGANISM: Artificial Sequence
<220> FEATURE:
<223> OTHER INFORMATION: AVA2515[RFP(PTC-), HygromycinR] vector sequence

<400> SEQUENCE: 2

```
acttcatttt taatttaaaa ggatctaggt gaagatcctt tttgataatc tcatgaccaa      60
aatcccttaa cgtgagtttt cgttccactg agcgtcagac cccgtagaaa agatcaaagg     120
atcttcttga tccttttttt ttctgcgcgt aatctgctgc ttgcaaacaa aaaaaccacc     180
gctaccagcg gtggtttgtt tgccggatca agagctacca actctttttc cgaaggtaac     240
tggcttcagc agagcgcaga taccaaatac tgtccttcta gtgtagccgt agttaggcca     300
ccacttcaag aactctgtag caccgcctac atacctcgct ctgctaatcc tgttaccagt     360
ggctgctgcc agtggcgata agtcgtgtct taccgggttg gactcaagac gatagttacc     420
ggataaggcg cagcggtcgg gctgaacggg gggttcgtgc acacagccca gcttggagcg     480
aacgacctac accgaactga gatacctaca gcgtgagcta tgagaaagcg ccacgcttcc     540
cgaagggaga aaggcggaca ggtatccggt aagcggcagg gtcggaacag gagagcgcac     600
gagggagctt ccagggggaa acgcctggta tctttatagt cctgtcgggt ttcgccacct     660
ctgacttgag cgtcgatttt tgtgatgctc gtcaggggg cggagcctat ggaaaaacgc     720
cagcaacgcg gccttttttac ggttcctggc cttttgctgg ccttttgctc acatgttctt     780
tcctgcgtta tcccctgatt ctgtggataa ccgtattacc gcctttgagt gagctgatac     840
cgctcgccgc agccgaacga ccgagcgcag cgagtcagtg agcgaggaag cggaagagcg     900
cccaatacgc aaaccgcctc tccccgcgcg ttggccgatt cattaatgca gctggcacga     960
caggtttccc gactggaaag cgggcagtga gcgcaacgca attaatgtga gttagctcac    1020
tcattaggca ccccaggcac gcgaagcgtt gttggtttgt agtgcccggt ttcgaaccgg    1080
ggacctttcg cgtgttaggc gaacgtgata accactacac tacgaaaacc aacggtgcta    1140
gacgcgtatt gtctattctg actcggatcc gtacgaattc tcatgtttga cagcttatca    1200
tcgattagct ttggagctaa gccagcaatg gtagagggaa gattctgcac gtcccttcca    1260
ggcggcctcc ccgtcaccac ccccccaac ccgcccgac cggagctgag agtaattcat    1320
acaaaaggac tcgcccctgc cttggggaat cccagggacc gtcgttaaac tcccactaac    1380
gtagaaccca gagatcgctg cgttcccgcc cctcacccg cccgctctcg tcatcactga    1440
ggtggagaag agcatgcgtg aggctccggt gcccgtcagt gggcagagcg cacatcgccc    1500
acagtccccg agaagttggg gggaggggtc ggcaattgaa ccggtgccta gagaaagtgg    1560
cgcggggtaa actgggaaag tgatgtcgtg tactggctcc gcctttttcc cgagggtggg    1620
ggagaaccgt atataagtgc agtagtcgcc gtgaacgttc ttttttcgcaa cgggtttgcc    1680
gccagaacac aggtaagtgc cgtgtgtggt tcccgcgggc ctggcctctt tacgggttat    1740
ggcccttgcg tgccttgaat tacttccacg cccctggctg cagtacgtga ttcttgatcc    1800
cgagcttcgg gttggaagtg ggtgggagag ttcgaggcct tgcgcttaag gagccccttc    1860
gcctcgtgct tgagttgagg cctggctgg gcgctgggc cgccgcgtgc gaatctggtg    1920
gcaccttcgc gcctgtctcg ctgctttcga taagtctcta gccatttaaa attttttgatg    1980
acctgctgcg acgcttttttt tctggcaaga tagtcttgta aatgcgggcc aagatctgca    2040
```

```
cactggtatt tcggttttg gggccgcggg cggcgacggg gcccgtgcgt cccagcgcac    2100
atgttcggcg aggcgggcc tgcgagcgcg gccaccgaga atcggacggg ggtagtctca    2160
agctggccgg cctgctctgg tgcctggcct cgcgccgccg tgtatcgccc cgccctgggc    2220
ggcaacaggc tggcccggtc ggcaccagtt gcgtgagcgg aaagatggcc gcttcccggc    2280
cctgctgcag ggagctcaaa atggaggacg cggcgctcgg gagagcgggc gggtgagtca    2340
cccacacaaa ggaaaagggc ctttccgtcc tcagccgtcg cttcatgtga ctccacggag    2400
taccgggcgc cgtccaggca cctcgattag ttctcgagct tttggagtac gtcgtcttta    2460
ggttgggggg aggggtttta tgcgatggag tttccccaca ctgagtgggt ggagactgaa    2520
gttaggccag cttggcactt gatgtaattc tccttggaat ttgccctttt tgagtttgga    2580
tcttggttca ttctcaagcc tcagacagtg gttcaaagtt ttttcttcc atttcaggtg    2640 tcgtgaaaac tctagcgttt ccgctctaga actagtccag ctagcgctac cggtcgccac    2700
catggtgagc aagggcgagg aggtcatcaa agagttcatg cgcttcaagg tgcgcatgga    2760
gggctccatg aacggcacg agttcgagat cgagggcgag ggcgagggcc gccctacga    2820 gggcacccag accgccaagc tgaaggtgac caagggcggc cccctgccct tcgcctggga    2880
catcctgtcc ccccagttca tgtacggctc caaggcgtac gtgaagcacc ccgccgacat    2940
ccccgattac aagaagctgt ccttccccga gggcttcaag tgggagcgcg tgatgaactt    3000
cgaggacggc ggtctggtga ccgtgaccca ggactcctcc ctgcaggacg gcacgctgat    3060
ctacaaggtg aagatgcgcg gcaccaactt ccccccgac ggccccgtaa tgcagaagaa    3120
gaccatgggc tgggaggcct ccaccgagcg cctgtacccc cgcgacgcg tgctgaaggg    3180 cgagatccac caggccctga agctgaagga cggcggccac tacctggtgg agttcaagac    3240
catctacatg gccaagaagc ccgtgcaact gcccggctac tactacgtgg acaccaagct    3300
ggacatcacc tcccacaacg aggactacac catcgtggaa cagtacgagc gctccgaggg    3360
ccgccaccac ctgttcctgg ggcatggcac cggcagcacc ggcagcggca gctccggcac    3420
cgcctcctcc gaggacaaca acatggccgt catcaaagag ttcatgcgct tcaaggtgcg    3480
catggagggc tccatgaacg ccacgagtt cgagatcgag ggcgagggcg agggccgccc    3540
ctacgagggc acccagaccg ccaagctgaa ggtgaccaag ggcggccccc tgcccttcgc    3600
ctgggacatc ctgtccccccc agttcatgta cggctccaag gcgtacgtga agcaccccgc    3660
cgacatcccc gattacaaga agctgtcctt ccccgagggc ttcaagtggg agcgcgtgat    3720
gaacttcgag gacggcggtc tggtgaccgt gacccaggac tcctccctgc aggacggcac    3780
gctgatctac aaggtgaaga tgcgcggcac caacttcccc ccgacggcc ccgtaatgca    3840 gaagaagacc atgggctggg aggcctccac cgagcgcctg taccccgcg acggcgtgct    3900 gaagggcgag atccaccagg ccctgaagct gaaggacggc ggccactacc tggtggagtt    3960
caagaccatc tacatggcca agaagccgt gcaactgccc ggctactact acgtggacac    4020
caagctggac atcacctccc acaacgagga ctacaccatc gtggaacagt acgagcgctc    4080
cgagggccgc caccacctgt tcctgtacgg catggacgag ctgtacaagg tcactccgtg    4140
tgaaaacctg tacttccaag gtatggtgag caagggcgag gaggtcatca aagagttcat    4200
gcgcttcaag gtgcgcatgg agggctccat gaacggccac gagttcgaga tcgagggcga    4260
gggcgagggc cgcccctacg agggcaccca gaccgccaag ctgaaggtga ccaagggcgg    4320 cccccctgccc ttcgcctggg acatcctgtc ccccagttc atgtacggct ccaaggcgta    4380
cgtgaagcac cccgccgaca tccccgatta caagaagctg tccttccccg agggcttcaa    4440
```

```
gtgggagcgc gtgatgaact tcgaggacgg cggtctggtg accgtgaccc aggactcctc    4500
cctgcaggac ggcacgctga tctacaaggt gaagatgcgc ggcaccaact tccccccga     4560 cggcccgta atgcagaaga agaccatggg ctgggaggcc tccaccgagc gcctgtaccc     4620
ccgcgacggc gtgctgaagg gcgagatcca ccaggccctg aagctgaagg acggcggcca    4680
ctacctggtg gagttcaaga ccatctacat ggccaagaag cccgtgcaac tgcccggcta    4740
ctactacgtg gacaccaagc tggacatcac ctcccacaac gaggactaca ccatcgtgga    4800
acagtacgag cgctccgagg ccgccacca cctgttcctg gggcatggca ccggcagcac    4860
cggcagcggc agctccggca ccgcctcctc cgaggacaac aacatggccg tcatcaaaga    4920
gttcatgcgc ttcaaggtgc gcatggaggg ctccatgaac ggccacgagt tcgagatcga    4980
gggcgagggc gagggccgcc cctacgaggg cacccagacc gccaagctga aggtgaccaa    5040
gggcggcccc ctgcccttcg cctgggacat cctgtcccc cagttcatgt acggctccaa     5100
ggcgtacgtg aagcacccg ccgacatccc cgattacaag aagctgtcct tccccgaggg     5160
cttcaagtgg gagcgcgtga tgaacttcga ggacggcggt ctggtgaccg tgacccagga    5220
ctcctccctg caggacggca cgctgatcta caaggtgaag atgcgcggca ccaacttccc    5280
ccccgacggc cccgtaatgc agaagaagac catgggctgg gaggcctcca ccgagcgcct    5340 gtaccccgc gacggcgtgc tgaagggcga gatccaccag gccctgaagc tgaaggacgg    5400
cggccactac ctggtggagt tcaagaccat ctacatggcc aagaagcccg tgcaactgcc    5460
cggctactac tacgtggaca ccaagctgga catcacctcc cacaacgagg actacaccat    5520
cgtggaacag tacgagcgct ccgagggccg ccaccacctg ttcctgtacg gcatggacga    5580
gctgtacaag accactgcgt gcgaaaacct gtacttccaa ggtatggtga caagggcga    5640 ggaggtcatc aaagagttca tgcgcttcaa ggtgcgcatg gagggctcca tgaacggcca    5700
cgagttcgag atcgagggcg agggcgaggg ccgcccctac gagggcaccc agaccgccaa    5760
gctgaaggtg accaagggcg ccccctgcc cttcgcctgg gacatcctgt cccccagtt     5820 catgtacggc tccaaggcgt acgtgaagca ccccgccgac atccccgatt acaagaagct    5880
gtccttcccc gagggcttca gtgggagcg cgtgatgaac ttcgaggacg gcggtctggt     5940
gaccgtgacc caggactcct ccctgcagga cggcacgctg atctacaagg tgaagatgcg    6000
cggcaccaac ttccccccg acggccccgt aatgcagaag aagaccatgg gctgggaggc    6060
ctccaccgag cgcctgtacc ccgcgacgg cgtgctgaag ggcgagatcc accaggccct     6120
gaagctgaag gacggcggcc actacctggt ggagttcaag accatctaca tggccaagaa    6180
gcccgtgcaa ctgcccggct actactacgt ggacaccaag ctggacatca cctcccacaa    6240
cgaggactac accatcgtgg aacagtacga gcgctccgag ggccgccacc acctgttcct    6300
ggggcatggc accggcagca ccggcagcgg cagctccggc accgcctcct ccgaggacaa    6360
caacatggcc gtcatcaaag agttcatgcg cttcaaggtg cgcatggagg gctccatgaa    6420
cggccacgag ttcgagatcg agggcgaggg cgagggccgc ccctacgagg gcacccagac    6480
cgccaagctg aaggtgacca agggcggccc cctgcccttc gcctgggaca tcctgtcccc    6540
ccagttcatg tacggctcca aggcgtacgt gaagcacccc gccgacatcc ccgattacaa    6600
gaagctgtcc ttccccgagg gcttcaagtg ggagcgcgtg atgaacttcg aggacggcgg    6660
tctggtgacc gtgacccagg actcctccct gcaggacggc acgctgatct acaaggtgaa    6720
gatgcgcggc accaacttcc cccccgacgg ccccgtaatg cagaagaaga ccatgggctg    6780
```

```
ggaggcctcc accgagcgcc tgtaccccg cgacggcgtg ctgaagggcg agatccacca    6840
ggccctgaag ctgaaggacg gcggccacta cctggtggag ttcaagacca tctacatggc    6900
caagaagccc gtgcaactgc ccggctacta ctacgtggac accaagctgg acatcacctc    6960
ccacaacgag gactacacca tcgtggaaca gtacagcgc tccgagggcc gccaccacct    7020
gttcctgtac ggcatggacg agctgtacaa ggtcactacg tgtgaaaacc tgtacttcca    7080
aggtatggtg agcaagggcg aggaggtcat caaagagttc atgcgcttca aggtgcgcat    7140
ggagggctcc atgaacggcc acgagttcga gatcgagggc gagggcgagg ccgcccccta    7200
cgagggcacc cagaccgcca agctgaaggt gaccaagggc ggcccctgc ccttcgcctg    7260 ggacatcctg tcccccagt tcatgtacgg ctccaaggcg tacgtgaagc accccgccga    7320
catccccgat tacaagaagc tgtccttccc cgagggcttc aagtgggagc gcgtgatgaa    7380
cttcgaggac ggcggtctgg tgaccgtgac ccaggactcc tccctgcagg acggcacgct    7440
gatctacaag gtgaagatgc gcggcaccaa cttccccccc gacggccccg taatgcagaa    7500
gaagaccatg ggctgggagg cctccaccga gcgcctgtac cccgcgacg gcgtgctgaa    7560 gggcgagatc caccaggccc tgaagctgaa ggacggcggc cactacctgg tggagttcaa    7620
gaccatctac atggccaaga gcccgtgca actgccggc tactactacg tggacaccaa    7680
gctggacatc acctcccaca acgaggacta caccatcgtg aacagtacg agcgctccga    7740 gggccgccac cacctgttcc tggggcatgg caccggcagc accggcagcg cagctccgg    7800 caccgcctcc tccgaggaca caacatggc cgtcatcaaa gagttcatgc gcttcaaggt    7860
gcgcatggag ggctccatga acggccacga gttcgagatc gagggcgagg cgagggccg    7920 cccctacgag ggcacccaga ccgccaagct gaaggtgacc aagggcggcc cctgcccttt    7980
cgcctgggac atcctgtccc ccagttcat gtacggctcc aaggcgtacg tgaagcaccc    8040
cgccgacatc cccgattaca agaagctgtc cttccccgag ggcttcaagt gggagcgcgt    8100
gatgaacttc gaggacggcg gtctggtgac cgtgacccag gactcctccc tgcaggacgg    8160
cacgctgatc tacaaggtga agatgcgcgg caccaacttc ccccccgacg gccccgtaat    8220
gcagaagaag accatgggct gggaggcctc caccgagcgc ctgtaccccc gcgacggcgt    8280
gctgaagggc gagatccacc aggccctgaa gctgaaggac ggcggccact acctggtgga    8340
gttcaagacc atctacatgg ccaagaagcc cgtgcaactg cccggctact actacgtgga    8400
caccaagctg gacatcacct cccacaacga ggactacacc atcgtggaac agtacgagcg    8460
ctccgagggc cgccaccacc tgttcctgta cggcatggac gagctgtaca agaccacttc    8520
gtgcgaaaac ctgtacttcc aaggtatggt gagcaagggc gaggaggtca tcaaagagtt    8580
catgcgcttc aaggtgcgca tggagggctc catgaacggc cacgagttcg agatcgaggg    8640
cgagggcgag ggccgcccct acgagggcac ccagaccgcc aagctgaagg tgaccaaggg    8700 cggcccctg cccttcgcct gggacatcct gtcccccag ttcatgtacg ctccaaggc    8760 gtacgtgaag caccccgccg acatccccga ttacaagaag ctgtccttcc ccgagggctt    8820
caagtgggag cgcgtgatga acttcgagga cggcggtctg gtgaccgtga cccaggactc    8880
ctccctgcag gacggcacgc tgatctacaa ggtgaagatg cgcggcacca acttcccccc    8940
cgacggcccc gtaatgcaga agaagaccat gggctgggag gcctccaccg agcgcctgta    9000 ccccgcgac ggcgtgctga agggcgagat ccaccaggcc ctgaagctga aggacggcgg    9060
ccactacctg gtggagttca agaccatcta catggccaag aagcccgtgc aactgccggc    9120
ctactactac gtggacacca agctggacat cacctcccac aacgaggact acaccatcgt    9180
```

```
ggaacagtac gagcgctccg agggccgcca ccacctgttc ctggggcatg gcaccggcag    9240
caccggcagc ggcagctccg gcaccgcctc ctccgaggac aacaacatgg ccgtcatcaa    9300
agagttcatg cgcttcaagg tgcgcatgga gggctccatg aacggccacg agttcgagat    9360
cgagggcgag ggcgagggcc gcccctacga gggcacccag accgccaagc tgaaggtgac    9420
caagggcggc cccctgccct tcgcctggga catcctgtcc ccccagttca tgtacggctc    9480
caaggcgtac gtgaagcacc ccgccgacat ccccgattac aagaagctgt ccttccccga    9540
gggcttcaag tgggagcgcg tgatgaactt cgaggacggc ggtctggtga ccgtgaccca    9600
ggactcctcc ctgcaggacg gcacgctgat ctacaaggtg aagatgcgcg gcaccaactt    9660 ccccccccgac ggccccgtaa tgcagaagaa gaccatgggc tgggaggcct ccaccgagcg    9720
cctgtacccc cgcgacggcg tgctgaaggg cgagatccac caggccctga gctgaagga    9780 cggcggccac tacctggtgg agttcaagac catctacatg gccaagaagc ccgtgcaact    9840
gcccggctac tactacgtgg acaccaagct ggacatcacc tcccacaacg aggactacac    9900
catcgtggaa cagtacgagc gctccgaggg ccgccaccac ctgttcctgt acggcatgga    9960
cgagctgtac aaggaaaacc tgtacttcca aagtggagaa agcttgttta agggaccacg   10020
tgattacaac ccgatatcga gcaccatttg tcatttgacg aatgaatctg atgggcacac   10080
aacatcgttg tatggtattg gatttggtcc cttcatcatt acaaacaagc acttgtttag   10140
aagaaataat ggaacactgt tggtccaatc actacatggt gtattcaagg tcaagaacac   10200
cacgactttg caacaacacc tcattgatgg gagggacatg ataattattc gcatgcctaa   10260 ggatttcccca ccatttcctc aaaagctgaa atttagagag ccacaaaggg aagagcgcat   10320
atgtcttgtg acaaccaact tccaaactaa gagcatgtct agcatggtgt cagacactag   10380
ttgcacattc ccttcatctg atggcatatt ctggaagcat tggattcaaa ccaaggatgg   10440
gcagtgtggc agtccattag tatcaactag agatgggttc attgttggta tacactcagc   10500
atcgaatttc accaacacaa acaattattt cacaagcgtg ccgaaaaact tcatggaatt   10560
gttgacaaat caggaggcgc agcagtgggt tagtggttgg cgattaaatg ctgactcagt   10620
attgtggggg ggccataaag ttttcatgag caaacctgaa gagcctttc agccagttaa    10680 ggaagcgact caactcatga atgaattggt gtactcgcaa gaaaacctgt acttccaaag   10740
tatgcataga tcacgagata tcagccatgg cttcccgccg gcggtggcgg cgcaggatga   10800
tggcacgctg cccatgtctt gtgcccagga gagcgggatg gaccgtcacc ctgcagcctg   10860
tgcttctgct aggatcaatg tggagctcgt gcacctgact cctgaggaga gtctgccgt    10920 tactgccctg tggggcaagg tgaacgtgga tgaagttggt ggtgaggccc tgggcaggct   10980
gctggtggtc tacccttgga cccagaggtt ctttgagtcc tttggggatc tgtccactcc   11040
tgatgctgtt atgggcaacc ctaaggtgaa ggctcatggc aagaaagtgc tcggtgcctt   11100
tagtgatggc ctggctcacc tggacaacct caagggcacc tttgccacac tgagtgagct   11160
gcactgtgac aagctgcacg tggatcctga aacttcagg gtgagtctat gggacccttg    11220
atgttttctt tccccttctt ttctatggtt aagttcatgt cataggaagg ggataagtaa   11280
cagggtacag tttagaatgg gaaacagacg aatgattgca tcagtgtgga agtctcagga   11340
tcgttttagt ttctttttatt tgctgttcat aacaattgtt ttcttttgtt taattcttgc   11400
tttctttttt tttcttctcc gcaatttttta ctattatact taatgcctta acattgtgta   11460
taacaaaagg aaatatctct gagatacatt aagtaactta aaaaaaaaac tttacacagt   11520
```

```
ctgcctagta cattactatt tggaatatat gtgtgcttat ttgcatattc ataatctccc   11580
tactttattt tcttttattt ttaattgata cataatcatt atacatattt atgggttaaa   11640
gtgtaatgtt ttaatatgtg tacacatatt gaccaaatca gggtaatttt gcatttgtaa   11700
ttttaaaaaa tgctttcttc ttttaatata cttttttgtt tatcttattt ctaatacttt   11760
ccctaatctc tttctttcag ggcaataatg atacaatgta tcatgcctct ttgcaccatt   11820
ctaaagaata acagtgataa tttctgggtt aaggcaatag caatatttct gcatataaat   11880
atttctgcat ataaattgta actgatgtaa gaggtttcat attgctaata gcagctacaa   11940
tccagctacc attctgcttt tattttatgg ttgggataag gctggattat tctgagtcca   12000
agctaggccc ttttgctaat catgttcata cctcttatct tcctcccaca gctcctgggc   12060
aacgtgctgg tctgtgtgct ggcccatcac tttggcaaag aattcacccc accagtgcag   12120
gctgcctatc agaaagtggt ggctggtgtg ctaatgccc tgcccacaa gtatcactaa   12180 gcggccgctc gctttcttgc tgtccaattt ctattaaagg ttcctttgtt ccctaagtcc   12240
aactactaaa ctgggggata ttatgaaggg cctcgaggct gatcagcctc gactgtgcct   12300
tctagttgcc agccatctgt tgtttgcccc tcccccgtgc cttccttgac cctggaaggt   12360
gccactccca ctgtcctttc ctaataaaat gaggaaattg catcgcattg tctgagtagg   12420
tgtcattcta ttctgggggg tggggtgggg caggacagca aggggagga ttgggaagac   12480 aatagcaggc atgctgggga tgcggtgggc tctatggctt ctgaggcgga aagaaccagc   12540
tggggctcta gggggtatcc ccacgcgccc tgtagcggcg cattaagcgc ggcgggtgtg   12600
gtggttacgc gcagcgtgac cgctacactt gccagcgccc tagcgcccgc tcctttcgct   12660
ttcttccctt cctttctcgc cacgttcgcc ggctttcccc gtcaagctct aaatcggggg   12720
ctccctttag ggttccgatt tagtgcttta cggcacctcg accccaaaaa acttgattag   12780
ggtgatggtt cacgtaggta cgctagcacc gttggtttcc gtagtgtagt ggttatcacg   12840
ttcgcctaac acgcgaaagg tccccggttc gaaaccgggc actacaaacc aacaacgctg   12900
gtacccctag aagttcctat tccgaagttc ctattctcta gaaagtatag gaacttcctt   12960
ggccaaaaag cctgaactca ccgcgacgtc tgtcgagaag tttctgatcg aaaagttcga   13020
cagcgtctcc gacctgatgc agctctcgga gggcgaagaa tctcgtgctt tcagcttcga   13080
tgtaggaggg cgtggatatg tcctgcgggt aaatagctgc gccgatggtt tctacaaaga   13140
tcgttatgtt tatcggcact ttgcatcggc cgcgctcccg attccggaag tgcttgacat   13200
tggggaattc agcgagagcc tgacctattg catctcccgc cgtgcacagg gtgtcacgtt   13260
gcaagacctg cctgaaaccg aactgcccgc tgttctgcag ccggtcgcgg aggccatgga   13320
tgcgatcgct gcggccgatc ttagccagac gagcgggttc ggcccattcg gaccgcaagg   13380
aatcggtcaa tacactacat ggcgtgattt catatgcgcg attgctgatc cccatgtgta   13440
tcactggcaa actgtgatgg acgacaccgt cagtgcgtcc gtcgcgcagg ctctcgatga   13500
gctgatgctt tgggccgagg actgccccga agtccggcac ctcgtgcacg cggatttcgg   13560
ctccaacaat gtcctgacgg acaatggccg cataacagcg gtcattgact ggagcgaggc   13620
gatgttcggg gattcccaat acgaggtcgc caacatcttc ttctggaggc cgtggttggc   13680
ttgtatggag cagcagacgc gctacttcga gcggaggcat ccggagcttg caggatcgcc   13740
gcggctccgg gcgtatatgc tccgcattgg tcttgaccaa ctctatcaga gcttggttga   13800
cggcaatttc gatgatgcag cttgggcgca gggtcgatgc gacgcaatcg tccgatccgg   13860
agccgggact gtcgggcgta cacaaatcgc ccgcagaagc gcggccgtct ggaccgatgg   13920
```

```
ctgtgtagaa gtactcgccg atagtggaaa ccgacgcccc agcactcgtc cgagggcaaa    13980
ggaatagcac gtactacgag atttcgattc caccgccgcc ttctatgaaa ggttgggctt    14040
cggaatcgtt ttccgggacg ccggctggat gatcctccag cgcggggatc tcatgctgga    14100
gttcttcgcc caccccaact tgtttattgc agcttataat ggttacaaat aaagcaatag    14160
catcacaaat ttcacaaata aagcattttt tcactgcat tctagttgtg gtttgtccaa     14220
actcatcaat gtatcttatc atgtctgtat accgtcgaca ggtggcactt ttcggggaaa    14280
tgtgcgcgga acccctattt gtttattttt ctaaatacat tcaaatatgt atccgctcat    14340
gagacaataa ccctgataaa tgcttcaata atattgaaaa aggaagagta tgagtattca    14400
acatttccgt gtcgccctta ttcccttttt tgcggcattt tgccttcctg tttttgctca    14460
cccagaaacg ctggtgaaag taaaagatgc tgaagatcag ttgggtgcac gagtgggtta    14520
catcgaactg gatctcaaca gcggtaagat ccttgagagt tttcgccccg aagaacgttt    14580
tccaatgatg agcactttta aagttctgct atgtggcgcg gtattatccc gtattgacgc    14640
cgggcaagag caactcggtc gccgcataca ctattctcag aatgacttgg ttgagtactc    14700
accagtcaca gaaaagcatc ttacggatgg catgacagta agagaattat gcagtgctgc    14760
cataaccatg agtgataaca ctgcggccaa cttacttctg acaacgatcg gaggaccgaa    14820
ggagctaacc gcttttttgc acaacatggg ggatcatgta actcgccttg atcgttggga    14880
accggagctg aatgaagcca taccaaacga cgagcgtgac accacgatgc ctgtagcaat    14940
ggcaacaacg ttgcgcaaac tattaactgg cgaactactt actctagctt cccggcaaca    15000
attaatagac tggatggagg cggataaagt tgcaggacca cttctgcgct cggcccttcc    15060
ggctggctgg tttattgctg ataaatctgg agccggtgag cgtgggtctc gcggtatcat    15120
tgcagcactg gggccagatg gtaagccctc ccgtatcgta gttatctaca cgacggggag    15180
tcaggcaact atggatgaac gaaatagaca gatcgctgag ataggtgcct cactgattaa    15240
gcattggtaa ctgtcagacc aagtttactc atatatactt tagattgatt taaa          15294
```

<210> SEQ ID NO 3
<211> LENGTH: 15294
<212> TYPE: DNA
<213> ORGANISM: Artificial Sequence
<220> FEATURE:
<223> OTHER INFORMATION: AVA2626[RFP(PTC+), HygromycinR] vector sequence

<400> SEQUENCE: 3

```
acttcatttt taatttaaaa ggatctaggt gaagatcctt tttgataatc tcatgaccaa       60
aatcccttaa cgtgagtttt cgttccactg agcgtcagac cccgtagaaa agatcaaagg      120
atcttcttga tccttttttt ttctgcgcgt aatctgctgc ttgcaaacaa aaaaaccacc      180
gctaccagcg gtggtttgtt tgccggatca agagctacca actctttttc cgaaggtaac      240
tggcttcagc agagcgcaga taccaaatac tgtccttcta gtgtagccgt agttaggcca      300
ccacttcaag aactctgtag caccgcctac atacctcgct ctgctaatcc tgttaccagt      360
ggctgctgcc agtggcgata agtcgtgtct taccgggttg gactcaagac gatagttacc      420
ggataaggcg cagcggtcgg gctgaacggg gggttcgtgc acacagccca gcttggagcg      480
aacgacctac accgaactga gatacctaca gcgtgagcta tgagaaagcg ccacgcttcc      540
cgaagggaga aaggcggaca ggtatccggt aagcggcagg gtcggaacag gagagcgcac      600
gagggagctt ccagggggaa acgcctggta tctttatagt cctgtcgggt ttcgccacct      660
```

```
ctgacttgag cgtcgatttt tgtgatgctc gtcagggggg cggagcctat ggaaaaacgc    720
cagcaacgcg gccttttttac ggttcctggc cttttgctgg ccttttgctc acatgttctt    780
tcctgcgtta tccctgatt ctgtggataa ccgtattacc gcctttgagt gagctgatac    840
cgctcgccgc agccgaacga ccgagcgcag cgagtcagtg agcgaggaag cggaagagcg    900
cccaatacgc aaaccgcctc tccccgcgcg ttggccgatt cattaatgca gctggcacga    960
caggtttccc gactggaaag cgggcagtga gcgcaacgca attaatgtga gttagctcac   1020
tcattaggca ccccaggcac gcgaagcgtt gttggtttgt agtgcccggt tcgaaccgg   1080 ggaccttcg cgtgttaggc gaacgtgata accactacac tacggaaacc aacggtgcta   1140
gacgcgtatt gtctattctg actcggatcc gtacgaattc tcatgtttga cagcttatca   1200
tcgattagct ttggagctaa gccagcaatg gtagagggaa gattctgcac gtcccttcca   1260
ggcggcctcc ccgtcaccac cccccccaac ccgccccgac cggagctgag agtaattcat   1320
acaaaaggac tcgcccctgc cttggggaat cccaggacc gtcgttaaac tcccactaac   1380
gtagaaccca gagatcgctg cgttcccgcc ccctcacccg cccgctctcg tcatcactga   1440
ggtggagaag agcatgcgtg aggctccggt gcccgtcagt gggcagagcg cacatcgccc   1500
acagtccccg agaagttggg gggaggggtc ggcaattgaa ccggtgccta gagaaagtgg   1560
cgcggggtaa actgggaaag tgatgtcgtg tactggctcc gccttttttcc cgagggtggg   1620 ggagaaccgt atataagtgc agtagtcgcc gtgaacgttc ttttttcgcaa cgggtttgcc   1680 gccagaacac aggtaagtgc cgtgtgtggt tcccgcgggc ctggcctctt tacgggttat   1740
ggcccttgcg tgccttgaat tacttccacg ccctggctg cagtacgtga ttcttgatcc   1800
cgagcttcgg gttggaagtg ggtgggagag ttcgaggcct tgcgcttaag gagccccttc   1860
gcctcgtgct tgagttgagg cctggcctgg gcgctgggc cgccgcgtgc gaatctggtg   1920
gcaccttcgc gcctgtctcg ctgctttcga taagtctcta gccatttaaa attttttgatg   1980 acctgctgcg acgcttttttt tctggcaaga tagtcttgta aatgcgggcc aagatctgca   2040
cactggtatt tcggtttttg gggccgcggg cggcgacggg gcccgtgcgt cccagcgcac   2100
atgttcggcg aggcggggcc tgcgagcgcg gccaccgaga tcggacggg ggtagtctca   2160 agctggccgg cctgctctgg tgcctggcct cgcgccgccg tgtatcgccc cgccctgggc   2220
ggcaacaggc tggcccggtc ggcaccagtt gcgtgagcgg aaagatggcc gcttcccggc   2280
cctgctgcag ggagctcaaa atggaggacg cggcgctcgg gagagcgggc gggtgagtca   2340
cccacacaaa ggaaaagggc cttttccgtcc tcagccgtcg cttcatgtga ctccacggag   2400
taccgggcgc cgtccaggca cctcgattag ttctcgagct tttggagtac gtcgtcttta   2460
ggttgggggg aggggtttta tgcgatggag tttccccaca ctgagtgggt ggagactgaa   2520
gttaggccag cttggcactt gatgtaattc tccttggaat ttgcccttt tgagtttgga   2580 tcttggttca ttctcaagcc tcagacagtg gttcaaagtt tttttcttcc atttcaggtg   2640
tcgtgaaaac tctagcgttt ccgctctaga actagtccag ctagcgctac cggtcgccac   2700
catggtgagc aagggcgagg aggtcatcaa agagttcatg cgcttcaagg tgcgcatgga   2760
gggctccatg aacggccacg agttcgagat cgagggcgag ggcgagggcc gccctacga   2820 gggcacccag accgccaagc tgaaggtgac caagggcggc cccctgccct cgcctggga   2880 catcctgtcc cccagttca tgtacggctc caaggcgtac gtgaagcacc ccgccgacat   2940
ccccgattac aagaagctgt ccttccccga gggcttcaag tgggagcgcg tgatgaactt   3000
cgaggacggc ggtctggtga ccgtgaccca ggactcctcc ctgcaggacg gcacgctgat   3060
```

```
ctacaaggtg aagatgcgcg gcaccaactt ccccccgac ggccccgtaa tgcagaagaa     3120
gaccatgggc tgggaggcct ccaccgagcg cctgtacccc cgcgacggcg tgctgaaggg     3180
cgagatccac caggccctga agctgaagga cggcggccac tacctggtgg agttcaagac     3240
catctacatg gccaagaagc ccgtgcaact gcccggctac tactacgtgg acaccaagct     3300
ggacatcacc tcccacaacg aggactacac catcgtggaa cagtacgagc gctccgaggg     3360
ccgccaccac ctgttcctgg ggcatggcac cggcagcacc ggcagcggca gctccggcac     3420
cgcctcctcc gaggacaaca acatggccgt catcaaagag ttcatgcgct tcaaggtgcg     3480
catggagggc tccatgaacg gccacgagtt cgagatcgag ggcgagggcg agggccgccc     3540
ctacgagggc acccagaccg ccaagctgaa ggtgaccaag ggcggccccc tgcccttcgc     3600
ctgggacatc ctgtcccccc agttcatgta cggctccaag gcgtacgtga agcaccccgc     3660
cgacatcccc gattacaaga agctgtcctt ccccgagggc ttcaagtggg agcgcgtgat     3720
gaacttcgag gacggcggtc tggtgaccgt gacccaggac tcctccctgc aggacggcac     3780
gctgatctac aaggtgaaga tgcgcggcac caacttcccc ccgacggcc ccgtaatgca     3840 gaagaagacc atgggctggg aggcctccac cgagcgcctg taccccgcg acggcgtgct     3900 gaagggcgag atccaccagg ccctgaagct gaaggacggc ggccactacc tggtggagtt     3960
caagaccatc tacatggcca agaagcccgt gcaactgccc ggctactact acgtggacac     4020
caagctggac atcacctccc acaacgagga ctacaccatc gtggaacagt acgagcgctc     4080
cgagggccgc caccacctgt tcctgtacgg catggacgag ctgtacaagg tcactccgtg     4140
tgaaaacctg tacttccaag gtatggtgag caagggcgag gaggtcatca agagttcat     4200 gcgcttcaag gtgcgcatgg agggctccat gaacggccac gagttcgaga tcgagggcga     4260
gggcgagggc cgcccctacg agggcaccca gaccgccaag ctgaaggtga ccaagggcgg     4320
ccccctgccc ttcgcctggg acatcctgtc ccccagttc atgtacggct ccaaggcgta     4380
cgtgaagcac cccgccgaca tccccgatta caagaagctg tccttccccg agggcttcaa     4440
gtgggagcgc gtgatgaact tcgaggacgg cggtctggtg accgtgaccc aggactcctc     4500
cctgcaggac ggcacgctga tctacaaggt gaagatgcgc ggcaccaact tccccccga     4560 cggccccgta atgcagaaga agaccatggg ctgggaggcc tccaccgagc gcctgtaccc     4620
ccgcgacggg gtgctgaagg gcgagatcca ccaggccctg aagctgaagg acggcggcca     4680
ctacctggtg gagttcaaga ccatctacat ggccaagaag cccgtgcaac tgcccggcta     4740
ctactacgtg gacaccaagc tggacatcac ctcccacaac gaggactaca ccatcgtgga     4800
acagtacgag cgctccgagg gccgccacca cctgttcctg gggcatggca ccggcagcac     4860
cggcagcggc agctccggca ccgcctcctc cgaggacaac aacatggccg tcatcaaaga     4920
gttcatgcgc ttcaaggtgc gcatggaggg ctccatgaac ggccacgagt tcgagatcga     4980
gggcgagggc gagggccgcc cctacgaggg cacccagacc gccaagctga aggtgaccaa     5040
gggcggcccc ctgcccttcg cctgggacat cctgtccccc agttcatgt acggctccaa     5100 ggcgtacgtg aagcaccccg ccgacatccc cgattacaag aagctgtcct tccccgaggg     5160
cttcaagtgg gagcgcgtga tgaacttcga ggacggcggt ctggtgaccg tgacccagga     5220
ctcctccctg caggacggca cgctgatcta caaggtgaag atgcgcggca ccaacttccc     5280
ccccgacggc cccgtaatgc agaagaagac catgggctgg gaggcctcca ccgagcgcct     5340 gtaccccgc gacggcgtgc tgaagggcga gatccaccag gccctgaagc tgaaggacgg     5400
```

-continued

```
cggccactac ctggtggagt tcaagaccat ctacatggcc aagaagcccg tgcaactgcc    5460
cggctactac tacgtggaca ccaagctgga catcacctcc cacaacgagg actacaccat    5520
cgtggaacag tacgagcgct ccgagggccg ccaccacctg ttcctgtacg gcatggacga    5580
gctgtacaag accactgcgt gcgaaaacct gtacttccaa ggtatggtga gcaagggcga    5640
ggaggtcatc aaagagttca tgcgcttcaa ggtgcgcatg gagggctcca tgaacggcca    5700
cgagttcgag atcgagggcg agggcgaggc cgcccctac gagggcaccc agaccgccaa    5760
gctgaaggtg accaagggcg gccccctgcc cttcgcctgg gacatcctgt cccccagtt    5820 catgtacggc tccaaggcgt acgtgaagca ccccgccgac atccccgatt acaagaagct    5880
gtccttcccc gagggcttca gtgggagcg cgtgatgaac ttcgaggacg gcggtctggt    5940
gaccgtgacc caggactcct ccctgcagga cggcacgctg atctacaagg tgaagatgcg    6000
cggcaccaac ttccccccgc acggccccgt aatgcagaag aagaccatgg gctgggaggc    6060
ctccaccgag cgcctgtacc cccgcgacgg cgtgctgaag ggcgagatcc accaggccct    6120
gaagctgaag gacggcggcc actacctggt ggagttcaag accatctaca tggccaagaa    6180
gcccgtgcaa ctgcccggct actactacgt ggacaccaag ctggacatca cctcccacaa    6240
cgaggactac accatcgtgg aacagtacga gcgctccgag gccgccacc acctgttcct    6300 ggggcatggc accggcagca ccggcagcgg cagctccggc accgcctcct ccgaggacaa    6360
caacatggcc gtcatcaaag agttcatgcg cttcaaggtg cgcatggagg ctccatgaa    6420 cggccacgag ttcgagatcg agggcgaggg cgagggccgc cctacgagg caccagac     6480 cgccaagctg aaggtgacca agggcggccc cctgcccttc gctgggaca tcctgtcccc    6540 ccagttcatg tacggctcca aggcgtacgt gaagcacccc gccgacatcc ccgattacaa    6600
gaagctgtcc ttccccgagg gcttcaagtg ggagcgcgtg atgaacttcg aggacggcgg    6660
tctggtgacc gtgacccagg actcctccct gcaggacggc acgctgatct acaaggtgaa    6720
gatgcgcggc accaacttcc ccccgacgg ccccgtaatg cagaagaaga ccatgggctg    6780
ggaggcctcc accgagcgcc tgtaccccg cgacggcgtg ctgaagggcg agatccacca    6840
ggccctgaag ctgaaggacg gcggccacta cctggtggag ttcaagacca tctacatggc    6900
caagaagccc gtgcaactgc ccggctacta ctacgtggac accaagctgg acatcacctc    6960
ccacaacgag gactacacca tcgtggaaca gtacgagcgc tccgagggcc gccaccacct    7020
gttcctgtac ggcatggacg agctgtacaa ggtcactacg tgtgaaaacc tgtacttcca    7080
aggtatggtg agcaagggcg aggaggtcat caaagagttc atgcgcttca aggtgcgcat    7140
ggagggctcc atgaacggcc acgagttcga gatcgagggc gagggcgagg ccgcccta    7200 cgagggcacc cagaccgcca agctgaaggt gaccaagggc ggccccctgc ccttcgcctg    7260
ggacatcctg tcccccagt tcatgtacgg ctccaaggcg tacgtgaagc accccgccga    7320
catccccgat tacaagaagc tgtccttccc cgagggcttc aagtgggagc gcgtgatgaa    7380
cttcgaggac ggcggtctgg tgaccgtgac ccaggactcc tccctgcagg acggcacgct    7440
gatctacaag gtgaagatgc gcggcaccaa cttccccccc gacggccccg taatgcagaa    7500
gaagaccatg ggctgggagg cctccaccga gcgcctgtac cccgcgacg gcgtgctgaa    7560 gggcgagatc caccaggccc tgaagctgaa ggacggcggc cactacctgg tggagttcaa    7620
gaccatctac atggccaaga agcccgtgca actgcccggc tactactacg tggacaccaa    7680
gctggacatc acctcccaca acgaggacta caccatcgtg aacagtacg agcgctccga    7740 gggccgccac cacctgttcc tggggcatgg caccggcagc accggcagcg gcagctccgg    7800
```

```
caccgcctcc tccgaggaca acaacatggc cgtcatcaaa gagttcatgc gcttcaaggt    7860
gcgcatggag ggctccatga acggccacga gttcgagatc gagggcgagg gcagggccg    7920 cccctacgag ggcacccaga ccgccaagct gaaggtgacc aagggcggcc ccctgccctt    7980
cgcctgggac atcctgtccc cccagttcat gtacggctcc aaggcgtacg tgaagcaccc    8040
cgccgacatc cccgattaca agaagctgtc cttccccgag ggcttcaagt gggagcgcgt    8100
gatgaacttc gaggacggcg gtctggtgac cgtgacccag gactcctccc tgcaggacgg    8160
cacgctgatc tacaaggtga agatgcgcgg caccaacttc cccccgacg gccccgtaat    8220 gcagaagaag accatgggct gggaggcctc caccgagcgc ctgtaccccc gcgacggcgt    8280
gctgaagggc gagatccacc aggccctgaa gctgaaggac ggcggccact acctggtgga    8340
gttcaagacc atctacatgg ccaagaagcc cgtgcaactg cccggctact actacgtgga    8400
caccaagctg gacatcacct cccacaacga ggactacacc atcgtggaac agtacgagcg    8460
ctccgagggc cgccaccacc tgttcctgta cggcatggac gagctgtaca agaccacttc    8520
gtgcgaaaac ctgtacttcc aaggtatggt gagcaagggc gaggaggtca tcaaagagtt    8580
catgcgcttc aaggtgcgca tggagggctc catgaacggc cacagttcg agatcgaggg    8640 cgagggcgag ggccgcccct acgagggcac ccagaccgcc aagctgaagg tgaccaaggg    8700
cggccccctg cccttcgcct gggacatcct gtcccccag ttcatgtacg gctccaaggc    8760
gtacgtgaag caccccgccg acatccccga ttacaagaag ctgtccttcc ccgagggctt    8820
caagtgggag cgcgtgatga acttcgagga cggcggtctg gtgaccgtga cccaggactc    8880
ctccctgcag gacggcacgc tgatctacaa ggtgaagatg cgcggcacca acttcccccc    8940
cgacggcccc gtaatgcaga agaagaccat gggctgggag gcctccaccg agcgcctgta    9000
cccccgcgac ggcgtgctga agggcgagat ccaccaggcc ctgaagctga aggacggcgg    9060
ccactacctg gtggagttca gaccatctta catggccaag aagcccgtgc aactgcccgg    9120
ctactactac gtggacacca gctggacat cacctcccac aacgaggact acaccatcgt    9180
ggaacagtac gagcgctccg agggccgcca ccacctgttc ctgggcatg gcaccggcag    9240 caccggcagc ggcagctccg gcaccgcctc ctccgaggac aacaacatgg ccgtcatcaa    9300
agagttcatg cgcttcaagg tgcgcatgga gggctccatg aacggccacg agttcgagat    9360
cgagggcgag ggcgagggcc gccctacga gggcacccag accgccaagc tgaaggtgac    9420
caagggcggc cccctgccct tcgcctggga catcctgtcc cccagttca tgtacggctc    9480 caaggcgtac gtgaagcacc ccgccgacat ccccgattac aagaagctgt ccttcccga    9540 gggcttcaag tgggagcgcg tgatgaactt cgaggacggc ggtctggtga ccgtgaccca    9600
ggactcctcc ctgcaggacg gcacgctgat ctacaaggtg aagatgcgcg gcaccaactt    9660 ccccccgac ggccccgtaa tgcagaagaa gaccatgggc tgggaggcct ccaccgagcg    9720
cctgtacccc cgcgacggcg tgctgaaggg cgagatccac caggccctga gctgaagga    9780 cggcggccac tacctggtgg agttcaagac catctacatg gccaagaagc ccgtgcaact    9840
gcccggctac tactacgtgg acaccaagct ggacatcacc tcccacaacg aggactacac    9900
catcgtggaa cagtacgagc gctccgaggg ccgccaccac ctgttcctgt acggcatgga    9960
cgagctgtac aaggaaaacc tgtacttcca aagtggagaa agcttgttta agggaccacg   10020
tgattacaac ccgatatcga gcaccatttg tcatttgacg aatgaatctg atgggcacac   10080
aacatcgttg tatggtattg gatttggtcc cttcatcatt acaaacaagc acttgtttag   10140
```

```
aagaaataat ggaacactgt tggtccaatc actacatggt gtattcaagg tcaagaacac    10200
cacgactttg caacaacacc tcattgatgg gagggacatg ataattattc gcatgcctaa    10260
ggatttccca ccatttcctc aaaagctgaa atttagagag ccacaaaggg aagagcgcat    10320
atgtcttgtg acaaccaact tccaaactaa gagcatgtct agcatggtgt cagacactag    10380
ttgcacattc ccttcatctg atggcatatt ctggaagcat tggattcaaa ccaaggatgg    10440
gcagtgtggc agtccattag tatcaactag agatgggttc attgttggta tacactcagc    10500
atcgaatttc accaacacaa acaattattt cacaagcgtg ccgaaaaact tcatggaatt    10560
gttgacaaat caggaggcgc agcagtgggt tagtggttgg cgattaaatg ctgactcagt    10620
attgtggggg ggccataaag ttttcatgag caaacctgaa gagccttttc agccagttaa    10680
ggaagcgact caactcatga atgaattggt gtactcgcaa gaaaacctgt acttccaaag    10740
tatgcataga tcacgagata tcagccatgg cttcccgccg gcggtggcgg cgcaggatga    10800
tggcacgctg cccatgtctt gtgcccagga gagcgggatg gaccgtcacc ctgcagcctg    10860
tgcttctgct aggatcaatg tggagctcgt gcacctgact cctgaggaga agtctgccgt    10920
tactgccctg tggggcaagg tgaacgtgga tgaagttggt ggtgaggccc tgggcaggct    10980
gctggtggtc tacccttgga cctagaggtt ctttgagtcc tttggggatc tgtccactcc    11040
tgatgctgtt atgggcaacc ctaaggtgaa ggctcatggc aagaaagtgc tcggtgcctt    11100
tagtgatggc ctggctcacc tggacaacct caagggcacc tttgccacac tgagtgagct    11160
gcactgtgac aagctgcacg tggatcctga aacttcagg gtgagtctat gggacccttg    11220
atgttttctt tccccttctt ttctatggtt aagttcatgt cataggaagg ggataagtaa    11280
cagggtacag tttagaatgg gaaacagacg aatgattgca tcagtgtgga agtctcagga    11340
tcgttttagt ttcttttatt tgctgttcat aacaattgtt ttcttttgtt taattcttgc    11400
tttctttttt tttcttctcc gcaattttta ctattatact taatgcctta acattgtgta    11460
taacaaaagg aaatatctct gagatacatt aagtaactta aaaaaaaaac tttacacagt    11520
ctgcctagta cattactatt tggaatatat gtgtgcttat ttgcatattc ataatctccc    11580
tactttattt tcttttattt ttaattgata cataatcatt atacatattt atgggttaaa    11640
gtgtaatgtt ttaatatgtg tacacatatt gaccaaatca gggtaatttt gcatttgtaa    11700
ttttaaaaaa tgcttttcttc ttttaatata cttttttgtt tatcttatttt ctaatacttt    11760 ccctaatctc tttctttcag ggcaataatg atacaatgta tcatgcctct ttgcaccatt    11820
ctaaagaata acagtgataa tttctggggtt aaggcaatag caatatttct gcatataaat    11880
atttctgcat ataaattgta actgatgtaa gaggtttcat attgctaata gcagctacaa    11940
tccagctacc attctgcttt tatttttatgg ttgggataag gctggattat tctgagtcca    12000
agctaggccc ttttgctaat catgttcata cctcttatct tcctcccaca gctcctgggc    12060
aacgtgctgg tctgtgtgct ggcccatcac tttggcaaag aattcacccc accagtgcag    12120
gctgcctatc agaaagtggt ggctggtgtg ctaatgccc tggcccacaa gtatcactaa    12180
gcggccgctc gctttcttgc tgtccaattt ctattaaagg ttcctttgtt ccctaagtcc    12240
aactactaaa ctgggggata ttatgaaggg cctcgaggct gatcagcctc gactgtgcct    12300
tctagttgcc agccatctgt tgtttgcccc tcccccgtgc cttccttgac cctggaaggt    12360
gccactccca ctgtcctttc taataaaat gaggaaattg catcgcattg tctgagtagg    12420
tgtcattcta ttctgggggg tggggtgggg caggacagca agggggagga ttgggaagac    12480
aatagcaggc atgctgggga tgcggtgggc tctatggctt ctgaggcgga aagaaccagc    12540
```

```
tggggctcta gggggtatcc ccacgcgccc tgtagcggcg cattaagcgc ggcgggtgtg   12600
gtggttacgc gcagcgtgac cgctacactt gccagcgccc tagcgcccgc tcctttcgct   12660
ttcttccctt cctttctcgc cacgttcgcc ggctttcccc gtcaagctct aaatcggggg   12720 ctcccttag ggttccgatt tagtgcttta cggcacctcg accccaaaaa acttgattag    12780
ggtgatggtt cacgtaggta cgctagcacc gttggtttcc gtagtgtagt ggttatcacg   12840
ttcgcctaac acgcgaaagg tccccggttc gaaaccgggc actacaaacc aacaacgctg   12900 gtaccctag aagttcctat tccgaagttc ctattctcta gaaagtatag gaacttcctt    12960
ggccaaaaag cctgaactca ccgcgacgtc tgtcgagaag tttctgatcg aaaagttcga   13020
cagcgtctcc gacctgatgc agctctcgga gggcgaagaa tctcgtgctt tcagcttcga   13080
tgtaggaggg cgtggatatg tcctgcgggt aaatagctgc gccgatggtt tctacaaaga   13140
tcgttatgtt tatcggcact ttgcatcggc cgcgctcccg attccggaag tgcttgacat   13200
tggggaattc agcgagagcc tgacctattg catctcccgc cgtgcacagg gtgtcacgtt   13260
gcaagacctg cctgaaaccg aactgcccgc tgttctgcag ccggtcgcgg aggccatgga   13320
tgcgatcgct gcggccgatc ttagccagac gagcgggttc ggcccattcg gaccgcaagg   13380
aatcggtcaa tacactacat ggcgtgattt catatgcgcg attgctgatc cccatgtgta   13440
tcactggcaa actgtgatgg acgacaccgt cagtgcgtcc gtcgcgcagg ctctcgatga   13500
gctgatgctt tgggccgagg actgccccga agtccggcac ctcgtgcacg cggatttcgg   13560
ctccaacaat gtcctgacgg acaatggccg cataacagcg gtcattgact ggagcgaggc   13620
gatgttcggg gattcccaat acgaggtcgc caacatcttc ttctggaggc cgtggttggc   13680
ttgtatggag cagcagacgc gctacttcga gcggaggcat ccggagcttg caggatcgcc   13740
gcggctccgg gcgtatatgc tccgcattgg tcttgaccaa ctctatcaga gcttggttga   13800
cggcaatttc gatgatgcag cttgggcgca gggtcgatgc gacgcaatcg tccgatccgg   13860
agccgggact gtcgggcgta cacaaatcgc ccgcagaagc gcggccgtct ggaccgatgg   13920
ctgtgtagaa gtactcgccg atagtggaaa ccgacgcccc agcactcgtc cgagggcaaa   13980
ggaatagcac gtactacgag atttcgattc caccgccgcc ttctatgaaa ggttgggctt   14040
cggaatcgtt ttccgggacg ccggctggat gatcctccag cgcggggatc tcatgctgga   14100
gttcttcgcc caccccaact tgtttattgc agcttataat ggttacaaat aaagcaatag   14160
catcacaaat ttcacaaata aagcattttt ttcactgcat tctagttgtg gtttgtccaa   14220
actcatcaat gtatcttatc atgtctgtat accgtcgaca ggtggcactt tcgggaaa    14280 tgtgcgcgga accctatt gtttatttt ctaaatacat tcaaatatgt atccgctcat     14340
gagacaataa ccctgataaa tgcttcaata atattgaaaa aggaagagta tgagtattca   14400
acatttccgt gtcgccctta ttcccttttt tgcggcattt tgccttcctg tttttgctca   14460
cccagaaacg ctggtgaaag taaaagatgc tgaagatcag ttgggtgcac gagtgggtta   14520
catcgaactg gatctcaaca gcggtaagat ccttgagagt tttcgccccg aagaacgttt   14580
tccaatgatg agcacttta aagttctgct atgtggcgcg gtattatccc gtattgacgc    14640
cgggcaagag caactcggtc gccgcataca ctattctcag aatgacttgg ttgagtactc   14700
accagtcaca gaaaagcatc ttacggatgg catgacagta agagaattat gcagtgctgc   14760
cataaccatg agtgataaca ctgcggccaa cttacttctg acaacgatcg gaggaccgaa   14820
ggagctaacc gcttttttgc acaacatggg ggatcatgta actcgccttg atcgttggga   14880
```

```
accggagctg aatgaagcca taccaaacga cgagcgtgac accacgatgc ctgtagcaat    14940
ggcaacaacg ttgcgcaaac tattaactgg cgaactactt actctagctt cccggcaaca    15000
attaatagac tggatggagg cggataaagt tgcaggacca cttctgcgct cggcccttcc    15060
ggctggctgg tttattgctg ataaatctgg agccggtgag cgtgggtctc gcggtatcat    15120
tgcagcactg gggccagatg gtaagccctc ccgtatcgta gttatctaca cgacggggag    15180
tcaggcaact atgatgaac gaaatagaca gatcgctgag ataggtgcct cactgattaa    15240
gcattggtaa ctgtcagacc aagtttactc atatatactt tagattgatt taaa          15294

<210> SEQ ID NO 4
<211> LENGTH: 11448
<212> TYPE: DNA
<213> ORGANISM: Artificial Sequence
<220> FEATURE:
<223> OTHER INFORMATION: AVA2598[GFP(PTC-), PuromycinR] vector sequence

<400> SEQUENCE: 4
acttcatttt taatttaaaa ggatctaggt gaagatcctt tttgataatc tcatgaccaa      60
aatcccttaa cgtgagtttt cgttccactg agcgtcagac cccgtagaaa agatcaaagg     120
atcttcttga tccttttttt tctgcgcgt aatctgctgc ttgcaaacaa aaaaaccacc      180
gctaccagcg gtggtttgtt tgccggatca agagctacca actctttttc cgaaggtaac     240
tggcttcagc agagcgcaga taccaaatac tgtccttcta gtgtagccgt agttaggcca     300
ccacttcaag aactctgtag caccgcctac atacctcgct ctgctaatcc tgttaccagt     360
ggctgctgcc agtggcgata gtcgtgtct taccgggttg gactcaagac gatagttacc     420
ggataaggcg cagcggtcgg gctgaacggg gggttcgtgc acacagccca gcttggagcg     480
aacgacctac accgaactga gatacctaca gcgtgagcta tgagaaagcg ccacgcttcc     540
cgaagggaga aaggcggaca ggtatccggt aagcggcagg gtcggaacag gagagcgcac     600
gagggagctt ccagggggaa acgcctggta tctttatagt cctgtcgggt ttcgccacct     660
ctgacttgag cgtcgatttt tgtgatgctc gtcagggggg cggagcctat ggaaaaacgc     720
cagcaacgcg gccttttac ggttcctggc cttttgctgg ccttttgctc acatgttctt     780
tcctgcgtta tcccctgatt ctgtggataa ccgtattacc gcctttgagt gagctgatac     840
cgctcgccgc agccgaacga ccgagcgcag cgagtcagtg agcgaggaag cggaagagcg     900
cccaatacgc aaaccgcctc tccccgcgcg ttggccgatt cattaatgca gctggcacga     960
caggtttccc gactggaaag cgggcagtga gcgcaacgca attaatgtga gttagctcac    1020
tcattaggca ccccaggcac gcgaagcgtt gttggtttgt agtgcccggt ttcgaaccgg    1080
ggacctttcg cgtgttaggc gaacgtgata accactacac tacggaaacc aacggtgcta    1140
gacgcgtatt gtctattctg actcggatcc gtacgaattc tcatgtttga cagcttatca    1200
tcgattagct ttggagctaa gccagcaatg gtagagggaa gattctgcac gtcccttcca    1260
ggcggcctcc ccgtcaccac cccccccaac ccgcccgac cggagctgag agtaattcat    1320
acaaaaggac tcgcccctgc cttggggaat cccaggggacc gtcgttaaac tcccactaac    1380
gtagaaccca gagatcgctg cgttcccgcc ccctcacccg cccgctctcg tcatcactga    1440
ggtggagaag agcatgcgtg aggctccggt gcccgtcagt gggcagagcg cacatcgccc    1500
acagtccccg agaagttggg gggaggggtc ggcaattgaa ccggtgccta gagaaagtgg    1560
cgcggggtaa actgggaaag tgatgtcgtg tactggctcc gccttttttcc cgagggtggg    1620 ggagaaccgt atataagtgc agtagtcgcc gtgaacgttc ttttttcgcaa cgggtttgcc    1680
```

```
gccagaacac aggtaagtgc cgtgtgtggt tcccgcgggc ctggcctctt tacgggttat    1740
ggcccttgcg tgccttgaat tacttccacg cccctggctg cagtacgtga ttcttgatcc    1800
cgagcttcgg gttggaagtg ggtgggagag ttcgaggcct tgcgcttaag gagcccttc     1860
gcctcgtgct tgagttgagg cctggcctgg gcgctgggc cgccgcgtgc gaatctggtg     1920
gcaccttcgc gcctgtctcg ctgctttcga taagtctcta gccatttaaa atttttgatg    1980
acctgctgcg acgcttttt tctggcaaga tagtcttgta aatgcgggcc aagatctgca    2040
cactggtatt tcggttttg gggccgcggg cggcgacggg gcccgtgcgt cccagcgcac    2100
atgttcggcg aggcggggcc tgcgagcgcg gccaccgaga atcggacggg ggtagtctca    2160
agctggccgg cctgctctgg tgcctggcct cgcgccgccg tgtatcgccc cgccctgggc    2220
ggcaacaggc tggcccggtc ggcaccagtt gcgtgagcgg aaagatggcc gcttcccggc    2280
cctgctgcag ggagctcaaa atggaggacg cggcgctcgg gagagcgggc gggtgagtca    2340
cccacacaaa ggaaaagggc ctttccgtcc tcagccgtcg cttcatgtga ctccacggag    2400
taccgggcgc cgtccaggca cctcgattag ttctcgagct tttggagtac gtcgtcttta    2460
ggttgggggg aggggtttta tgcgatggag tttccccaca ctgagtgggt ggagactgaa    2520
gttaggccag cttggcactt gatgtaattc tccttggaat ttgccctttt tgagtttgga    2580
tcttggttca ttctcaagcc tcagacagtg gttcaaagtt tttttcttcc atttcaggtg    2640
tcgtgaaaac tctagcgttt ccgctctaga actagtccag ctagcgctac cggtcgccac    2700
catggtgagc aagggcgagg agctgttcac cggggtggtg cccatcctgg tcgagctgga    2760
cggcgacgta aacggccaca agttcagcgt gtccggcgag ggcgagggcg atgccaccta    2820
cggcaagctg accctgaagt tcatctgcac caccggcaag ctgcccgtgc cctggcccac    2880
cctcgtgacc accctgacct acggcgtgca gtgcttcagc cgctaccccg accacatgaa    2940
gcagcacgac ttcttcaagt ccgccatgcc cgaaggctac gtccaggagc gcaccatctt    3000
cttcaaggac gacggcaact acaagacccg cgccgaggtg aagttcgagg gcgacaccct    3060
ggtgaaccgc atcgagctga agggcatcga cttcaaggag gacggcaaca tcctggggca    3120
caagctggag tacaactaca acagccacaa cgtctatatc atggccgaca agcagaagaa    3180
cggcatcaag gtgaacttca gatccgcca caacatcgag gacggcagcg tgcagctcgc    3240
cgaccactac cagcagaaca cccccatcgg cgacggcccc gtgctgctgc ccgacaacca    3300
ctacctgagc acccagtccg ccctgagcaa agaccccaac gagaagcgcg atcacatggt    3360
cctgctggag ttcgtgaccg ccgccgggat cactctcggc atggacgagc tgtacaaggt    3420
cactccgtgt gaaaacctgt acttccaagg tatggtgagc aagggcgagg agctgttcac    3480
cggggtggtg cccatcctgg tcgagctgga cggcgacgta aacggccaca agttcagcgt    3540
gtccggcgag ggcgagggcg atgccaccta cggcaagctg accctgaagt tcatctgcac    3600
caccggcaag ctgcccgtgc cctggcccac cctcgtgacc accctgacct acggcgtgca    3660
gtgcttcagc cgctaccccg accacatgaa gcagcacgac ttcttcaagt ccgccatgcc    3720
cgaaggctac gtccaggagc gcaccatctt cttcaaggac gacggcaact acaagacccg    3780
cgccgaggtg aagttcgagg gcgacaccct ggtgaaccgc atcgagctga agggcatcga    3840
cttcaaggag gacggcaaca tcctggggca caagctggag tacaactaca acagccacaa    3900
cgtctatatc atggccgaca agcagaagaa cggcatcaag gtgaacttca gatccgcca    3960
caacatcgag gacggcagcg tgcagctcgc cgaccactac cagcagaaca cccccatcgg    4020
```

```
cgacggcccc gtgctgctgc ccgacaacca ctacctgagc acccagtccg ccctgagcaa    4080
agacccaac  gagaagcgcg atcacatggt cctgctggag ttcgtgaccg ccgccgggat    4140
cactctcggc atggacgagc tgtacaagac cactgcgtgc gaaaacctgt acttccaagg    4200
tatggtgagc aagggcgagg agctgttcac cggggtggtg cccatcctgg tcgagctgga    4260
cggcgacgta acggccaca  agttcagcgt gtccggcgag ggcgagggcg atgccaccta    4320
cggcaagctg accctgaagt tcatctgcac caccggcaag ctgcccgtgc cctggcccac    4380
cctcgtgacc accctgacct acggcgtgca gtgcttcagc cgctaccccg accacatgaa    4440
gcagcacgac ttcttcaagt ccgccatgcc cgaaggctac gtccaggagc gcaccatctt    4500
cttcaaggac gacggcaact acaagacccg cgccgaggtg aagttcgagg gcgacaccct    4560
ggtgaaccgc atcgagctga agggcatcga cttcaaggag gacggcaaca tcctggggca    4620
caagctggag tacaactaca acagccacaa cgtctatatc atggccgaca agcagaagaa    4680
cggcatcaag gtgaacttca gatccgcca  caacatcgag gacggcagcg tgcagctcgc    4740
cgaccactac cagcagaaca cccccatcgg cgacggcccc gtgctgctgc ccgacaacca    4800
ctacctgagc acccagtccg ccctgagcaa agacccaac  gagaagcgcg atcacatggt    4860
cctgctggag ttcgtgaccg ccgccgggat cactctcggc atggacgagc tgtacaaggt    4920
cactacgtgt gaaaacctgt acttccaagg tatggtgagc aagggcgagg agctgttcac    4980
cggggtggtg cccatcctgg tcgagctgga cggcgacgta acggccaca  agttcagcgt    5040
gtccggcgag ggcgagggcg atgccaccta cggcaagctg accctgaagt tcatctgcac    5100
caccggcaag ctgcccgtgc cctggcccac cctcgtgacc accctgacct acggcgtgca    5160
gtgcttcagc cgctaccccg accacatgaa gcagcacgac ttcttcaagt ccgccatgcc    5220
cgaaggctac gtccaggagc gcaccatctt cttcaaggac gacggcaact acaagacccg    5280
cgccgaggtg aagttcgagg gcgacaccct ggtgaaccgc atcgagctga agggcatcga    5340
cttcaaggag gacggcaaca tcctggggca caagctggag tacaactaca acagccacaa    5400
cgtctatatc atggccgaca agcagaagaa cggcatcaag gtgaacttca gatccgcca     5460
caacatcgag gacggcagcg tgcagctcgc cgaccactac cagcagaaca cccccatcgg    5520
cgacggcccc gtgctgctgc ccgacaacca ctacctgagc acccagtccg ccctgagcaa    5580
agacccaac  gagaagcgcg atcacatggt cctgctggag ttcgtgaccg ccgccgggat    5640
cactctcggc atggacgagc tgtacaagac cacttcgtgc gaaaacctgt acttccaagg    5700
tatggtgagc aagggcgagg agctgttcac cggggtggtg cccatcctgg tcgagctgga    5760
cggcgacgta acggccaca  agttcagcgt gtccggcgag ggcgagggcg atgccaccta    5820
cggcaagctg accctgaagt tcatctgcac caccggcaag ctgcccgtgc cctggcccac    5880
cctcgtgacc accctgacct acggcgtgca gtgcttcagc cgctaccccg accacatgaa    5940
gcagcacgac ttcttcaagt ccgccatgcc cgaaggctac gtccaggagc gcaccatctt    6000
cttcaaggac gacggcaact acaagacccg cgccgaggtg aagttcgagg gcgacaccct    6060
ggtgaaccgc atcgagctga agggcatcga cttcaaggag gacggcaaca tcctggggca    6120
caagctggag tacaactaca acagccacaa cgtctatatc atggccgaca agcagaagaa    6180
cggcatcaag gtgaacttca gatccgcca  caacatcgag gacggcagcg tgcagctcgc    6240
cgaccactac cagcagaaca cccccatcgg cgacggcccc gtgctgctgc ccgacaacca    6300
ctacctgagc acccagtccg ccctgagcaa agacccaac  gagaagcgcg atcacatggt    6360
cctgctggag ttcgtgaccg ccgccgggat cactctcggc atggacgagc tgtacaagga    6420
```

```
aaacctgtac ttccaaagtg gagaaagctt gtttaaggga ccacgtgatt acaacccgat    6480
atcgagcacc atttgtcatt tgacgaatga atctgatggg cacacaacat cgttgtatgg    6540
tattggattt ggtcccttca tcattacaaa caagcacttg tttagaagaa ataatggaac    6600
actgttggtc caatcactac atggtgtatt caaggtcaag aacaccacga ctttgcaaca    6660
acacctcatt gatgggaggg acatgataat tattcgcatg cctaaggatt tcccaccatt    6720
tcctcaaaag ctgaaattta gagagccaca aagggaagag cgcatatgtc ttgtgacaac    6780
caacttccaa actaagagca tgtctagcat ggtgtcagac actagttgca cattcccttc    6840
atctgatggc atattctgga agcattggat tcaaaccaag gatgggcagt gtggcagtcc    6900
attagtatca actagagatg ggttcattgt tggtatacac tcagcatcga atttcaccaa    6960
cacaaacaat tatttcacaa gcgtgccgaa aaacttcatg gaattgttga caatcagga    7020 ggcgcagcag tgggttagtg gttggcgatt aaatgctgac tcagtattgt ggggggcca    7080 taaagttttc atgagcaaac ctgaagagcc ttttcagcca gttaaggaag cgactcaact    7140
catgaatgaa ttggtgtact cgcaagaaaa cctgtacttc caaagtatgc atagatcacg    7200
agatatcagc catggcttcc cgccggcggt ggcggcgcag gatgatggca cgctgcccat    7260
gtcttgtgcc caggagagcg ggatggaccg tcaccctgca gcctgtgctt ctgctaggat    7320
caatgtggag ctcgtgcacc tgactcctga ggagaagtct gccgttactg ccctgtgggg    7380
caaggtgaac gtggatgaag ttggtggtga ggccctgggc aggctgctgg tggtctaccc    7440
ttggacccag aggttctttg agtcctttgg ggatctgtcc actcctgatg ctgttatggg    7500
caaccctaag gtgaaggctc atggcaagaa agtgctcggt gcctttagtg atggcctggc    7560
tcacctggac aacctcaagg gcaccttgc cacactgagt gagctgcact gtgacaagct    7620
gcacgtggat cctgagaact tcagggtgag tctatgggac ccttgatgtt tctttcccc    7680 ttcttttcta tggttaagtt catgtcatag aaggggata agtaacaggg tacagtttag    7740
aatgggaaac agacgaatga ttgcatcagt gtggaagtct caggatcgtt ttagtttctt    7800
ttatttgctg ttcataacaa ttgttttctt ttgtttaatt cttgctttct ttttttttct    7860
tctccgcaat ttttactatt atacttaatg ccttaacatt gtgtataaca aaaggaaata    7920
tctctgagat acattaagta acttaaaaaa aaaactttac acagtctgcc tagtacatta    7980
ctatttggaa tatatgtgtg cttatttgca tattcataat ctccctactt tattttcttt    8040
tatttttaat tgatacataa tcattataca tatttatggg ttaaagtgta atgttttaat    8100
atgtgtacac atattgacca aatcagggta attttgcatt tgtaatttta aaaatgctt    8160 tcttcttttta atatactttt ttgtttatct tatttctaat actttcccta atctctttct    8220
ttcagggcaa taatgataca atgtatcatg cctctttgca ccattctaaa gaataacagt    8280
gataatttct gggttaaggc aatagcaata tttctgcata taaatatttc tgcatataaa    8340
ttgtaactga tgtaagaggt ttcatattgc taatagcagc tacaatccag ctaccattct    8400
gcttttattt tatggttggg ataaggctgg attattctga gtccaagcta ggcccttttg    8460
ctaatcatgt tcatacctct tatcttcctc ccacagctcc tgggcaacgt gctggtctgt    8520
gtgctggccc atcactttgg caagaattc accccaccag tgcaggctgc ctatcagaaa    8580
gtggtggctg gtgtggctaa tgccctggcc cacaagtatc actaagcggc cgctcgcttt    8640
cttgctgtcc aatttctatt aaaggttcct tgttccccta agtccaacta ctaaactggg    8700
ggatattatg aagggcctcg aggctgatca gcctcgactg tgccttctag ttgccagcca    8760
```

```
tctgttgttt gccccteccc cgtgccttcc ttgaccctgg aaggtgccac tcccactgtc    8820
ctttcctaat aaaatgagga aattgcatcg cattgtctga gtaggtgtca ttctattctg    8880
gggggtgggg tggggcagga cagcaagggg gaggattggg aagacaatag caggcatgct    8940
ggggatgcgg tgggctctat ggcttctgag gcggaaagaa ccagctgggg ctctaggggg    9000
tatccccacg cgccctgtag cggcgcatta agcgcggcgg gtgtggtggt tacgcgcagc    9060
gtgaccgcta cacttgccag cgccctagcg cccgctcctt tcgctttctt cccttcattt    9120
ctcgccacgt tcgccggctt tccccgtcaa gctctaaatc gggggctccc tttagggttc    9180
cgatttagtg ctttacggca cctcgacccc aaaaaacttg attagggtga tggttcacgt    9240
aggtacgcta gcaccgttgg tttccgtagt gtagtggtta tcacgttcgc ctaacacgcg    9300
aaaggtcccc ggttcgaaac cgggcactac aaaccaacaa cgctggtacc cctagaagtt    9360
cctattccga agttcctatt ctctagaaag tataggaact tccttggcca aaaagcctga    9420
aagatcacga gatatcagcc atggcttccc gccggcggtg gcggcgcagg atgatggcac    9480
gctgcccacg tcttgtgccc aggagagcgg gacgaccgt cacactgcag cctgtgcttc    9540
tgctaggatc aatgtggaaa acctgtactt ccaaggtacc gagtacaagc ccacggtgcg    9600
cctcgccacc cgcgacgacg tccccagggc cgtccgcacc ctcgccgccg cgttcgccga    9660
ctaccccgcc acgcgccaca ccgtcgatcc ggaccgccac atcgagcggg tcaccgagct    9720
gcaagaactc ttcctcacgc gcgtcgggct cgacatcggc aaggtgtggg tcgcggacga    9780
cggcgccgcg gtggcggtct ggaccacgcc ggagagcgtc gaagcggggg cggtgttcgc    9840
cgagatcggc ccgcgcatgg ccgagttgag cggttcccgg ctggccgcgc agcaacagat    9900
ggaaggcctc ctggcgccgc accggcccaa ggagcccgcg tggttcctgg ccaccgtcgg    9960
cgtctcgccc gaccaccagg gcaagggtct ggcagcgcc gtcgtgctcc ccggagtgga    10020
ggcggccgag cgcgccgggg tgcccgcctt cctggagacc tccgcgcccc gcaacctccc    10080
cttctacgag cggctcggct tcaccgtcac cgccgacgtc gaggtgcccg aaggaccgcg    10140
cacctggtgc atgacccgca agcccggtgc ctgaggtacc gctcgctgat cagcctcgac    10200 tgtgcctttct agttgccagc catctgttgt ttgcccctcc ccgtgccttt ccttgaccct    10260
ggaaggtgcc actcccactg tcctttccta ataaaatgag gaaattgcat cgcattgtct    10320
gagtaggtgt cattctattc tggggggtgg ggtggggcag gacagcaagg gggaggattg    10380
ggaagacaat agcaggcatg ctggggagtc gacaggtggc acttttcggg gaaatgtgcg    10440
cggaacccct atttgtttat ttttctaaat acattcaaat atgtatccgc tcatgagaca    10500
ataaccctga taaatgcttc aataatattg aaaaaggaag agtatgagta ttcaacattt    10560
ccgtgtcgcc cttattccct tttttgcggc attttgcctt cctgttttg ctcacccaga    10620 aacgctggtg aaagtaaaag atgctgaaga tcagttgggt gcacgagtgg gttacatcga    10680
actggatctc aacagcggta agatccttga gagttttcgc cccgaagaac gttttccaat    10740
gatgagcact tttaaagttc tgctatgtgg cgcggtatta tcccgtattg acgccgggca    10800
agagcaactc ggtcgccgca tacactattc tcagaatgac ttggttgagt actcaccagt    10860
cacagaaaag catcttacgg atggcatgac agtaagagaa ttatgcagtg ctgccataac    10920
catgagtgat aacactgcgg ccaacttact tctgacaacg atcggaggac cgaaggagct    10980
aaccgctttt ttgcacaaca tgggggatca tgtaactcgc cttgatcgtt gggaaccgga    11040
gctgaatgaa gccataccaa acgacgagcg tgacaccacg atgcctgtag caatggcaac    11100
aacgttgcgc aaactattaa ctggcgaact acttactcta gcttcccggc aacaattaat    11160
```

```
agactggatg gaggcggata aagttgcagg accacttctg cgctcggccc ttccggctgg    11220
ctggtttatt gctgataaat ctggagccgg tgagcgtggg tctcgcggta tcattgcagc    11280
actggggcca gatggtaagc cctcccgtat cgtagttatc tacacgacgg ggagtcaggc    11340
aactatggat gaacgaaata gacagatcgc tgagataggt gcctcactga ttaagcattg    11400
gtaactgtca gaccaagttt actcatatat actttagatt gatttaaa               11448
```

<210> SEQ ID NO 5
<211> LENGTH: 11448
<212> TYPE: DNA
<213> ORGANISM: Artificial Sequence
<220> FEATURE:
<223> OTHER INFORMATION: AVA2600[GFP(PTC+) PuromycinR] vector sequence

<400> SEQUENCE: 5

```
acttcatttt taatttaaaa ggatctaggt gaagatcctt tttgataatc tcatgaccaa      60
aatcccttaa cgtgagtttt cgttccactg agcgtcagac cccgtagaaa agatcaaagg     120
atcttcttga tccttttttt ttctgcgcgt aatctgctgc ttgcaaacaa aaaaaccacc     180
gctaccagcg gtggtttgtt tgccggatca agagctacca actctttttc cgaaggtaac     240
tggcttcagc agagcgcaga taccaaatac tgtccttcta gtgtagccgt agttaggcca     300
ccacttcaag aactctgtag caccgcctac atacctcgct ctgctaatcc tgttaccagt     360
ggctgctgcc agtggcgata gtcgtgtct taccgggttg gactcaagac gatagttacc     420
ggataaggcg cagcggtcgg gctgaacggg gggttcgtgc acacagccca gcttggagcg     480
aacgacctac accgaactga gatacctaca gcgtgagcta tgagaaagcg ccacgcttcc     540
cgaagggaga aaggcggaca ggtatccggt aagcggcagg gtcggaacag gagagcgcac     600
gagggagctt ccagggggaa acgcctggta tctttatagt cctgtcgggt ttcgccacct     660
ctgacttgag cgtcgatttt tgtgatgctc gtcaggggg cggagcctat ggaaaaacgc     720
cagcaacgcg gccttttttac ggttcctggc cttttgctgg ccttttgctc acatgttctt     780
tcctgcgtta tcccctgatt ctgtggataa ccgtattacc gcctttgagt gagctgatac     840
cgctcgccgc agccgaacga ccgagcgcag cgagtcagtg agcgaggaag cggaagagcg     900
cccaatacgc aaaccgcctc tccccgcgcg ttggccgatt cattaatgca gctggcacga     960
caggtttccc gactggaaag cgggcagtga gcgcaacgca attaatgtga gttagctcac    1020
tcattaggca ccccaggcac gcgaagcgtt gttggtttgt agtgcccggt tcgaaccgg     1080 ggaccttcg cgtgttaggc gaacgtgata accactacac tacggaaacc aacggtgcta    1140
gacgcgtatt gtctattctg actcggatcc gtacgaattc tcatgtttga cagcttatca    1200
tcgattagct ttggagctaa gccagcaatg gtagagggaa gattctgcac gtcccttcca    1260
ggcggcctcc ccgtcaccac cccccccaac ccgccccgac cggagctgag agtaattcat    1320
acaaaaggac tcgcccctgc cttggggaat cccaggaccc gtcgttaaaac tcccactaac    1380 gtagaaccca gagatcgctg cgttcccgcc ccctcacccg cccgctctcg tcatcactga    1440
ggtggagaag agcatgcgtg aggctccggt gcccgtcagt gggcagagcg cacatcgccc    1500
acagtccccg agaagttggg gggaggggtc ggcaattgaa ccggtgccta gagaaagtgg    1560
cgcggggtaa actgggaaag tgatgtcgtg tactggctcc gcctttttcc cgagggtggg    1620
ggagaaccgt atataagtgc agtagtcgcc gtgaacgttc ttttttcgcaa cgggtttgcc    1680 gccagaacac aggtaagtgc cgtgtgtggt tcccgcgggc ctggcctctt tacgggttat    1740
```

```
ggcccttgcg tgccttgaat tacttccacg ccctggctg cagtacgtga ttcttgatcc    1800
cgagcttcgg gttggaagtg ggtgggagag ttcgaggcct tgcgcttaag gagcccttc    1860
gcctcgtgct tgagttgagg cctggcctgg gcgctggggc cgccgcgtgc gaatctggtg   1920
gcaccttcgc gcctgtctcg ctgctttcga taagtctcta gccatttaaa attttgatg   1980
acctgctgcg acgcttttt tctggcaaga tagtcttgta aatgcgggcc aagatctgca    2040
cactggtatt tcggtttttg gggccgcggg cggcgacggg gcccgtgcgt cccagcgcac   2100
atgttcggcg aggcggggcc tgcgagcgcg gccaccgaga atcggacggg ggtagtctca   2160
agctggccgg cctgctctgg tgcctggcct cgcgccgccg tgtatcgccc cgccctgggc   2220
ggcaacaggc tggcccggtc ggcaccagtt gcgtgagcgg aaagatggcc gcttcccggc   2280
cctgctgcag ggagctcaaa atggaggacg cggcgctcgg gagagcgggc gggtgagtca   2340
cccacacaaa ggaaaagggc cttccgtcc tcagccgtcg cttcatgtga ctccacggag    2400
taccgggcgc cgtccaggca cctcgattag ttctcgagct tttggagtac gtcgtcttta   2460
ggttgggggg agggttttta tgcgatggag tttccccaca ctgagtgggt ggagactgaa   2520
gttaggccag cttggcactt gatgtaattc tccttggaat ttgcccttt tgagtttgga    2580
tcttggttca ttctcaagcc tcagacagtg gttcaaagtt tttttcttcc atttcaggtg   2640
tcgtgaaaac tctagcgttt ccgctctaga actagtccag ctagcgctac cggtcgccac   2700
catggtgagc aagggcgagg agctgttcac cggggtggtg cccatcctgg tcgagctgga   2760
cggcgacgta acggccaca agttcagcgt gtccggcgag ggcgagggcg atgccaccta    2820
cggcaagctg accctgaagt tcatctgcac caccggcaag ctgcccgtgc cctggcccac   2880
cctcgtgacc accctgacct acggcgtgca gtgcttcagc cgctacccg accacatgaa    2940
gcagcacgac ttcttcaagt ccgccatgcc cgaaggctac gtccaggagc gcaccatctt   3000
cttcaaggac gacggcaact acaagacccg cgccgaggtg aagttcgagg gcgacaccct   3060
ggtgaaccgc atcgagctga agggcatcga cttcaaggag gacggcaaca tcctggggca   3120
caagctggag tacaactaca acagccacaa cgtctatatc atggccgaca agcagaagaa   3180
cggcatcaag gtgaacttca agatccgcca caacatcgag gacggcagcg tgcagctcgc   3240
cgaccactac cagcagaaca ccccatcgg cgacggcccc gtgctgctgc ccgacaacca    3300
ctacctgagc acccagtccg ccctgagcaa agacccaac gagaagcgcg atcacatggt    3360
cctgctggag ttcgtgaccg ccgccgggat cactctcggc atggacgagc tgtacaaggt   3420
cactccgtgt gaaaacctgt acttccaagg tatggtgagc aagggcgagg agctgttcac   3480
cggggtggtg cccatcctgg tcgagctgga cggcgacgta acggccaca agttcagcgt    3540
gtccggcgag ggcgagggcg atgccaccta cggcaagctg accctgaagt tcatctgcac   3600
caccggcaag ctgcccgtgc cctggcccac cctcgtgacc accctgacct acggcgtgca   3660
gtgcttcagc cgctacccg accacatgaa gcagcacgac ttcttcaagt ccgccatgcc    3720
cgaaggctac gtccaggagc gcaccatctt cttcaaggac gacggcaact acaagacccg   3780
cgccgaggtg aagttcgagg gcgacaccct ggtgaaccgc atcgagctga agggcatcga   3840
cttcaaggag gacggcaaca tcctggggca caagctggag tacaactaca acagccacaa   3900
cgtctatatc atggccgaca agcagaagaa cggcatcaag gtgaacttca agatccgcca   3960
caacatcgag gacggcagcg tgcagctcgc cgaccactac cagcagaaca ccccatcgg    4020
cgacggcccc gtgctgctgc ccgacaacca ctacctgagc acccagtccg ccctgagcaa   4080
agacccaac gagaagcgcg atcacatggt cctgctggag ttcgtgaccg ccgccgggat    4140
```

```
cactctcggc atggacgagc tgtacaagac cactgcgtgc gaaaacctgt acttccaagg    4200
tatggtgagc aagggcgagg agctgttcac cggggtggtg cccatcctgg tcgagctgga    4260
cggcgacgta aacggccaca gtttcagcgt gtccggcgag ggcgagggcg atgccaccta    4320
cggcaagctg accctgaagt tcatctgcac caccggcaag ctgcccgtgc cctggcccac    4380
cctcgtgacc accctgacct acggcgtgca gtgcttcagc cgctacccg  accacatgaa    4440 gcagcacgac ttcttcaagt ccgccatgcc cgaaggctac gtccaggagc gcaccatctt    4500
cttcaaggac gacggcaact acaagacccg cgccgaggtg aagttcgagg gcgacaccct    4560
ggtgaaccgc atcgagctga agggcatcga cttcaaggag gacggcaaca tcctggggca    4620
caagctggag tacaactaca acagccacaa cgtctatatc atggccgaca agcagaagaa    4680
cggcatcaag gtgaacttca agatccgcca caacatcgag gacggcagcg tgcagctcgc    4740
cgaccactac cagcagaaca cccccatcgg cgacggcccc gtgctgctgc ccgacaacca    4800
ctacctgagc acccagtccg ccctgagcaa agaccccaac gagaagcgcg atcacatggt    4860
cctgctggag ttcgtgaccg ccgccgggat cactctcggc atggacgagc tgtacaaggt    4920
cactacgtgt gaaaacctgt acttccaagg tatggtgagc aagggcgagg agctgttcac    4980
cggggtggtg cccatcctgg tcgagctgga cggcgacgta aacggccaca gtttcagcgt    5040
gtccggcgag ggcgagggcg atgccaccta cggcaagctg accctgaagt tcatctgcac    5100
caccggcaag ctgcccgtgc cctggcccac cctcgtgacc accctgacct acggcgtgca    5160
gtgcttcagc cgctacccg  accacatgaa gcagcacgac ttcttcaagt ccgccatgcc    5220
cgaaggctac gtccaggagc gcaccatctt cttcaaggac gacggcaact acaagacccg    5280
cgccgaggtg aagttcgagg gcgacaccct ggtgaaccgc atcgagctga agggcatcga    5340
cttcaaggag gacggcaaca tcctggggca caagctggag tacaactaca acagccacaa    5400
cgtctatatc atggccgaca agcagaagaa cggcatcaag gtgaacttca agatccgcca    5460
caacatcgag gacggcagcg tgcagctcgc cgaccactac cagcagaaca cccccatcgg    5520
cgacggcccc gtgctgctgc ccgacaacca ctacctgagc acccagtccg ccctgagcaa    5580
agaccccaac gagaagcgcg atcacatggt cctgctggag ttcgtgaccg ccgccgggat    5640
cactctcggc atggacgagc tgtacaagac cacttcgtgc gaaaacctgt acttccaagg    5700
tatggtgagc aagggcgagg agctgttcac cggggtggtg cccatcctgg tcgagctgga    5760
cggcgacgta aacggccaca gtttcagcgt gtccggcgag ggcgagggcg atgccaccta    5820
cggcaagctg accctgaagt tcatctgcac caccggcaag ctgcccgtgc cctggcccac    5880
cctcgtgacc accctgacct acggcgtgca gtgcttcagc cgctacccg  accacatgaa    5940 gcagcacgac ttcttcaagt ccgccatgcc cgaaggctac gtccaggagc gcaccatctt    6000
cttcaaggac gacggcaact acaagacccg cgccgaggtg aagttcgagg gcgacaccct    6060
ggtgaaccgc atcgagctga agggcatcga cttcaaggag gacggcaaca tcctggggca    6120
caagctggag tacaactaca acagccacaa cgtctatatc atggccgaca agcagaagaa    6180
cggcatcaag gtgaacttca agatccgcca caacatcgag gacggcagcg tgcagctcgc    6240
cgaccactac cagcagaaca cccccatcgg cgacggcccc gtgctgctgc ccgacaacca    6300
ctacctgagc acccagtccg ccctgagcaa agaccccaac gagaagcgcg atcacatggt    6360
cctgctggag ttcgtgaccg ccgccgggat cactctcggc atggacgagc tgtacaagga    6420
aaacctgtac ttccaaagtg gagaaagctt gtttaaggga ccacgtgatt acaacccgat    6480
```

```
atcgagcacc atttgtcatt tgacgaatga atctgatggg cacacaacat cgttgtatgg    6540
tattggattt ggtcccttca tcattacaaa caagcacttg tttagaagaa ataatggaac    6600
actgttggtc caatcactac atggtgtatt caaggtcaag aacaccacga ctttgcaaca    6660
acacctcatt gatgggaggg acatgataat tattcgcatg cctaaggatt tcccaccatt    6720
tcctcaaaag ctgaaattta gagagccaca aagggaagag cgcatatgtc ttgtgacaac    6780
caacttccaa actaagagca tgtctagcat ggtgtcagac actagttgca cattcccttc    6840
atctgatggc atattctgga agcattggat tcaaaccaag gatgggcagt gtggcagtcc    6900
attagtatca actagagatg ggttcattgt tggtatacac tcagcatcga atttcaccaa    6960
cacaaacaat tatttcacaa gcgtgccgaa aaacttcatg gaattgttga caaatcagga    7020
ggcgcagcag tgggttagtg gttggcgatt aaatgctgac tcagtattgt gggggggcca    7080
taaagttttc atgagcaaac ctgaagagcc ttttcagcca gttaaggaag cgactcaact    7140
catgaatgaa ttggtgtact cgcaagaaaa cctgtacttc caaagtatgc atagatcacg    7200
agatatcagc catggcttcc cgccggcggt ggcggcgcag gatgatggca cgctgcccat    7260
gtcttgtgcc caggagagcg ggatggaccg tcaccctgca gcctgtgctt ctgctaggat    7320
caatgtggag ctcgtgcacc tgactcctga ggagaagtct gccgttactg ccctgtgggg    7380
caaggtgaac gtggatgaag ttggtggtga ggccctgggc aggctgctgg tggtctaccc    7440
ttggacctag aggttctttg agtcctttgg ggatctgtcc actcctgatg ctgttatggg    7500
caaccctaag gtgaaggctc atggcaagaa agtgctcggt gcctttagtg atggcctggc    7560
tcacctggac aacctcaagg gcaccttgc cacactgagt gagctgcact gtgacaagct    7620
gcacgtggat cctgagaact caggtgag tctatgggac ccttgatgtt tctttcccc     7680 ttctttccta tggttaagtt catgtcatag aagggata agtaacaggg tacagtttag    7740
aatgggaaac agacgaatga ttgcatcagt gtggaagtct caggatcgtt ttagtttctt    7800
ttatttgctg ttcataacaa ttgttttctt ttgtttaatt cttgctttct ttttttttct    7860
tctccgcaat ttttactatt atacttaatg ccttaacatt gtgtataaca aaaggaaata    7920
tctctgagat acattaagta acttaaaaaa aaaactttac acagtctgcc tagtacatta    7980
ctatttggaa tatatgtgtg cttatttgca tattcataat ctccctactt tattttcttt    8040 tattttaat tgatacataa tcattataca tatttatggg ttaaagtgta atgttttaat    8100
atgtgtacac atattgacca aatcagggta atttttgcatt tgtaatttta aaaaatgctt    8160 tcttcttta atatacttttt ttgttatct tattctaat actttcccta atctcttct     8220 ttcagggcaa taatgataca atgtatcatg cctctttgca ccattctaaa gaataacagt    8280
gataatttct gggttaaggc aatagcaata tttctgcata taaatatttc tgcatataaa    8340
ttgtaactga tgtaagaggt ttcatattgc taatagcagc tacaatccag ctaccattct    8400
gcttttattt tatggttggg ataaggctgg attattctga gtccaagcta ggccccttttg   8460 ctaatcatgt tcatacctct tatcttcctc ccacagctcc tgggcaacgt gctggtctgt    8520
gtgctggccc atcactttgg caaagaattc accccaccag tgcaggctgc ctatcagaaa    8580
gtggtggctg gtgtggctaa tgccctggcc cacaagtatc actaagcggc cgctcgcttt    8640
cttgctgtcc aatttctatt aaaggttcct ttgttcccta agtccaacta ctaaactggg    8700
ggatattatg aagggcctcg aggctgatca gcctcgactg tgccttctag ttgccagcca    8760
tctgttgttt gcccctcccc cgtgccttcc ttgaccctgg aaggtgccac tcccactgtc    8820
ctttcctaat aaaatgagga aattgcatcg cattgtctga gtaggtgtca ttctattctg    8880
```

```
gggggtgggg tggggcagga cagcaagggg gaggattggg aagacaatag caggcatgct    8940
ggggatgcgg tgggctctat ggcttctgag gcggaaagaa ccagctgggg ctctaggggg    9000
tatcccacg  cgccctgtag cggcgcatta agcgcggcgg gtgtggtggt tacgcgcagc    9060
gtgaccgcta cacttgccag cgccctagcg cccgctcctt tcgctttctt cccttccttt    9120
ctcgccacgt tcgccggctt tccccgtcaa gctctaaatc gggggctccc tttagggttc    9180
cgatttagtg ctttacggca cctcgacccc aaaaaacttg attagggtga tggttcacgt    9240
aggtacgcta gcaccgttgg tttccgtagt gtagtggtta tcacgttcgc ctaacacgcg    9300
aaaggtcccc ggttcgaaac cgggcactac aaaccaacaa cgctggtacc cctagaagtt    9360
cctattccga agttcctatt ctctagaaag tataggaact ccttggcca  aaaagcctga    9420
aagatcacga gatatcagcc atggcttccc gccggcggtg gcggcgcagg atgatggcac    9480
gctgcccacg tcttgtgccc aggagagcgg gacggaccgt caccctgcag cctgtgcttc    9540
tgctaggatc aatgtggaaa acctgtactt ccaaggtacc gagtacaagc ccacggtgcg    9600
cctcgccacc cgcgacgacg tccccagggc cgtccgcacc ctcgccgccg cgttcgccga    9660
ctaccccgcc acgcgccaca ccgtcgatcc ggaccgccac atcgagcggg tcaccgagct    9720
gcaagaactc ttcctcacgc gcgtcgggct cgacatcggc aaggtgtggg tcgcggacga    9780
cggcgccgcg gtggcggtct ggaccacgcc ggagagcgtc gaagcggggg cggtgttcgc    9840
cgagatcggc ccgcgcatgg ccgagttgag cggttcccgg ctggccgcgc agcaacagat    9900
ggaaggcctc ctggcgccgc accggcccaa ggagcccgcg tggttcctgg ccaccgtcgg    9960
cgtctcgccc gaccaccagg gcaagggtct gggcagcgcc gtcgtgctcc ccggagtgga   10020
ggcggccgag cgcgcggggg tgcccgcctt cctggagacc tccgcgcccc gcaacctccc   10080
cttctacgag cggctcggct tcaccgtcac cgccgacgtc gaggtgcccg aaggaccgcg   10140
cacctggtgc atgacccgca agcccggtgc ctgaggtacc gctcgctgat cagcctcgac   10200
tgtgccttct agttgccagc catctgttgt ttgcccctcc ccgtgcctt  ccttgaccct   10260
ggaaggtgcc actcccactg tcctttccta ataaaatgag gaaattgcat cgcattgtct   10320
gagtaggtgt cattctattc tggggggtgg ggtggggcag gacagcaagg gggaggattg   10380
ggaagacaat agcaggcatg ctggggagtc gacaggtggc acttttcggg gaaatgtgcg   10440
cggaacccct atttgtttat ttttctaaat acattcaaat atgtatccgc tcatgagaca   10500
ataaccctga taaatgcttc aataatattg aaaaaggaag agtatgagta ttcaacattt   10560
ccgtgtcgcc cttattccct ttttgcggc attttgcctt cctgttttg  ctcacccaga   10620
aacgctggtg aaagtaaaag atgctgaaga tcagttgggt gcacgagtgg gttacatcga   10680
actggatctc aacagcggta agatccttga gagttttcgc cccgaagaac gttttccaat   10740
gatgagcact tttaaagttc tgctatgtgg cgcggtatta tcccgtattg acgccgggca   10800
agagcaactc ggtcgccgca tacactattc tcagaatgac ttggttgagt actcaccagt   10860
cacagaaaag catcttacgg atggcatgac agtaagagaa ttatgcagtg ctgccataac   10920
catgagtgat aacactgcgg ccaacttact tctgacaacg atcggaggac cgaaggagct   10980
aaccgctttt ttgcacaaca tgggggatca tgtaactcgc cttgatcgtt gggaaccgga   11040
gctgaatgaa gccataccaa acgacgagcg tgacaccacg atgcctgtag caatggcaac   11100
aacgttgcgc aaactattaa ctggcgaact acttactcta gcttcccggc aacaattaat   11160
agactggatg gaggcggata aagttgcagg accacttctg cgctcggccc ttccggctgg   11220
```

```
ctggtttatt gctgataaat ctggagccgg tgagcgtggg tctcgcggta tcattgcagc   11280
actggggcca gatggtaagc cctcccgtat cgtagttatc tacacgacgg ggagtcaggc   11340
aactatggat gaacgaaata gacagatcgc tgagataggt gcctcactga ttaagcattg   11400
gtaactgtca gaccaagttt actcatatat actttagatt gatttaaa                11448
```

```
<210> SEQ ID NO 6
<211> LENGTH: 60
<212> TYPE: DNA
<213> ORGANISM: Artificial Sequence
<220> FEATURE:
<223> OTHER INFORMATION: Random priming forward primer

<400> SEQUENCE: 6
taacttgaaa gtatttcgat ttcttggctt tatatatctt gtggaaagga cgaaacaccg   60

<210> SEQ ID NO 7
<211> LENGTH: 60
<212> TYPE: DNA
<213> ORGANISM: Artificial Sequence
<220> FEATURE:
<223> OTHER INFORMATION: Random priming reverse primer

<400> SEQUENCE: 7 acttttcaa gttgataacg gactagcctt attttaactt gctatttcta gctctaaaac    60

<210> SEQ ID NO 8
<211> LENGTH: 59
<212> TYPE: DNA
<213> ORGANISM: Artificial Sequence
<220> FEATURE:
<223> OTHER INFORMATION: shRNA for RPS8 (sh22)

<400> SEQUENCE: 8
ccggccgtgc cctgaggttg gacgtctcga gacgtccaac ctcagggcac ggttttttg    59

<210> SEQ ID NO 9
<211> LENGTH: 59
<212> TYPE: DNA
<213> ORGANISM: Artificial Sequence
<220> FEATURE:
<223> OTHER INFORMATION: shRNA for AVEN (sh01)

<400> SEQUENCE: 9
ccgggacctg aaatccaagg aagatctcga gatcttcctt ggatttcagg tcttttttg    59

<210> SEQ ID NO 10
<211> LENGTH: 20
<212> TYPE: DNA
<213> ORGANISM: Artificial Sequence
<220> FEATURE:
<223> OTHER INFORMATION: sgRNA targeting UPF1

<400> SEQUENCE: 10
tgattacgtc ctccacctcg                                                20

<210> SEQ ID NO 11
<211> LENGTH: 20
<212> TYPE: DNA
<213> ORGANISM: Artificial Sequence
<220> FEATURE:
<223> OTHER INFORMATION: sgRNA targeting SMG7

<400> SEQUENCE: 11
aggtccactc accattggag                                                20
```

<210> SEQ ID NO 12
<211> LENGTH: 20
<212> TYPE: DNA
<213> ORGANISM: Artificial Sequence
<220> FEATURE:
<223> OTHER INFORMATION: sgRNA targeting SMG7

<400> SEQUENCE: 12
agtgtcctcc ttagctctgc                                            20

<210> SEQ ID NO 13
<211> LENGTH: 20
<212> TYPE: DNA
<213> ORGANISM: Artificial Sequence
<220> FEATURE:
<223> OTHER INFORMATION: sgRNA targeting AVEN

<400> SEQUENCE: 13
agtgtcctcc ttagctctgc                                            20

<210> SEQ ID NO 14
<211> LENGTH: 20
<212> TYPE: DNA
<213> ORGANISM: Artificial Sequence
<220> FEATURE:
<223> OTHER INFORMATION: sgRNA targeting SMG6

<400> SEQUENCE: 14
gttctctgat aatcagaatg                                            20

<210> SEQ ID NO 15
<211> LENGTH: 20
<212> TYPE: DNA
<213> ORGANISM: Artificial Sequence
<220> FEATURE:
<223> OTHER INFORMATION: sgRNA targeting SMG5

<400> SEQUENCE: 15
acgcacctgg ttgctggtat                                            20

<210> SEQ ID NO 16
<211> LENGTH: 20
<212> TYPE: DNA
<213> ORGANISM: Artificial Sequence
<220> FEATURE:
<223> OTHER INFORMATION: sgRNA targeting SMG6

<400> SEQUENCE: 16
ggatgaccaa gacgacatca                                            20

<210> SEQ ID NO 17
<211> LENGTH: 20
<212> TYPE: DNA
<213> ORGANISM: Artificial Sequence
<220> FEATURE:
<223> OTHER INFORMATION: sgRNA targeting SMG5

<400> SEQUENCE: 17
ctatgagggg gtcagtgaca                                            20

<210> SEQ ID NO 18
<211> LENGTH: 20
<212> TYPE: DNA
<213> ORGANISM: Artificial Sequence
<220> FEATURE:

<223> OTHER INFORMATION: sgRNA targeting YAE1D1

<400> SEQUENCE: 18
tgagcacata ctcttcacac                                               20

<210> SEQ ID NO 19
<211> LENGTH: 20
<212> TYPE: DNA
<213> ORGANISM: Artificial Sequence
<220> FEATURE:
<223> OTHER INFORMATION: sgRNA targeting EIF2B4

<400> SEQUENCE: 19
ccgtgacatc acagacccgt                                               20

<210> SEQ ID NO 20
<211> LENGTH: 20
<212> TYPE: DNA
<213> ORGANISM: Artificial Sequence
<220> FEATURE:
<223> OTHER INFORMATION: sgRNA targeting UPF1

<400> SEQUENCE: 20
cgcattgaaa acgtttgccg                                               20

<210> SEQ ID NO 21
<211> LENGTH: 20
<212> TYPE: DNA
<213> ORGANISM: Artificial Sequence
<220> FEATURE:
<223> OTHER INFORMATION: sgRNA targeting WDR55

<400> SEQUENCE: 21
ggtaccttca ctggagccac                                               20

<210> SEQ ID NO 22
<211> LENGTH: 20
<212> TYPE: DNA
<213> ORGANISM: Artificial Sequence
<220> FEATURE:
<223> OTHER INFORMATION: sgRNA targeting UPF2

<400> SEQUENCE: 22
tatgtcttac cagaagctgc                                               20

<210> SEQ ID NO 23
<211> LENGTH: 20
<212> TYPE: DNA
<213> ORGANISM: Artificial Sequence
<220> FEATURE:
<223> OTHER INFORMATION: sgRNA targeting SMG6

<400> SEQUENCE: 23
ctcaaccgat tccttagacg                                               20

<210> SEQ ID NO 24
<211> LENGTH: 20
<212> TYPE: DNA
<213> ORGANISM: Artificial Sequence
<220> FEATURE:
<223> OTHER INFORMATION: sgRNA targeting FARSB

<400> SEQUENCE: 24
tcacgcttca cgctgacagt                                               20

```
<210> SEQ ID NO 25
<211> LENGTH: 20
<212> TYPE: DNA
<213> ORGANISM: Artificial Sequence
<220> FEATURE:
<223> OTHER INFORMATION: sgRNA targeting ZNHIT6

<400> SEQUENCE: 25
tgctttgtgt ttctttacac                                                    20

<210> SEQ ID NO 26
<211> LENGTH: 20
<212> TYPE: DNA
<213> ORGANISM: Artificial Sequence
<220> FEATURE:
<223> OTHER INFORMATION: sgRNA targeting NOP58

<400> SEQUENCE: 26
ttagcatcag ctactgccag                                                    20

<210> SEQ ID NO 27
<211> LENGTH: 20
<212> TYPE: DNA
<213> ORGANISM: Artificial Sequence
<220> FEATURE:
<223> OTHER INFORMATION: sgRNA targeting SMG5

<400> SEQUENCE: 27
gaaagactga ggagctgctg                                                    20

<210> SEQ ID NO 28
<211> LENGTH: 20
<212> TYPE: DNA
<213> ORGANISM: Artificial Sequence
<220> FEATURE:
<223> OTHER INFORMATION: sgRNA targeting SPATA5

<400> SEQUENCE: 28
ttcaaactag taagcaacac                                                    20

<210> SEQ ID NO 29
<211> LENGTH: 20
<212> TYPE: DNA
<213> ORGANISM: Artificial Sequence
<220> FEATURE:
<223> OTHER INFORMATION: sgRNA targeting GAR1

<400> SEQUENCE: 29
taagttgtca gaaaacatga                                                    20

<210> SEQ ID NO 30
<211> LENGTH: 20
<212> TYPE: DNA
<213> ORGANISM: Artificial Sequence
<220> FEATURE:
<223> OTHER INFORMATION: sgRNA targeting SLMO2

<400> SEQUENCE: 30
tcacatcggc agccacccgt                                                    20

<210> SEQ ID NO 31
<211> LENGTH: 20
<212> TYPE: DNA
<213> ORGANISM: Artificial Sequence
<220> FEATURE:
<223> OTHER INFORMATION: sgRNA targeting RPS8
```

```
<400> SEQUENCE: 31
gcgcccagct gccaacacca                                                20

<210> SEQ ID NO 32
<211> LENGTH: 20
<212> TYPE: DNA
<213> ORGANISM: Artificial Sequence
<220> FEATURE:
<223> OTHER INFORMATION: sgRNA targeting EIF2B4

<400> SEQUENCE: 32
agcccataat gtaccagtgc                                                20

<210> SEQ ID NO 33
<211> LENGTH: 20
<212> TYPE: DNA
<213> ORGANISM: Artificial Sequence
<220> FEATURE:
<223> OTHER INFORMATION: sgRNA targeting SFI1

<400> SEQUENCE: 33
tacctatgtg cgtcagcagc                                                20
```

FLUORESCENCE AMPLIFICATION METHOD FOR FORWARD GENETIC DISCOVERY OF FACTORS IN HUMAN MRNA DEGRADATION

CROSS REFERENCE TO RELATED APPLICATIONS

This application claims priority to U.S. Provisional Application No. 62/438,205, filed Dec. 22, 2016 which is hereby incorporated by reference herein in its entirety.

STATEMENT REGARDING FEDERALLY SPONSORED RESEARCH OR DEVELOPMENT

This invention was made with government support under R01 GM026154 and R21 NS091637 awarded by the National Institutes of Health. The government has certain rights in the invention.

BACKGROUND OF THE INVENTION

With nearly 20% of human disease-associated single base pair substitutions forming a premature termination codon (PTC) (Mort et al., Hum Mutat 2008, 29:1037-1047), these lesions often have drastic clinical consequences. PTC mutations can result in severe human genetic diseases such as variants of Duchenne and Becker muscular dystrophies (dystrophin), retinoblastoma (RB1), neurofibromatosis (NF1, NF2), ataxia-telangiectasia (ATM), Tay-Sachs disease (HEXA), cystic fibrosis (CFTR), Wilm's tumor (WT1), beta thalassemia (betaglobin), hemophilia A (factor VIII) and B (factor IX), von Willebrand disease (Willebrand factor), p53-associated cancers (p53), and numerous others (Holbrook et al., Nat Genet 2004, 36, 801-808). There are no cures for these genetic disorders.

Experimental therapies for PTC-induced disorders, aminoglycosides (Gunn et al., Mol Genet Metab 2014, 111:374-381; Keeling et al., Annu Rev Genomics Hum Genet 2014, 15:371-394) and ataluren (PTC124) (Finkel et al., PLoS One 2013, 8:e81302; Kerem et al., Lancet Respir Med 2014, 2, 539-547; Roy et al., Proc Natl Acad Sci USA. 2016 113: 12508-12513), as well as a number of small molecules, e.g., RTC13 and RTC14 (Du et al., J Exp Med 2009, 206:2285-2297), GJO71 and GJ072 (Du et al., Mol Ther 2013, 21:1653-1660), and amlexanox (Gonzalez-Hilarion et al., Orphanet J Rare Dis 2012, 7:58), promote PTC readthrough. A growing body of evidence (Keeling et al., PLoS One 2013, 8:e60478; Keeling et al., Annu Rev Genomics Hum Genet 2014, 15:371-394; Martin et al., Cancer Res 2014, 74:3104-3113; Nomakuchi et al., Nat Biotechnol 2016, 34:164-166) suggests that successful therapies, in addition to promoting PTC readthrough, need to address degradation of PTC-containing mRNAs by the human nonsense-mediated decay (NMD) pathway (Kurosaki and Maquat, J Cell Sci 2016, 129:461-467). Because the NMD pathway reduces the levels of PTC-containing mRNA, inhibition of NMD increases the amount of PTC-containing mRNA available for readthrough, aiding in recovery of full-length protein product.

Not only does NMD play a prominent role in human disease, but it also serves as a major mRNA degradation pathway, regulating at least 10% of human mRNAs (Rehwinkel et al., RNA 2005, 11:1530-1544). NMD operates via the concerted action of multiple factors (Kurosaki and Maquat, J Cell Sci 2016, 129:461-467), many of which also function in other cellular processes. Knockdown of some of these factors (e.g. UPF1, UPF2, or SMG1) is embryonic lethal in mouse (McIlwain et al., Proc Natl Acad Sci USA 2010, 107:12186-12191; Medghalchi et al., Hum Mol Genet 2001, 10:99-105; Weischenfeldt et al., Genes Dev 2008, 22:1381-1396), whereas depletion of others, like SMG8, was found not to cause noticeable cell-growth defects (Usuki et al., Proc Natl Acad Sci USA 2013, 110: 15037-15042). Potential therapeutic inhibition of human NMD therefore must be carefully crafted to limit toxic/negative effects (Keeling et al., Annu Rev Genomics Hum Genet 2014, 15:371-394), requiring better understanding of the precise cellular roles of human NMD components and mechanisms of human-specific and, prospectively, tissue-specific NMD.

However, the full scope of factors comprising the human NMD pathway is not known, largely because of the lack of comprehensive genetic screens. Comprehensive forward genetic screens for NMD factors have been accomplished only in model organisms such as S. cerevisiae, C. elegans, and D. melanogaster (Hodgkin et al., Genetics 1989, 123: 301-313; Leeds et al., Genes Dev 1991, 5:2303-2314; Metzstein and Krasnow, PLoS Genet 2006, 2:e180) leading to identification of a number of human NMD factors by homology search (Perlick et al., Proc Natl Acad Sci USA 1996, 93:10928-10932). Yet, vertebrate NMD pathways appear to involve many vertebrate-specific factors (Lykke-Andersen and Jensen, Nat Rev Mol Cell Biol 2015, 16:665-677). For example, whereas the exon junction complex (EJC) is a major NMD player in mammals (Le Hir et al., Genes Dev 2000, 14:1098-1108), the yeast S. cerevisiae has no known EJC; moreover, NMD in yeast does not depend on splicing, and known EJC components in D. melanogaster and C. elegans are not required for NMD (Gatfield et al., EMBO J 2003, 22:3960-3970; Longman et al., Genes Dev 2007, 21:1075-1085). Therefore, screens in model (non-vertebrate) organisms are of only limited utility for identification of human-specific NMD components. No systematic forward genetic screen for human NMD factors has been successfully performed in human cells. Therefore, the list of human NMD factors is undefined, with important factors, such as hCWC22 (Alexandrov et al., Proc Natl Acad Sci USA 2012, 109:21313-21318; Barbosa et al., Nat Struct Mol Biol 2012, 19:983-990; Steckelberg et al., Cell Rep 2012, 2:454-461), MOV10 (Gregersen et al., Mol Cell 2014, 54:573-585), GNL2, and SEC13 (Casadio et al., EMBO Rep 2015, 16:71-78), being only recently identified.

There is thus a need in the art for methods to allow systematic forward genetic screening in humans to assist in identification of human-specific pathway components. The present invention addresses this unmet need in the art.

SUMMARY OF THE INVENTION

In one embodiment, the invention relates to a composition for amplifying a detectable signal comprising a nucleic acid molecule comprising a tandem reporter construct, wherein the tandem reporter construct comprises a single promoter operably linked to two or more tandem reporter genes for providing a detectable signal. In one embodiment, two or more tandem reporter genes comprise at least five tandem reporter genes.

In one embodiment, the two or more tandem reporter genes encode fluorescent proteins. In one embodiment, the two or more tandem reporter genes encode the same fluorescent protein. In one embodiment, the fluorescent protein is selected from the group consisting of EGFP and tdTomato. In one embodiment, the two or more tandem reporter genes encode multiple fluorescent proteins.

In one embodiment, the tandem reporter construct further comprises nucleic acid sequence encoding a cleavage site between each of the two or more tandem reporter genes. In one embodiment, the tandem reporter construct further comprises nucleic acid sequence encoding a protease. In one embodiment, the nucleic acid sequence encoding a protease comprises a sequence encoding an internal protease cleavage site. In one embodiment, the protease is tobacco etch virus (TEV) protease and the cleavage sites between each of the two or more tandem reporter genes and the internal cleavage site in the nucleotide sequence encoding the protease are TEV protease cleavage sites.

In one embodiment, the tandem reporter construct further comprises nucleic acid sequence encoding a polypeptide sequence containing a protein degradation sequence. In one embodiment, the tandem reporter construct further comprises nucleic acid sequence encoding a polypeptide sequence operably linked to a protein degradation sequence. In one embodiment, the protein degradation sequence is a PEST sequence.

In one embodiment, the invention relates to a composition for the elimination of negative effects of a fused polypeptide of interest (POI) on maturation, localization, and half-life of a reporter comprising a nucleic acid molecule comprising a tandem reporter construct, wherein the tandem reporter construct comprises a single promoter operably linked to two or more tandem reporter genes for providing a detectable signal and further operably linked to a POI, and wherein the tandem reporter construct comprises nucleic acid sequence encoding a cleavage site between each of the two or more tandem reporter genes and between any upstream nucleotide sequence and the sequence encoding the POI. In one embodiment, the tandem reporter construct further comprises nucleic acid sequence encoding a protease upstream of the POI. In one embodiment, the nucleic acid sequence encoding a protease comprises a sequence encoding an internal protease cleavage site. In one embodiment, the protease is tobacco etch virus (TEV) protease and wherein the cleavage sites between each of the two or more tandem reporter genes and the internal cleavage site in the nucleotide sequence encoding the protease are TEV protease cleavage sites.

In one embodiment, the POI comprises a nucleic acid sequence encoding a protein degradation sequence. In one embodiment, the POI is operably linked to a protein degradation sequence. In one embodiment, the protein degradation sequence is a PEST sequence.

In one embodiment, the nucleic acid molecule comprising a tandem reporter construct is a vector. In one embodiment, the vector has a nucleotide sequence selected from the group consisting of SEQ ID NO:2, SEQ ID NO:3, SEQ ID NO:4 and SEQ ID NO:5. In one embodiment, the vector is an expression vector. In one embodiment, the vector is a product of flippase recognition target (FRT) recombination of a nucleic acid molecule having a nucleotide sequence as set forth in SEQ ID NO:1 with a nucleic acid molecule comprising a tandem reporter construct.

In one embodiment, the invention relates to a cell comprising at least one tandem reporter construct, wherein the tandem reporter construct comprises a single promoter operably linked to two or more tandem reporter genes for providing a detectable signal. In one embodiment, the cell comprises two expression vectors comprising tandem reporter constructs.

In one embodiment, the first expression vector comprises a nucleotide sequence as set forth in SEQ ID NO:3, and wherein the second expression vector comprises a nucleotide sequence as set forth in SEQ ID NO:4.

In one embodiment, the cell is a Green Fireworks cell. In one embodiment, the first expression vector comprises a nucleotide sequence as set forth in SEQ ID NO:2, and wherein the second expression vector comprises a nucleotide sequence as set forth in SEQ ID NO:5. In one embodiment, the cell is a Red Fireworks cell.

In one embodiment, the invention relates to a method for screening for the effect of a treatment on a biological pathway comprising contacting a cell comprising at least one tandem reporter construct, wherein the tandem reporter construct comprises a single promoter operably linked to two or more tandem reporter genes for providing a detectable signal with the compound or treatment, and detecting expression of the reporter genes encoded by the tandem reporter construct. In one embodiment, the expression of the tandem reporter construct alters in response to the effect of a treatment on a biological pathway. In one embodiment, the expression of the two or more reporter genes encoded by the tandem reporter construct increases in response to the treatment. In one embodiment, the expression of the two or more reporter genes encoded by the tandem reporter construct decreases in response to the treatment.

In one embodiment, the invention relates to a method of screening for the effect of a treatment on the nonsense mediated mRNA decay (NMD) pathway comprising contacting a cell comprising two expression vectors comprising tandem reporter constructs, wherein the first expression vector comprises a nucleotide sequence as set forth in SEQ ID NO:3, and wherein the second expression vector comprises a nucleotide sequence as set forth in SEQ ID NO:4, with a treatment and detecting expression of the reporter genes encoded by the one or more tandem reporter constructs. In one embodiment, the expression of the reporter genes encoded by the tandem reporter constructs is detected using flow cytometry.

In one embodiment, the invention relates to a method of screening for the effect of a treatment on the NMD pathway comprising contacting a cell comprising two expression vectors comprising tandem reporter constructs, wherein the first expression vector comprises a nucleotide sequence as set forth in SEQ ID NO:2, and wherein the second expression vector comprises a nucleotide sequence as set forth in SEQ ID NO:5, with a treatment and detecting expression of the reporter genes encoded by the tandem reporter constructs. In one embodiment, the expression of the reporter genes encoded by the tandem reporter constructs is detected using flow cytometry.

In one embodiment, the invention relates to a method of screening for factors that alter mRNA stability comprising contacting a cell comprising at least one tandem reporter construct, wherein the tandem reporter construct comprises a single promoter operably linked to two or more tandem reporter genes for providing a detectable signal with a treatment and detecting expression of the reporter genes encoded by a tandem reporter construct. In one embodiment, the expression of the reporter genes encoded by the tandem reporter construct is detected using flow cytometry.

In one embodiment, the invention relates to a method of screening for components and regulators of pathways that modulate abundance of disease-associated human RNAs comprising contacting a cell comprising at least one tandem reporter construct, wherein the tandem reporter construct comprises a single promoter operably linked to two or more tandem reporter genes for providing a detectable signal with a treatment and detecting expression of the reporter genes encoded by a tandem reporter construct. In one embodiment, the expression of the reporter genes encoded by the tandem reporter constructs is detected using flow cytometry.

In one embodiment, the invention relates to a method of sgRNA enrichment for use in a method of CRISPR-based forward genetic screening comprising performing the steps of a) generating or obtaining pool of lentiviruses from a sgRNA library, b) transducing cells with the pool of lentiviruses to generate a pool of CRISPR-mutagenized cells, c) performing cell sorting, d) isolating genomic DNA from the sorted cells, e) performing polymerase chain reaction (PCR)-amplification to generate an sgRNA pool and f) generating a new sgRNA lentiviral library from the amplified sgRNA pool, with steps a) through f) being performed sequentially at least two times.

In one embodiment, step b) comprises transducing at least one cell comprising at least one tandem reporter construct, wherein the tandem reporter construct comprises a single promoter operably linked to two or more tandem reporter genes for providing a detectable signal with the pool of lentiviruses to generate a pool of CRISPR-mutagenized cells.

In one embodiment, step c) comprises performing fluorescence-associated cell sorting.

In one embodiment, the invention relates to a method of treating a disease or disorder associated with a premature termination codon (PTC) comprising administering an inhibitor of a protein involved in the NMD pathway to a subject in need thereof.

In one embodiment, a protein involved in the NMD pathway is selected from the group consisting of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 or SFI1.

In one embodiment, the disease or disorder is selected from the group consisting of Duchenne and Becker muscular dystrophies, retinoblastoma, neurofibromatosis, ataxia-telangiectasia, Tay-Sachs disease, cystic fibrosis, Wilm's tumor, hemophilia A, hemophilia B, p53-associated cancers, Menkes disease, Ullrich's disease, β-Thalassemia, type 2A and type 3 von Willebrand disease, Robinow syndrome, brachydactyly type B (shortening of digits and metacarpals), inherited susceptibility to mycobacterial infection, inherited retinal disease, inherited bleeding tendency, inherited blindness, congenital neurosensory deafness and colonic aganglionis.

BRIEF DESCRIPTION OF THE DRAWINGS

The following detailed description of preferred embodiments of the invention will be better understood when read in conjunction with the appended drawings. It should be understood, however, that the invention is not limited to the precise arrangements and instrumentalities of the embodiments shown in the drawings.

FIG. 2, comprising FIG. 2A depicts a schematic diagram of the Fireworks approach for the "green" Fireworks cell line. Each Fireworks reporter expresses a single polyprotein consisting of (1) 10 or 5 fluorescent proteins (FPs, e.g. RFP or GFP), (2) tobacco etch virus (TEV) protease, and (3) PEST-β-globin. The β-globin gene lacks the first intron and either carries or lacks a PTC (PTC39) upstream of its last (second) intron. The resulting polyprotein contains 7 TEV protease cleavage sites: (i) between each copy of fluorescent protein, (ii) between the last fluorescent protein and the protease, (iii) within the protease, and (iv) between the protease and the PEST-β-globin. As a result, in vivo translated FPs are separated from each other, the protease, and the PEST-β-globin through in vivo proteolytic cleavage. The PEST degradation sequence (Rogers et al., Science 1986, 234:364-368) was added to shorten the β-globin protein half-life. FIG. 2B depicts HeLa cells with genome-integrated Fireworks reporters produce strong fluorescence signals, which are above the calibration range of a FACS instrument. The fluorescence is stable, uniform, and virtually immune to silencing. Lower-right insert: Pellets of Fireworks cells at ambient lighting. FIG. 2C depicts the fluorescence of stable orthogonal Fireworks cell lines observed with an epifluorescence microscope. Each (HeLa) cell line carries two flippase recognition target (FRT)-integrated Fireworks reporters that differ by a single (PTC39) nucleotide: the cell line on the left carries PTC39 in the second exon of the β-globin sequence in the RFP-containing reporter; the cell line on the right carries the identical PTC39 in the GFP-containing reporter. mRNAs expressed by the PTC39-containing reporters are NMD substrates and yield lower fluorescence; mRNAs of the control Fireworks reporters are unaffected, producing the green (left lower panel) and red (right upper panel) signal. The brown color of the cells in the lower right panel results from the leakage of red color into the green channel. FIG. 2D depicts a flow cytometry analysis showing pools of HeLa cells with genome-integrated Fireworks reporters appropriately respond to the introduction of PTC39 by a 7- to 9-fold fluorescence drop (no attempt was made to fine-tune color compensation).

FIG. 3, comprising FIG. 3A through FIG. 3D, further depicts the Fireworks in vivo NMD reporter system.

FIG. 5, comprising FIG. 5A depicts NMD inhibition via expression of UPF1-targeting shRNA results in an 8-fold increase in red fluorescence of the Fireworks "green" cell line (shown in FIG. 2A and the left panel of FIG. 2C). FIG. 5B depicts NMD inhibition via expression of Cas9 and UPF1-targeting sgRNA causes a 4-fold increase in red fluorescence of the Fireworks "green" cell line. FIG. 5C depicts a schematic diagram of sgRNA library enrichment using FACS sorting of Fireworks cells. Importantly, sgRNA-specific effects are amplified, whereas cell-specific effects are reset at the beginning of each enrichment round. FIG. 5D depicts experimental results demonstrating that enrichment of sgRNAs that affect human NMD is evident after FACS sorting of the GeCKO-Lt-CRISPR sgRNA library transduced into "green" Fireworks cells. An increase in the NMD-defective cell population is seen in the blue gates after sequential rounds of enrichment (round 1: 0.21%, round 2: 0.56%, and round 3: 2.96% of total cells).

FIG. 6, comprising FIG. 6A depicts flow cytometry analyses demonstrating that sgRNAs obtained from the genome-wide screen (Table 1) were individually transduced into the "green" Fireworks cell line (FIG. 2A) and the resulting cells were FACS-analyzed for an increase in red fluorescence. Populations of cells with increased red fluorescence (nearly not observable [0.9-1.0%] in the corresponding negative controls) appear in the red gate. Fractions (percent) of cells in the original (black gates) and shifted (red gates) populations are indicated. FIG. 6B depicts flow cytometry analysis of genes not previously implicated in NMD. To exclude possible off-target effects of sgRNAs, two of the genes not previously implicated in NMD, AVEN and RPS8, were targeted by shRNAs. FACS-analyses of the shRNA-transduced "green" Fireworks cell line are shown; populations of cells with increased red fluorescence appear in the red gate (FACS-analysis of the orthogonal "red" Fireworks cell line transduced with shRNA targeting RPS8 is shown in FIG. 7B).

FIG. 7, comprising FIG. 7A depicts FACS analysis of "green" Fireworks cells transduced with individual sgRNAs obtained from the genome-wide screen (Table 1) was conducted as described in FIG. 6A and Experimental Procedures. FIG. 7B depicts flow cytometry experiments demonstrating that transduction of RPS8-targeting shRNA into the "red" Fireworks cell line results in an increase in green fluorescence. Populations of cells with increased green fluorescence are seen in the red gate.

DETAILED DESCRIPTION

Figure 1:
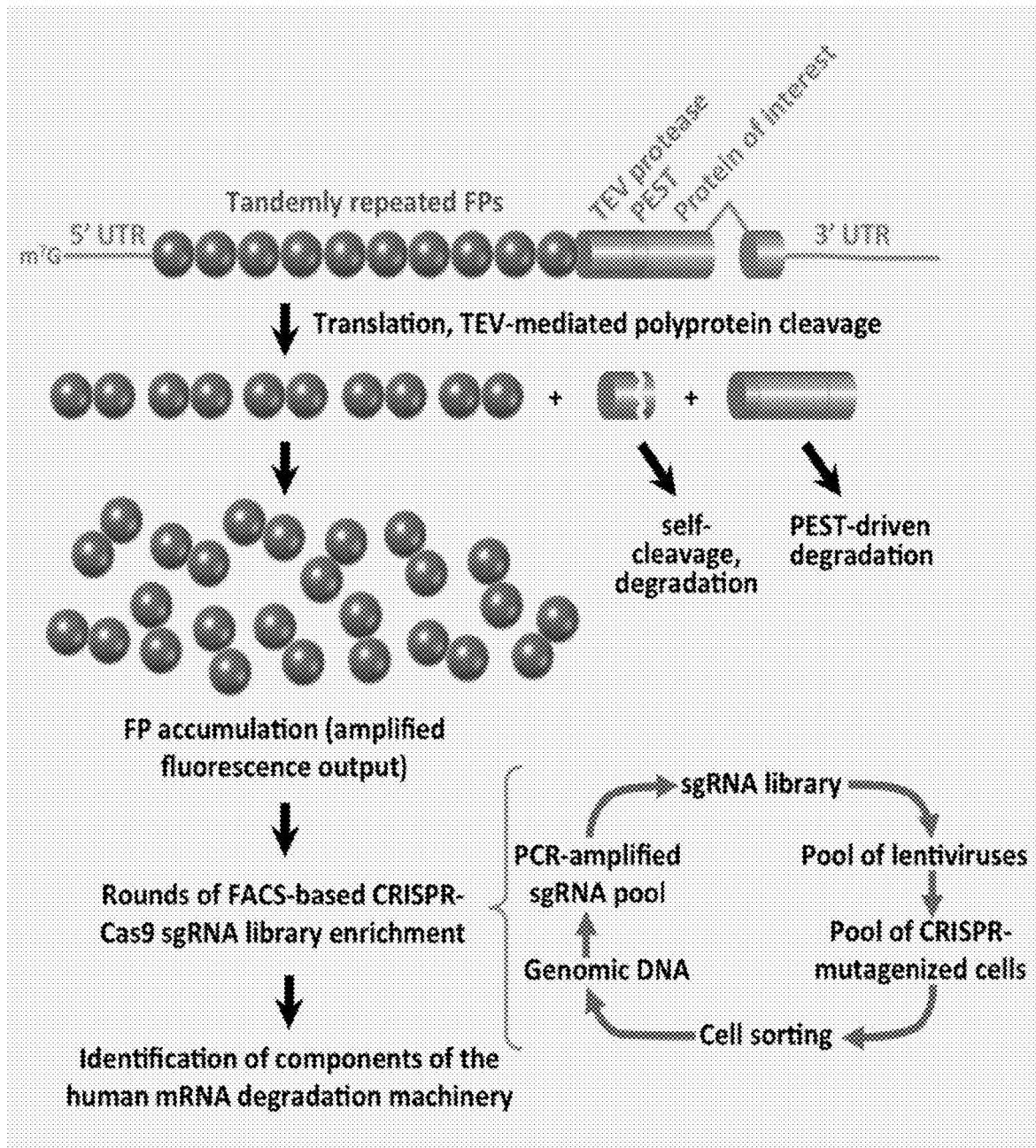
FIG. 1 depicts a flow chart showing a tandem reporter construct, amplification of the fluorescent signal generated using the tandem reporter construct, degradation of the protease and protein of interest following translation of multiple fluorescent proteins from the tandem reporter construct, and the use of the tandem reporter construct and multiple rounds of sgRNA enrichment in a CRISPR-based forward genetic screen.

The present invention relates generally to compositions and methods of amplifying a detectable signal through use of a tandem reporter construct having multiple tandem genes providing a detectable signal. In various embodiments, compositions of the invention include tandem reporter constructs, vectors carrying tandem reporter constructs, and cells modified with vectors carrying tandem reporter constructs. In various embodiments, the invention relates to methods of using tandem reporter constructs or cells modified with tandem reporter constructs to identify compounds or treatments that affect a biological pathway or process. In one embodiment, the invention relates to methods of treating a disease or disorder through administration of a compound or treatment that affects a biological pathway or process associated with the disease to a subject in need thereof.

In one embodiment, the tandem reporter construct has multiple reporter genes under the control of a single promoter, such that the detectable signal is amplified in accordance with the number of reporter genes present. In one embodiment, multiple reporter genes are multiple genes encoding fluorescent proteins. In one embodiment, multiple reporter genes are 5 tandem genes encoding EGFP. In one embodiment, multiple reporter genes are 5 tandem genes encoding tdTomato.

In one embodiment, the multiple reporter genes of the tandem reporter construct are linked by protease cleavage sites. In one embodiment, a protease cleavage site is recognized by TEV protease. In one embodiment, the tandem reporter construct of the invention further contains a gene encoding a protease as part of the same polypeptide and separated from the multiple reporter genes by a cleavage site. In one embodiment, the protease further contains an internal cleavage site. Therefore, in one embodiment, a tandem reporter construct comprises a single promoter sequence linked to multiple reporter genes and a gene encoding a protease such that transcription and translation initiated from the promoter produces a single polypeptide that is then cleaved into multiple reporter proteins by the protease which also self-cleaves.

In one embodiment, the tandem reporter construct includes a sequence encoding a polypeptide of interest (POI). In one embodiment, the POI contains or is operably linked to a PEST degradation sequence.

In one embodiment, the tandem reporter construct comprises: a promoter sequence, at least one reporter sequence, a protease sequence, a POI containing or linked to a PEST degradation sequence, and multiple protease cleavage sequences for post-translational cleavage of the at least one reporter sequences, the protease sequence and the POI.

In one embodiment, the tandem reporter construct of the invention is included in an expression vector. In one embodiment, an expression vector having tandem reporter constructs of the invention are designed such that the expression of the multiple fluorescent proteins encoded by the tandem reporter construct of the invention is constitutive. Expression vectors with constitutive expression of multiple fluorescent proteins from a tandem reporter construct include, but are not limited to, AVA2515 (SEQ ID NO:2) and AVA2598 (SEQ ID NO:4). In one embodiment, an expression vector having tandem reporter constructs of the invention are designed such that the expression of the multiple fluorescent proteins encoded by the tandem reporter construct of the invention is conditional (i.e., the expression state can be altered in response to a treatment or condition.) Expression vectors with constitutive expression of multiple fluorescent proteins from a tandem reporter construct include, but are not limited to, AVA2626 (SEQ ID NO:3) and AVA2600 (SEQ ID NO:5). In one embodiment, expression of the multiple fluorescent proteins from a tandem reporter construct of AVA2626 or AVA2600 is conditionally dependent on a treatment which disrupts the nonsense mediated mRNA decay pathway being administered to the cell carrying the expression vectors.

In one embodiment, the invention relates to cells carrying at least one tandem reporter constructs of the invention. In one embodiment, the invention provides a cell carrying the tandem reporter construct from AVA2626 (SEQ ID NO:3) and the tandem reporter construct from AVA2598 (SEQ ID NO:4), such as the cell referred to in the Examples as the "Green Fireworks" cell line, wherein the tandem reporter construct from AVA2598 (SEQ ID NO:4) encodes 5 EGFP molecules and is constitutively expressed. In one embodiment, the invention provides a cell carrying the tandem reporter construct from AVA2515 (SEQ ID NO:2) and the tandem reporter construct from AVA2600 (SEQ ID NO:5), such as the cell referred to in the Examples as the "Red Fireworks" cell line, wherein the tandem reporter construct from AVA2515 (SEQ ID NO:2) encodes 5 tdTomato molecules and is constitutively expressed.

In various embodiments, the invention relates to methods of using tandem reporter constructs or cells modified with tandem reporter constructs to identify compounds or treatments that affect a biological pathway or process. In one embodiment, a biological pathway is the NMD pathway. In one embodiment, the invention relates to the use of the "Red Fireworks" and/or "Green Fireworks" cells in a method of screening for proteins that are involved in NMD. In one embodiment, the method of screening comprises contacting a cell of the invention with a library of sgRNA molecules, detecting expression of a conditional tandem reporter construct wherein expression is conditionally dependent on a treatment which disrupts NMD, and determining the protein targeted by the sgRNA molecule as involved in NMD.

In one embodiment, the invention relates to methods of a treating a disease or disorder through administration of a treatment that inhibits NMD to a subject in need thereof. In one embodiment, a subject in need thereof has been diagnosed with a disease or disorder associated with premature termination codons (PTCs). In various embodiments, the invention relates administering an inhibitor of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 or SFI1 to a subject diagnosed with a disease or disorder associated with a PTC.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein, the term "basal medium" refers to a solution of amino acids, vitamins, salts, and nutrients that is effective to support the growth of cells in culture, although normally these compounds will not support cell growth unless supplemented with additional compounds. The nutrients include a carbon source (e.g., a sugar such as glucose) that can be metabolized by the cells, as well as other compounds necessary for the cells' survival. These are compounds that the cells themselves cannot synthesize, due to the absence of at least one of the gene(s) that encode the protein(s) necessary to synthesize the compound (e.g., essential amino acids) or, with respect to compounds which the cells can synthesize, because of their particular developmental state the gene(s) encoding the necessary biosynthetic proteins are not being expressed as sufficient levels. A number of base media are known in the art of mammalian cell culture, such as Dulbecco's Modified Eagle Media (DMEM), Knockout-DMEM (KO-DMEM), and DMEM/F12, although any base medium that supports the growth of stem cells in a substantially undifferentiated state can be employed.

The terms "cells" and "population of cells" are used interchangeably and refer to a cell or a plurality of cells, i.e., more than one cell. The population of cells may be a pure population comprising one cell type. Alternatively, the population may comprise more than one cell type. In the present invention, there is no limit on the number of cell types that a cell population may comprise.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

An "effective amount" or "therapeutically effective amount" of a compound is that amount of compound which is sufficient to provide a beneficial effect to the subject to which the compound is administered.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient. The term "microarray" refers broadly to both "DNA microarrays" and "DNA chip(s)," and encompasses all art-recognized solid supports, and all art-recognized methods for affixing nucleic acid molecules thereto or for synthesis of nucleic acids thereon.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based in part on the development of a system for amplifying a detectable signal through use of a tandem reporter construct having multiple tandem genes providing a detectable signal, method of using the tandem reporter constructs in screening for the effect of treatments, and methods of treating diseases or disorders through targeting proteins involved in biological processes identified using a screen of the invention.

Compositions

In various embodiments, compositions of the invention include tandem reporter constructs, vectors carrying tandem reporter constructs, and cells modified with vectors carrying tandem reporter constructs.

Tandem Reporter Constructs

The invention is based in part on the use of proteolytic cleavage to separate tandem proteins encoded on a single transcript. In one embodiment, the invention relates to a construct wherein multiple tandem reporter genes are transcribed in a single transcript with a polypeptide/protein of interest (POI), and separated by proteolytic cleavage sites. This invention, allows the elimination of negative effects of a fused POI on maturation, localization, and half-life of a reporter by means of in vivo proteolytic separation of the reporter from the POI. This is in contrast to constructs in which the POI remains fused to the reporter, where the reporter is subject to all the regulatory constraints of the POI. In one embodiment, the invention provides a tandem reporter construct comprising a nucleic acid molecule having two or more genes encoding reporter molecules in tandem under the control of a single promoter.

In one embodiment, the tandem reporter construct contains multiple tandemly repeated reporter genes per transcription unit. In one embodiment, the tandem reporter system is a nucleic acid molecule having 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more or 20 or more tandem genes encoding reporter molecules under the control of a single promoter.

A reporter is a molecule, including polypeptide as well as polynucleotide, expression of which in a cell confers a detectable trait to the cell. In various embodiments, reporters include, but are not limited to, chloramphenicol-acetyl transferase(CAT), β-galactosyltransferase, horseradish peroxidase, luciferase, NanoLuc®, alkaline phosphatase, and fluorescent proteins including, but not limited to, green fluorescent proteins (e.g. GFP, TagGFP, T-Sapphire, Azami Green, Emerald, mWasabi, mClover3), red fluorescent proteins (e.g. tdTomato, mRFP1, JRed, HcRed1, AsRed2, AQ143, mCherry, mRuby3, mPlum), yellow fluorescent proteins (e.g. EYFP, mBanana, mCitrine, PhiYFP, TagYFP, Topaz, Venus), orange fluorescent proteins (e.g. DsRed, Tomato, Kusabria Orange, mOrange, mTangerine, TagRFP), cyan fluorescent proteins (e.g. CFP, mTFP1, Cerulean, CyPet, AmCyan1), blue fluorescent proteins (e.g. Azurite, mtagBFP2, EBFP, EBFP2, Y66H), near-infrared fluorescent proteins (e.g. iRFP670, iRFP682, iRFP702, iRFP713 and iRFP720), infrared fluorescent proteins (e.g. IFP1.4) and photoactivatable fluorescent proteins (e.g. Kaede, Eos, IrisFP, PS-CFP).

In one embodiment, a detectable trait is the generation of a detectable molecule encoded by at least one reporter genes in the tandem gene structure. In another embodiment, a detectable trait is generated by an activity of a protein encoded by at least one reporter genes in the tandem gene structure.

In one embodiment, the tandem reporter construct contains multiple tandemly repeated FP genes per transcription unit. In one embodiment, multiple tandemly repeated FPs per reporter transcription unit are useful to amplify the reporter fluorescence produced by a single cell. In one embodiment, the tandem reporter system is a nucleic acid molecule having 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more or 20 or more tandem genes encoding FPs under the control of a single promoter.

In one embodiment, all the reporter genes in the tandem gene structure encode the same reporter (e.g. all encode tdTomato or all encode GFP). In one embodiment, the reporter genes in the tandem gene structure encode two or more different reporter genes (e.g. at least one reporter gene encodes tdTomato and at least one reporter gene encodes GFP). The numbers and types of reporter genes that can be mixed are not limited and mixing of the number and types of reporter genes can provide cells carrying a tandem gene structure with a unique detection spectrum.

In one embodiment, expression of tandem reporter genes may be driven from an endogenous promoter. In such an embodiment, the tandem reporter genes may be integrated into the genome of a cell under the control of the endogenous promoter. In one embodiment, expression of tandem reporter genes may be driven from an exogenous promoter. In such an embodiment, a nucleotide sequence of the exogenous promoter may be included 5' to the at least one tandem reporter genes within a nucleic acid molecule. In certain embodiments, the promoter drives constitutive, high level expression of the tandem reporter genes. One example of such a promoter is the Elongation Growth Factor-1α (EF-1α) promoter. In other embodiments, a promoter may be inducible and drive expression only when specific conditions are met.

A promoter can be selected based on the type of host or target cell or the desired level of expression of the tandem reporter genes. One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. The promoter sequence also can be selected to provide tissue-specific transcription of the tandem reporter genes.

In one embodiment, tandem genes encoding two or more reporter molecules are separated by cleavage sites. In one embodiment, a cleavage site is a P2A site. In one embodiment, a cleavage site is a protease cleavage site. In various embodiments, a protease cleavage site may include, but is not limited to, a site targeted by a Caspase (e.g. Caspase 1 through Caspase 10), enterokinase, factor Xa, granzyme B, HRV3C protease, hydroxylamine, pancreatic elastase, pepsin A, prolyl endopeptidase, proteinase K, TEV protease, thermolysin, or thrombin. In one embodiment, a protease for cleavage of the protease cleavage sites is encoded downstream of two or more genes encoding reporter molecules as part of the same polypeptide. In one embodiment, the nucleotide sequence encoding the protease is linked to the nucleotide sequence of two or more genes encoding reporter molecules by a protease cleavage site. In one embodiment, a nucleotide sequence encoding a protease contains a sequence for an internal protease cleavage site for self-cleavage by the encoded protease.

In one embodiment, the tandem reporter construct comprises a nucleotide sequence encoding a polypeptide of interest (POI). In one embodiment, a polypeptide of interest is a protein. In one embodiment, a nucleotide sequence encoding a polypeptide of interest comprises a premature termination codon (PTC).

In one embodiment, a nucleotide sequence encoding a POI is further operably linked to nucleotide sequence encoding an amino acid sequence for rapid degradation of the encoded POI. In one embodiment, an amino acid sequence for rapid degradation of a POI is a peptide sequence rich in proline (P), glutamic acid (E), serine (S) and threonine (T), or a PEST sequence. In one embodiment, PEST-mediated degradation of a proteolytically released POI is useful to alleviate undesired negative effects of a POI on cell growth and viability.

In one embodiment, the tandem reporter construct comprises a nucleic acid molecule having a promoter sequence and two or more a reporter marker sequences separated by cleavage sites (e.g., P2A sites). In another embodiment, the tandem reporter system comprises a nucleic acid molecule having a promoter sequence, two or more a reporter marker sequences separated by cleavage sites and a sequence encoding a protease for cleavage of the cleavage sites.

Vectors

In one embodiment, the expression of the tandem reporter construct is achieved by incorporating the construct into an expression vector. The vectors to be used are suitable for replication and, optionally, integration in eukaryotic cells. Typical vectors contain transcription and translation terminators, initiation sequences, and promoters useful for regulation of the expression of the desired nucleic acid sequence.

The isolated nucleic acid of the invention can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the vector may be provided to a cell in the form of a viral vector. Viral vector technology is well known in the art and is described, for example, in Sambrook et al. (2012, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and at least one selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

For example, vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In one embodiment, the composition includes a vector derived from an adeno-associated virus (AAV). Adeno-associated viral (AAV) vectors have become powerful gene delivery tools for the treatment of various disorders. AAV vectors possess a number of features that render them ideally suited for gene therapy, including a lack of pathogenicity, minimal immunogenicity, and the ability to transduce postmitotic cells in a stable and efficient manner. Expression of a particular gene contained within an AAV vector can be specifically targeted to at least one type of cells by choosing the appropriate combination of AAV serotype, promoter, and delivery method In certain embodiments, the vector also includes conventional control elements which are operably linked to the tandem reporter construct in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA;

sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

Enhancer sequences found on a vector also regulates expression of the gene contained therein. Typically, enhancers are bound with protein factors to enhance the transcription of a gene. Enhancers may be located upstream or downstream of the gene it regulates. Enhancers may also be tissue-specific to enhance transcription in a specific cell or tissue type. In one embodiment, the vector of the present invention comprises one or more enhancers to boost transcription of the gene present within the vector.

In order to assess the expression of the tandem reporter gene construct, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as a phleomycin resistance gene, a neomycin resistance gene, a puromycin resistance gene, a blasticidin resistance gene and a hygromycin resistance gene.

Recombinase recognition sites may be included on a vector and can be used for insertion, inversion or replacement of DNA sequences, or for creating chromosomal rearrangements such as inversions, deletions and translocations. For example, two recombinase recognition sites in a vector may be in the same orientation, to allow removal or replacement of the sequence between these two recombinase recognition sites upon contact with a recombinase. In one embodiment, two recombinase recognition sites are on two different DNA molecules, allowing for recombination between the two molecules. Two recombinase recognition sites may also be incorporated in opposite orientations, to allow the sequence between these two sites to be inverted upon contact with a recombinase. Such an inversion can be used to regulate the function of an insertion cassette or a portion thereof. Therefore, changing the orientation of the construct may switch on or off the construct's effect. For example, two recombinase recognition sites may flank a selection marker sequence, allowing removal or inactivation of the selection marker sequence. Examples of suitable recombinase recognition sites include FRT sites and lox sites, which can be recognized by flp and cre recombinases, respectively.

Exemplary vectors of the invention include AVA2515 (SEQ ID NO:2); AVA2626 (SEQ ID NO:3); AVA2598 (SEQ ID NO:4), and AVA2600 (SEQ ID NO:5). The tandem reporter construct of AVA2515 and AVA2626 comprises 5 tandem tdTomato genes and a sequence encoding TEV protease under the control of the EF1α promoter. The tandem reporter construct of AVA2598 and AVA2699 comprises 5 tandem EGFP genes and a sequence encoding TEV protease under the control of the EF1α promoter.

In one embodiment, a vector of the invention is generated through FRT-based recombination of one of AVA2515 (SEQ ID NO:2); AVA2626 (SEQ ID NO:3); AVA2598 (SEQ ID NO:4), and AVA2600 (SEQ ID NO:5) with another FRT containing vector. In one embodiment, an FRT containing vector is AVA2590 (Launchpad; SEQ ID NO:1). Therefore, in one embodiment, a vector of the invention contains the backbone sequence of AVA2590 (nucleotides 1-2919 and 6568-11,503 of SEQ ID NO:1) with the nucleotide sequence of AVA2515 (SEQ ID NO:2); AVA2626 (SEQ ID NO:3); AVA2598 (SEQ ID NO:4), or AVA2600 (SEQ ID NO:5) replacing the GFP reporter (nucleotides 2920-6567 of SEQ ID NO:1) of AVA2590.

A tandem reporter construct or an expression vector of the present invention can be inserted into any type of target or host cell. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Cells

In one embodiment, target cells are prokaryotic cells. In one embodiment, target cells are eukaryotic cells. In one embodiment, a target cell is a mammalian cell, such as a murine or human cell. The target cell may be a somatic cell or a germ cell. The germ cell may be a stem cell, such as embryonic stem cells (ES cells), including murine embryonic stem cells. The target cell may be a non-dividing cell, such as a neuron, or alternatively, the target cell can proliferate in vitro under certain culturing conditions.

The target cell may be chosen from commercially available mammalian cell lines. The target cell may be a primary cell isolated from a subject. A target cell may be any type of diseased cell, including cells with abnormal phenotypes that can be identified using biological or biochemical assays. For instance, the diseased cell may be a tumor cell.

The cells of the invention and cells derived therefrom can be derived from, inter alia, humans, primates, rodents and birds. Preferably, the suitable cell is from a mammal, more preferably a primate and more preferably still, a human.

The cells useful in the methods of the present invention are cultured using methods known in the art. The cells of the present invention, whether grown in suspension or as adherent cell cultures, are grown in contact with culture media.

Culture media used in the present invention preferably comprise a basal medium, optionally supplemented with additional components.

Basal medium is a medium that supplies essential sources of carbon and/or vitamins and/or minerals for the cells. The basal medium is generally free of protein and incapable on its own of supporting self-renewal/symmetrical division of the cells.

Media formulations that support the growth of cells include, but are not limited to, Minimum Essential Medium Eagle, ADC-1, LPM (bovine serum albumin-free), F10 (HAM), F12 (HAM), DCCM1, DCCM2, RPMI 1640, BGJ Medium (with and without Fitton-Jackson Modification), Basal Medium Eagle (BME-with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E-with Earle's salt base), Medium M199 (M199H-with Hank's salt base), Minimum Essential Medium Eagle (MEM-E-with Earle's salt base), Minimum Essential Medium Eagle (MEM-H-with Hank's salt base) and Minimum Essential Medium Eagle (MEM-NAA with nonessential amino acids), and the like.

It is further recognized that additional components may be added to the culture medium. Such components include, but are not limited to, antibiotics, antimycotics, albumin, growth factors, amino acids, and other components known to the art for the culture of cells. Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 μg/ml. However, the invention should in no way be construed to be limited to any one medium for culturing the cells of the invention. Rather, any media capable of supporting the cells of the invention in tissue culture may be used.

Typical substrates for culture of the cells in all aspects of the invention are culture surfaces recognized in this field as useful for cell culture, and these include surfaces of plastics, metal, composites, though commonly a surface such as a plastic tissue culture plate, widely commercially available, is used. Such plates are often a few centimeters in diameter. For scale up, this type of plate can be used at much larger diameters and many repeat plate units used.

The culture surface may further comprise a cell adhesion protein, usually coated onto the surface. Receptors or other molecules present on the cells bind to the protein or other cell culture substrate and this promotes adhesion to the surface and promotes growth. In certain embodiments, the cultures of the invention are preferably adherent cultures, i.e. the cells are attached to a substrate.

In one embodiment, the invention relates to cells carrying a single tandem reporter construct. In one embodiment, the invention relates to cells carrying two or more tandem reporter constructs. In an exemplary embodiment, cells carrying two or more tandem reporter constructs may be useful in methods for forward genetic screening. Exemplary cell lines carrying two tandem reporter constructs are the Red Fireworks cell line and the Green Fireworks cell line.

Modulator of NMD

In one embodiment, the tandem reporter constructs of the invention are used identify genes, compounds or treatments that affect a biological pathway or process. Therefore, in one embodiment, the invention relates to modulators (e.g., an inhibitor or activator) of biological pathways. In one embodiment, a biological pathway is nonsense mediated RNA decay (NMD). In various embodiments, the present invention includes compositions for modulating the level or activity of a protein involved in NMD in a subject, a cell, a tissue, or an organ in need thereof. In various embodiments, the compositions of the invention modulates the amount of polypeptide, the amount of mRNA, the amount of activity, or a combination thereof of a gene or protein involved in NMD. In various embodiments, a protein involved in NMD is at least one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1.

One approach to the treatment of diseases or disorders resulting from premature termination codons (PTCs) is the inhibition of NMD. Therefore, in one embodiment, the invention includes compositions for treating or preventing a disease or disorder associated with a PTC. Diseases or disorders associated with PTCs include, but are not limited to, variants of Duchenne and Becker muscular dystrophies due to a PTC in dystrophin, retinoblastoma due to a PTC in RB1, neurofibromatosis due to a PTC in NF1 or NF2, ataxia-telangiectasia due to a PTC in ATM, Tay-Sachs disease due to a PTC in HEXA, cystic fibrosis due to a PTC in CFTR, Wilm's tumor due to a PTC in WT1, hemophilia A due to a PTC in factor VIII, hemophilia B due to a PTC in factor IX, p53-associated cancers due to a PTC in p53, Menkes disease, Ullrich's disease, β-Thalassemia due to a PTC in betaglobin, type 2A and type 3 von Willebrand disease due to a PTC in Willebrand factor, Robinow syndrome, brachydactyly type B (shortening of digits and metacarpals), inherited susceptibility to mycobacterial infection due to a PTC in IFNGR1, inherited retinal disease due to a PTC in CRX, inherited bleeding tendency due to a PTC in Coagulation factor X, inherited blindness due to a PTC in Rhodopsin, congenital neurosensory deafness and colonic agangliosis due to a PTC in SOX10 and inherited neural develop-mental defect including neurosensory deafness, colonic agangliosis, peripheral neuropathy and central dysmyelinating leukodystrophy due to a PTC in SOX10, and many others.

In one embodiment, an inhibitor of at least one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1 is useful in treating a disease or disorder associated with a PTC.

Inhibitors

In various embodiments, the present invention includes compositions and methods of treating diseases or disorders resulting from PTCs in a subject. In various embodiments, the composition for treating diseases or disorders resulting from PTCs comprises an inhibitor of NMD. In one embodiment, the inhibitor of the invention decreases the amount of polypeptide, the amount of mRNA, the amount of activity, or a combination thereof of at least one gene involved in the NMD pathway. In one embodiment, the inhibitor of the invention decreases the amount of polypeptide, the amount of mRNA, the amount of activity, or a combination thereof of at least one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1.

It will be understood by one skilled in the art, based upon the disclosure provided herein, that a decrease in the level of a gene involved in the NMD pathway encompasses the decrease in the expression, including transcription, translation, or both. The skilled artisan will also appreciate, once armed with the teachings of the present invention, that a decrease in the level of a gene involved in the NMD pathway includes a decrease in the activity of a protein encoded by the gene. Thus, decrease in the level or activity of a gene involved in the NMD pathway includes, but is not limited to, decreasing the amount of polypeptide encoded by the gene, and decreasing transcription, translation, or both, of a gene involved in the NMD pathway; and it also includes decreasing any activity of the encoded protein as well.

In one embodiment, the invention provides a generic concept for inhibiting NMD as a treatment for diseases or disorders associated with PTCs. In one embodiment, the composition of the invention comprises an inhibitor of at least one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1. In one embodiment, the inhibitor is selected from the group consisting of a small interfering RNA (siRNA), a microRNA, an antisense nucleic acid, a ribozyme, an expression vector encoding a transdominant negative mutant, an intracellular antibody, a peptide and a small molecule.

One skilled in the art will appreciate, based on the disclosure provided herein, that one way to decrease the mRNA and/or protein levels of at least one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1 in a cell is by reducing or inhibiting expression of the nucleic acid encoding the protein. Thus, the protein level in a cell can also be decreased using a molecule or compound that inhibits or reduces gene expression such as, for example, siRNA, an antisense molecule or a ribozyme. However, the invention should not be limited to these examples.

In one embodiment, siRNA is used to decrease the level of at least one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19): 306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, P A (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of SENP2 at the protein level using RNAi technology.

In other related aspects, the invention includes an isolated nucleic acid encoding an inhibitor, wherein an inhibitor such as an siRNA or antisense molecule, inhibits at least one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1, a derivative thereof, a regulator thereof, or a downstream effector, operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York) and as described elsewhere herein. In another aspect of the invention, at least one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1 or a regulator thereof, can be inhibited by way of inactivating and/or sequestering at least one UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1, or a regulator thereof. As such, inhibiting the effects of at least one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1 can be accomplished by using a transdominant negative mutant.

In another aspect, the invention includes a vector comprising an siRNA or antisense polynucleotide. Preferably, the siRNA or antisense polynucleotide is capable of inhibiting the expression of at least one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1. The incorporation of a desired polynucleotide into a vector and the choice of vectors is well-known in the art as described in, for example, Sambrook et al., supra.

The siRNA or antisense polynucleotide can be cloned into a number of types of vectors as described elsewhere herein. For expression of the siRNA or antisense polynucleotide, at least one module in each promoter functions to position the start site for RNA synthesis.

In order to assess the expression of the siRNA or antisense polynucleotide, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

In one embodiment of the invention, an antisense nucleic acid sequence which is expressed by a plasmid vector is used to inhibit at least one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1. The antisense expressing vector is used to transfect a mammalian cell or the mammal itself, thereby causing reduced endogenous expression of at least one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Compositions and methods for the synthesis and expression of antisense nucleic acids are as described elsewhere herein.

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

In one embodiment of the invention, a ribozyme is used to inhibit at least one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1. Ribozymes useful for inhibiting the expression of a target molecule may be designed by incorporating target sequences into the basic ribozyme structure which are complementary, for example, to the mRNA sequence of a gene involved in NMD of the present invention. Ribozymes targeting at least one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1 may be synthesized using commercially available reagents (Applied Biosystems, Inc., Foster City, Calif.) or they may be genetically expressed from DNA encoding them.

When the inhibitor of the invention is a small molecule, a small molecule antagonist may be obtained using standard methods known to the skilled artisan. Such methods include chemical organic synthesis or biological means. Biological means include purification from a biological source, recombinant synthesis and in vitro translation systems, using methods well known in the art.

Combinatorial libraries of molecularly diverse chemical compounds potentially useful in treating a variety of diseases or disorders are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

In another aspect of the invention, a NMD can be inhibited by way of inactivating and/or sequestering a protein involved in NMD. As such, inhibiting the effects of NMD can be accomplished by using a transdominant negative mutant. Alternatively an antibody specific for a protein involved in NMD (e.g., an antagonist to at lease one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1) may be used. In one embodiment, the antagonist is a protein and/or compound having the desirable property of interacting with a binding partner of a protein involved in NMD and thereby competing with the corresponding protein. In another embodiment, the antagonist is a protein and/or compound having the desirable property of interacting with a protein involved in NMD and thereby sequestering the protein.

As will be understood by one skilled in the art, any antibody that can recognize and bind to an antigen of interest is useful in the present invention. Methods of making and using antibodies are well known in the art. For example, polyclonal antibodies useful in the present invention are generated by immunizing rabbits according to standard immunological techniques well-known in the art (see, e.g., Harlow et al., 1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues. The chimeric proteins are produced by cloning the appropriate nucleic acids encoding the marker protein into a plasmid vector suitable for this purpose, such as but not limited to, pMAL-2 or pCMX.

However, the invention should not be construed as being limited solely to methods and compositions including these antibodies or to these portions of the antigens. Rather, the invention should be construed to include other antibodies, as that term is defined elsewhere herein, to antigens, or portions thereof. Further, the present invention should be construed to encompass antibodies, inter alia, bind to the specific antigens of interest, and they are able to bind the antigen present on Western blots, in solution in enzyme linked immunoassays, in fluorescence activated cells sorting (FACS) assays, in magnetic affinity cell sorting (MACS) assays, and in immunofluorescence microscopy of a cell transiently transfected with a nucleic acid encoding at least a portion of the antigenic protein, for example.

One skilled in the art would appreciate, based upon the disclosure provided herein, that the antibody can specifically bind with any portion of the antigen and the full-length protein can be used to generate antibodies specific therefor. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

Once armed with the sequence of a specific antigen of interest and the detailed analysis localizing the various conserved and non-conserved domains of the protein, the skilled artisan would understand, based upon the disclosure provided herein, how to obtain antibodies specific for the various portions of the antigen using methods well-known in the art or to be developed.

The skilled artisan would appreciate, based upon the disclosure provided herein, that that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., and in the references cited therein, and in Gu et al. (1997, Thrombosis and Hematocyst 77:755-759), and other methods of humanizing antibodies well-known in the art or to be developed.

The present invention also includes the use of humanized antibodies specifically reactive with epitopes of an antigen of interest. The humanized antibodies of the invention have a human framework and have one or more complementarity determining regions (CDRs) from an antibody, typically a mouse antibody, specifically reactive with an antigen of interest. When the antibody used in the invention is humanized, the antibody may be generated as described in Queen, et al. (U.S. Pat. No. 6,180,370), Wright et al., (supra) and in the references cited therein, or in Gu et al. (1997, Thrombosis and Hematocyst 77(4):755-759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as an epitope on an antigen of interest, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

The invention also includes functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application WO 93/21319 and PCT Application WO 89/09622.

Functional equivalents include polypeptides with amino acid sequences substantially the same as the amino acid sequence of the variable or hypervariable regions of the antibodies. "Substantially the same" amino acid sequence is defined herein as a sequence with at least 70%, preferably at least about 80%, more preferably at least about 90%, even more preferably at least about 95%, and most preferably at least 99% homology to another amino acid sequence (or any integer in between 70 and 99), as determined by the FASTA search method in accordance with Pearson and Lipman, 1988 Proc. Nat'l. Acad. Sci. USA 85: 2444-2448. Chimeric or other hybrid antibodies have constant regions derived substantially or exclusively from human antibody constant regions and variable regions derived substantially or exclusively from the sequence of the variable region of a monoclonal antibody from each stable hybridoma.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Functional equivalents of the antibodies of the invention further include fragments of antibodies that have the same, or substantially the same, binding characteristics to those of the whole antibody. Such fragments may contain one or both Fab fragments or the F(ab')$_2$ fragment. The antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers ($H_2L_2$) formed of two dimers associated through at least one disulfide bridge.

Pharmaceutical Compositions

The present invention includes pharmaceutical compositions comprising at least one modulator of NMD. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, intratumoral, epidural, intracerebral, intracerebroventricular, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Methods

The invention is based in part on the development of a method for genetic screening using the tandem reporter constructs of the invention and the use of the screening method to identify new therapeutic targets for a disease or disorder. In various embodiments, the invention relates to methods of using tandem reporter constructs or cells modified with tandem reporter constructs to identify compounds or treatments that affect a biological pathway or process. In one embodiment, the invention relates to methods of treating disease or disorder through administration of a compound or treatment that affects a biological pathway or process associated with the disease or disorder to a subject in need thereof.

Methods of Detecting a Reporter

Methods for detecting a reporter molecule comprise any method that determines the quantity or the presence of the molecule in a cell. Such methods are well known in the art and include but are not limited to western blots, northern blots, southern blots, ELISA, immunoprecipitation, immunofluorescence, flow cytometry, and immunocytochemistry. Methods for detecting fluorescent molecules in a cell preparation are well known in the art. Such methods include but are not limited to detection using flow cytometry with or without flow associated cell sorting (FACS) and analysis, or fluorescent microscopy imaging.

The invention should not be limited to any one method of protein or nucleic acid detection method recited herein, but rather should encompass all known or heretofor unknown methods of detection as are, or become, known in the art.

Methods of Screening

In one embodiment, the invention relates to a method of screening for the effect of a condition or treatment on a biological pathway or process. In one embodiment, the tandem reporter constructs can be used in a method for forward genetic screening.

In one exemplary embodiment, a biological pathway is the nonsense-mediated mRNA decay (NMD) pathway, and a treatment is administration of a sgRNA targeting a gene. In an exemplary embodiment, the tandem reporter construct is operably linked to a sequence comprising a premature stop codon (PTC) and the expression of the tandem reporter construct was evaluated in the presence of sgRNAs. Increased expression of the tandem reporter construct indicated that the sgRNA tested targeted a gene involved in the NMD pathway. In this exemplary embodiment, a first tandem reporter construct served as a positive control whereas expression of a second tandem reporter construct increased in response to a condition or treatment.

This exemplary embodiment, however, should not be viewed as limiting as to any of 1) the biological pathway or process that can be evaluated using a tandem reporter construct of the invention, 2) the compounds or treatments that can be tested, or 3) the direction of expression of a tandem reporter construct in response to the compounds or treatments tested (e.g., expression of a tandem reporter construct may either increase or decrease in response to a condition or treatment.)

In one embodiment, modified cells of the invention can be used to screen for drugs or compounds that regulate (e.g., activate or inhibit) a biological pathway or process. A drug or compound library may be applied to a modified cell of the invention, in which the tandem reporter construct is inserted downstream of a gene of interest and/or under control of the endogenous promoter of a gene of interest, to screen for candidates that may regulate the expression of the promoter and/or affect the expression of the gene.

In one embodiment, modified cells in which one, two or multiple genes are tagged using tandem reporter constructs of the invention may be used to screen for compounds that regulate the expression of one tagged gene but do not regulate expression of another. For example, to identify compounds that regulate the expression of a tagged gene associated with a disease phenotype but not a housekeeping gene or a closely related gene.

Methods of Screening Using Fireworks Cells

In one embodiment, the invention relates to the use of Red Fireworks cells in methods of screening for inhibitors of the NMD pathway, the method comprising contacting a population of Red Fireworks cells with an agent, measuring cell fluorescence, detecting an increase in green fluorescence as compared to a comparator control, and identifying the agent as an inhibitor of the NMD pathway based on the increase in green fluorescence. In one embodiment, a comparator control is a population of Red Fireworks cells that has not been contacted with the agent. In one embodiment, the method of detection is performed using flow cytometry.

In one embodiment, the invention relates to the use of Green Fireworks cells in a method of screening for inhibitors of the NMD pathway, the method comprising contacting a population of Green Fireworks cells with an agent, measuring cell fluorescence, detecting an increase in red fluorescence as compared to a comparator control, and identifying the agent as an inhibitor of the NMD pathway based on the increase in red fluorescence. In one embodiment, a comparator control is a population of Green Fireworks cells that has not been contacted with the agent. In one embodiment, the method of detection is performed using flow cytometry.

The NMD pathway is just one non-limiting example of a pathway that can be interrogated using the Fireworks cells of the invention. The system can be used for genetic identification of mRNA-destabilizing (or stabilizing) factors in other pathways. Firework's main significance lies in its broad applicability to screening a variety of human RNA degradation pathways. In various embodiments, the methods of the invention can be used to conduct forward genetic screening for components and regulators of pathways that modulate abundance of disease-associated human RNAs via their (i) POI sequence and/or its (ii) 5'-UTR sequence and/or (iii) 3'-UTR sequence.

Methods of sgRNA Enrichment

In one embodiment, the invention relates to methods of CRISPR-based forward genetic screening where multiple rounds of sgRNA enrichments are employed to increase the sensitivity of the screen in human cells, enabling efficient screening of sgRNA libraries. As a result, (1) orders of magnitude larger number of sgRNAs can be screened and (2) pathway-inhibiting sgRNAs can be identified with high confidence.

In one embodiment, the method comprises the steps of (1) generating or obtaining pool of lentiviruses from a sgRNA library, (2) transducing cells with the pool of lentiviruses to generate a pool of CRISPR-mutagenized cells, (3) performing cell sorting, (4) isolating genomic DNA from the sorted cells, (5) performing polymerase chain reaction (PCR)-amplification to generate an sgRNA pool and (6) generating a new sgRNA lentiviral library from the amplified sgRNA pool. In various embodiments, steps 1-6 are performed sequentially at least one, at least two, at least three, at least four, at least 5, at least 6, at least 7, at least 8, at least 9 or at least 10 times to enrich for sgRNAs.

Use of Tandem Reporter Constructs to Increase Sensitivity of CRISPR-Based Screening In one embodiment, the method of enriching for sgRNAs is used in combination with a tandem reporter construct of the invention to amplify the fluorescence signal generated in the CRISPR-mutagenized cells (step 2) and to increase the sensitivity of cell sorting (step 3).

Therefore, in one embodiment, the invention relates to methods of CRISPR-based forward genetic screening having an amplified fluorescence signal. In one embodiment, the method comprises the steps of (1) generating or obtaining pool of lentiviruses from a sgRNA library, (2) transducing Fireworks cells with the pool of lentiviruses to generate a pool of CRISPR-mutagenized Fireworks cells, (3) performing cell sorting, (4) isolating genomic DNA from the sorted CRISPR-mutagenized Fireworks cells, (5) performing polymerase chain reaction (PCR)-amplification to generate an sgRNA pool and (6) generating a new sgRNA lentiviral library from the amplified sgRNA pool. In one embodiment, the Fireworks cells are Green Fireworks cells, and the sorted cells are cells that have an increase in red fluorescence from tandem tdTomato proteins encoded on a tandem reporter construct. In one embodiment, the Fireworks cells are Red Fireworks cells, and the sorted cells are cells that have an increase in green fluorescence from tandem EGFP proteins encoded on a tandem reporter construct. In one embodiment, the method of sorting is fluorescence-activated cell sorting.

In various embodiments, steps 1-6 are performed sequentially at least one, at least two, at least three, at least four, at least 5, at least 6, at least 7, at least 8, at least 9 or at least 10 times to enrich for sgRNAs that target genes involved in the NMD pathway.

Methods of Modulating NMD

In one embodiment, the invention relates to methods of modulating a biological pathway or process through modulating a gene or protein identified by the method of screening as having an effect on the pathway. In one embodiment, the pathway is NMD. In one embodiment, the invention relates to methods of modulating proteins identified by the method of screening of the invention as having an effect on the NMD pathway include, but are not limited to UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1.

Methods of Treatment

The invention relates to methods of treating a disease or disorder comprising administering to a subject in need thereof a modulator of a gene or protein identified by the method of screening as having an effect that is beneficial to the treatment of the disease or disorder. In one embodiment, the disease or disorder is associated with a PTC and the method comprised administering an inhibitor of NMD to a subject in need thereof. In one embodiment, an inhibitor of NMD is an inhibitor of at least one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1.

One aspect of the invention provides a method of treating or preventing a disease or disorder associated with a PTC using an inhibitor of the invention. The following are non-limiting examples of diseases or disorders associated with a PTC that can be treated by the disclosed methods and compositions: Duchenne and Becker muscular dystrophies, retinoblastoma, neurofibromatosis, ataxia-telangiectasia, Tay-Sachs disease, cystic fibrosis, Wilm's tumor, hemophilia A, hemophilia B, p53-associated cancers, Menkes disease, Ullrich's disease, β-Thalassemia, type 2A and type 3 von Willebrand disease, Robinow syndrome, brachydactyly type B (shortening of digits and metacarpals), inherited susceptibility to mycobacterial infection, inherited retinal disease, inherited bleeding tendency, inherited blindness, congenital neurosensory deafness and colonic agangliosis, and many others.

The disorder or disease associated with a PTC can be treated by administration of therapeutic agent comprising an inhibitor of at least one of UPF1, SMG7, AVEN, SMG6, SMG5, YAE1D1, EIF2B4, UPF1, WDR55, UPF2, FARSB, ZNHIT6, NOP58, SMG5, SPATA5, GAR1, SLMO2, RPS8, EIF2B4 and SFI1 alone or in combination with another treatment or therapeutic agent. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

Administration of the therapeutic agent in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the subject, and whether prevention or treatment is to be achieved. Such factors can be readily determined by the clinician employing test systems which are well known to the art.

At least one suitable unit dosage form having the therapeutic agent(s) of the invention, can be administered by a variety of routes including parenteral, including by intravenous and intramuscular routes, as well as by direct injection into the subject.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore are not to be construed as limiting in any way the remainder of the disclosure.

Example 1: Fireworks: A Fluorescence Amplification System to Screen for Factors that Modulate NMD in Human Cells Lack of a sensitive FACS-compatible reporter system for forward genetic screening has impeded identification of components involved in human mRNA decay. Whereas numerous NMD reporter systems relying on mRNA detection by Northern blot, luminescence, or fluorescence are currently in use, they have difficulty in attaining the sensitivity and throughput thresholds required for genome-wide genetic screening in human cells for the following reasons. (1) Although transient transfection with NMD reporters produces sufficient fluorescence signal intensity (Gurskaya et al., Methods Enzymol 2016, 572:291-314; Pereverzev et al., Sci Rep 2015, 5:7729), the reporter's expression can vary dramatically among individual cells, impeding analyses required to identify moderate signal differences (typical for CRISPR-based screens) on a highly variable expression background. (2) Existing chromosomally-integrated human NMD reporters do not yield fluorescent signal of sufficient intensity for meaningful forward genetic screening; the only published reporters (Paillusson et al., Nucleic Acids Res 2005, 33:e54) produce such weak signals that the fluorescence of the PTC-containing reporter completely overlaps the background signal of reporter-lacking control cells. The same study acknowledged that the signal of a chromosomally-integrated PTC-containing reporter was not observable—even by FACS or confocal microscopy—unless NMD was inhibited. Because of insufficient fluorescence intensity of these reporters, there are no reports of their use. Moreover, typically, chromosomally-integrated reporters in human cells are subject to transgene silencing, which produces random cell-to-cell signal variation that degrades the quality of a genetic screen. (3) Despite high sensitivity due to enzymatic amplification, the signal of luciferase-based NMD reporters (Nickless et al., Nat Med 2014, 20:961-966) is not directly compatible with FACS sorting, requiring plate-based well-to-well robotic processing that limits the throughput to tens of thousands, as opposed to a billion mutants per day, achievable with a FACS instrument. An NMD reporter system suitable for high-throughput FACS-based screening is therefore not readily available, precluding forward genetic identification of human-specific components and modulators of the mRNA decay machinery.

Based on the above considerations, an ideal system would involve a chromosomally-integrated reporter that produces intense fluorescence signal. Fluorescence intensity is critical for a FACS-based screen because the higher the signal is over background, the more accurately it can be measured by FACS, defining sorting accuracy and eventually the quality of a genetic screen. Additionally, a well-balanced fluorescence-based NMD reporter system suitable for high-throughput screening must eliminate: (i) differential effects of the PTC(+) (PTC-containing) and PTC(−) (PTC-lacking) polypeptides (the PTC(+) peptide is always shorter) on localization, maturation, and half-life of the fused fluorescent protein and (ii) potential toxicity and mosaic-like silencing of genome-integrated transgenic reporters in stable cell lines.

To increase understanding of human-specific NMD and expand the scope of human factors amenable for therapeutic NMD inhibition, a forward genetic screening method has been developed involving in-vivo fluorescence amplification (Fireworks) that allows comprehensive screening for genes involved in NMD. As an example of successful forward genetic screening for NMD factors in human cells, the screening method has been used for identification of (i) known major NMD components (Kurosaki and Maquat, J Cell Sci 2016, 129:461-467): UPF1, UPF2, SMG5, SMG6, and SMG7; (ii) a known NMD regulator EIF2B4 (Gardner, Mol Cell Biol 2008, 28:3729-3741; Martin et al., J Biol Chem 2010, 285:31944-31953); as well as (iii) 11 candidate genes. Fluorescence amplification coupled with sequential rounds of enrichment for functional sgRNAs provides a platform for forward genetic discovery of key components and modulators of the human mRNA degradation machinery (FIG. 1). This approach is also generally applicable to screening a variety of other human cellular pathways as long as their readout can be adjusted to result in fluorescent protein expression, providing a powerful forward genetic tool for multiple fields of human biology.

The Fireworks system (FIG. 2 and FIG. 3) incorporates the following: (1) Translation of multiple (e.g. 10 or 5) tandemly-repeated fluorescent proteins (FPs) into a long single polyprotein to amplify the fluorescence signal produced by a single transcription unit of a PTC-containing reporter without the need to increase the reporter copy number (FIG. 2 and FIG. 3). (2) In vivo proteolytic release of the multiple FPs from the polyprotein by TEV protease, expressed as part of the same polyprotein, to eliminate negative effects of the PTC-containing polypeptide (e.g. β-globin) on FP maturation and localization. (3) Multiple features to limit reporter silencing and toxicity, including use of reporter-flanking tDNA-based (Lee et al., Cell Mol Life Sci 2013, 70:3723-3737; Raab et al., EMBO J 2012, 31:330-350) chromatin insulators (FIG. 4), introduction of a destabilizing N-terminal serine (Bachmair et al., Science 1986, 234:179-186) into the TEV protease and the β-globin as a result of their proteolytic processing (FIG. 2 and FIG. 3), autocatalytic self-cleavage (Parks et al., Virology 1995, 210:194-201) of the TEV protease (FIG. 2 and FIG. 3), and destabilization of the β-globin via its fusion with the PEST (Rogers et al., Science 1986, 234:364-368) peptide sequence (FIG. 2 and FIG. 3).

Figures 2A, 2B, 2C, 2D:
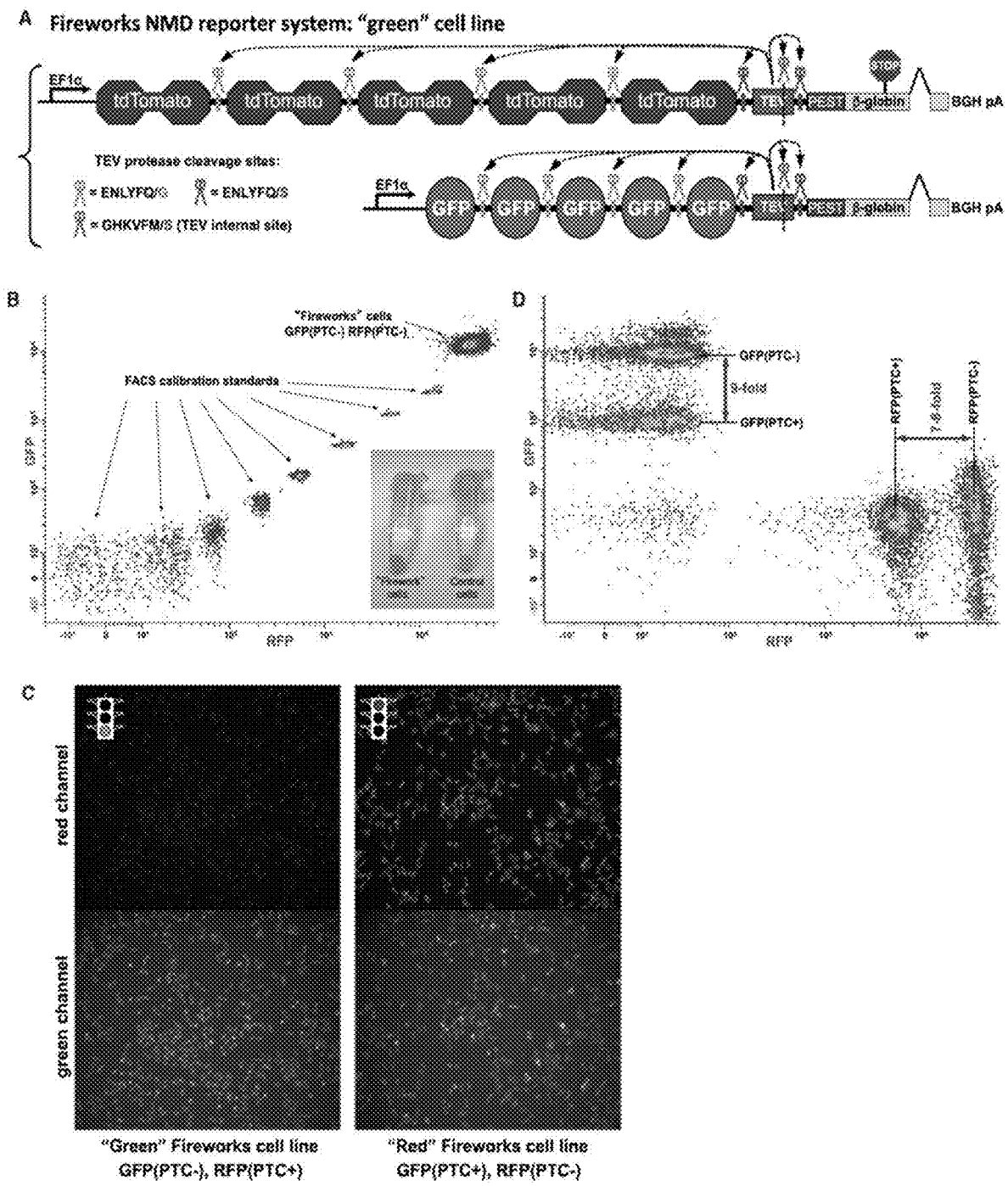
FIG. 2A through FIG. 2D, depicts the Fireworks in vivo NMD reporter system.
Figure 3A:
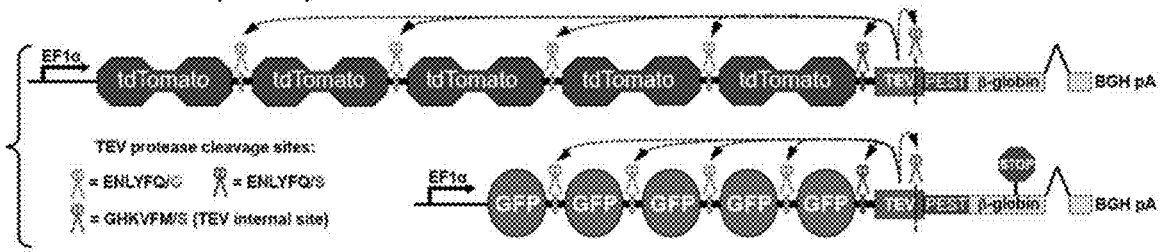
FIG. 3A depicts a schematic diagram of the orthogonal "red" Fireworks cell line. In this cell line, mRNA transcribed from the PTC-containing GFP reporter is destabilized by NMD, whereas the PTC-lacking RFP reporter serves as an expression control. Otherwise, the reporters are identical to those shown for "green" Fireworks cell line in FIG. 2A. Together, the "green" and "red" Fireworks cell lines provide controls for cell line- and fluorescent protein-specific effects.
Figure 3B:
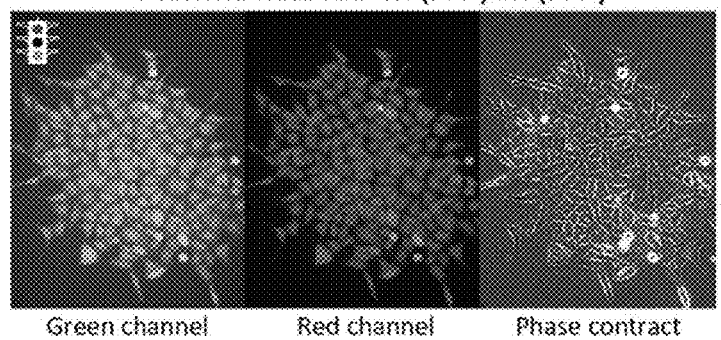
FIG. 3B demonstrates that there is little observable cell-to-cell variation in the fluorescence of Fireworks cells. Magnified view of a single colony of the HeLa Fireworks cell line in which both RFP and GFP reporters lack PTCs.
Figure 3C:
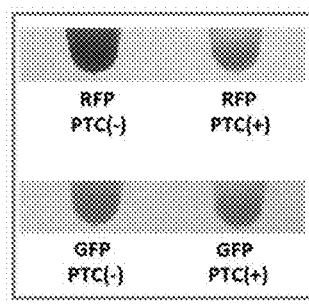
FIG. 3C depicts images of pellets of HeLa cells carrying individual genome-integrated Fireworks reporters (shown at ambient lighting) exhibit high levels of fluorescent protein expression.
Figure 3D:
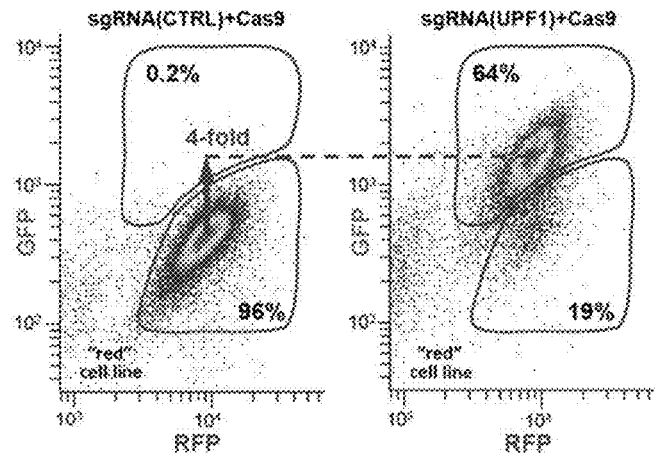
FIG. 3D depicts experimental results demonstrating that NMD inhibition via expression of Cas9 and UPF1-targeting sgRNA results in a 4-fold increase in green fluorescence of the "red" Fireworks cell line (shown in FIG. 3A and the right panel of FIG. 2C).
Figures 7A, 7B:
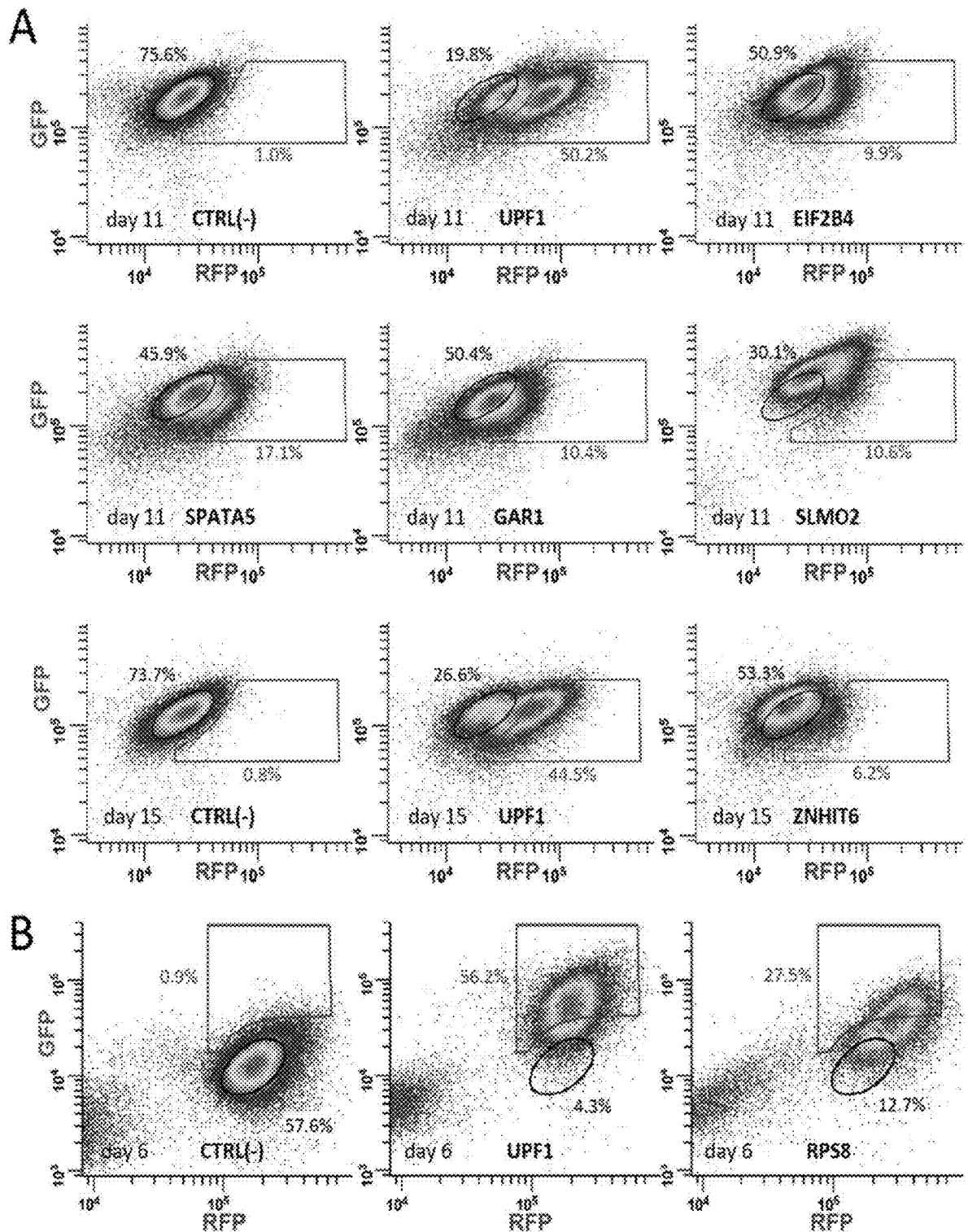
FIG. 7A and FIG. 7B, depicts FACS analysis of the fluorescence shift produced by individual sgRNAs identified by Fireworks screening of the GeCKO-LtCRISPR sgRNA library for factors affecting human NMD.

The fluorescence signal produced by HeLa cells with genome-integrated Fireworks NMD reporters is exceptionally bright, stable, and virtually immune to reporter silencing (FIGS. 1B, 1C, 2B, 2C). The signal is at least two orders of magnitude brighter than the signal of existing human chromosomally-integrated NMD reporters (Paillusson et al., Nucleic Acids Res 2005, 33:e54); it is even brighter than the brightest calibration standard of a FACS instrument (Rainbow Calibration Particles, 8 peaks, Spherotech) in both the RFP and GFP dimensions (FIG. 2B). The remarkable brightness of the Fireworks reporters underscores their potential for use not only with human β-globin reporters but also with other disease-related PTC-containing mRNAs that are naturally much less stable. Additionally, because of careful selection of the FRT (Flp-recombinase target) (Sadowski, Prog Nucleic Acid Res Mol Biol 1995, 51:53-91) sites (FIG. 7), Fireworks cell lines display low cell-to-cell signal variation (note the tight distribution in FIG. 2B) and minimal reporter silencing even after long-term propagation.

The materials and methods are now described

Generation of Fireworks Cell Lines for the Genetic Screen.

Figure 4:
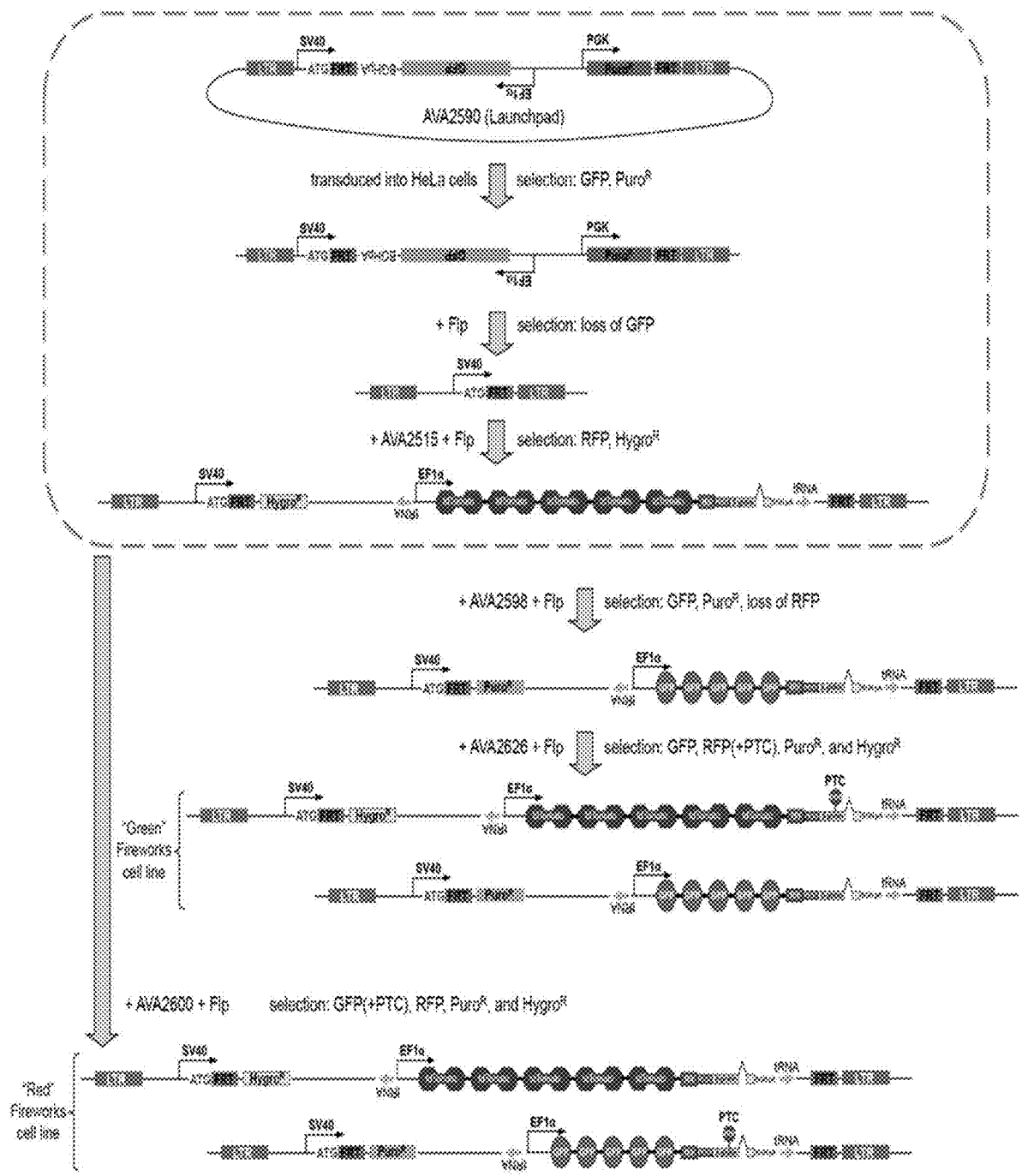
FIG. 4 depicts a schematic diagram of the construction of the orthogonal "green" and "red" HeLa Fireworks cell lines. Genomic integration of FRT sites was achieved via transduction of HeLa cells with the lentiviral vector AVA2590 (Launchpad) and the resulting pool of cells was FACS-selected for cells stably expressing Launchpad's GFP. FRT-flanked sequence of the integrated Launchpad was excised using transient transfection of Flp recombinase and the cells were FACS-selected for loss of GFP. PTC-lacking red Fireworks reporter (AVA2515) was FRT-integrated using Flp recombinase and the cells were FACS-selected for stable expression of the red Fireworks reporter. Subsequent genomic integration of the other Fireworks reporters, AVA2600 (GFP(PTC+)), AVA2598 (GFP(PTC−)), and AVA2626 (RFP(PTC+)), was achieved via Flp-mediated cassette integration/exchange and antibiotic selection, as shown; cells, concurrently expressing both green and red reporters were isolated using FACS sorting. Final "green" and "red" HeLa Fireworks cell lines were obtained by isolating individual colonies that displayed minimal, if any, silencing of integrated reporters after long-term propagation.

To obtain HeLa cell lines that minimally silence Fireworks reporters, a lentiviral FRT-flanked GFP cassette was constructed named Launchpad (AVA2590) and transduced (using lentiviral transduction) into HeLa cells to generate a pool of HeLa cells carrying 1-2 copies of this cassette at various genomic locations. Propagated populations of these cells were FACS-selected for stable GFP fluorescence. The GFP-containing FRT cassette was then removed (using transient transfection of Flp recombinase) and exchanged for the PTC-lacking Red Fireworks reporter (AVA2515) (FIG. 4). Cells were subsequently FACS-selected for stable RFP expression and subjected to Flp recombinase-mediated cassette integration/exchange, as shown in FIG. 2, resulting in "green" (RFP(PTC(+)), GFP(PTC(−))) and "red" (RFP(PTC(−)), GFP(PTC(+))) Fireworks cell lines.

Plasmid Construction.

Tandemly arranged DNA sequences of GFP and tdTomato were assembled using redundant DraIII restriction sites; the sequence of each individual FP within the repeat was verified by sequencing using DraIII sites as "bar codes" for annealing FP-specific sequencing primers. Plasmids with tandemly arranged FPs were routinely propagated in the XL1Blue strain of $E.\ Coli$; no deleterious effects of DNA recombination were observed for Fireworks reporters in this cell line. The first intron of the human β-globin gene was precisely removed using QuickChange to prevent skipping of β-globin exon 2, while the second intron was kept intact. Plasmids and plasmid sequences of the Launchpad (AVA2590) vector, PTC-lacking red (AVA2515) and green (AVA2598) Fireworks reporters, and PTC-containing red (AVA2626) and green (AVA2600).

Forward Genetic Screen for NMD Factors in Fireworks Cells.

Figures 5A, 5B, 5C, 5D:
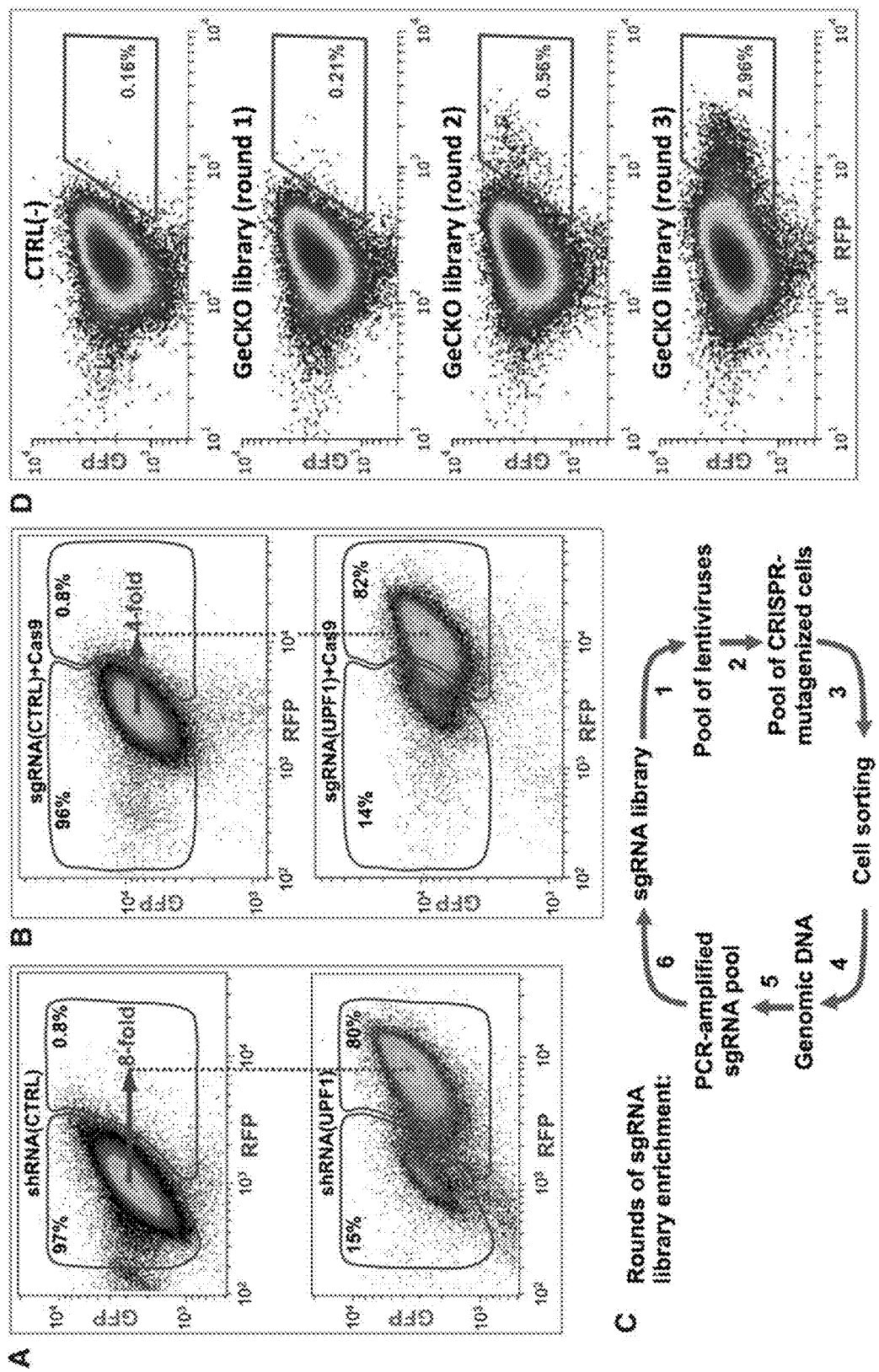
FIG. 5A through FIG. 5D, depicts experimental results demonstrating that Fireworks reporters permit rounds of efficient forward genetic screening for factors required for human NMD.

$1.8 \times 10^8$ (6×15 cm plates) "green" Fireworks cells were lentivirally transduced with the blasticidin-resistant GeCKO-LtCRISPR viral library (Shalem et al., Science 2014, 343:84-87) using 4.0 μm/ml of polybrene and propagated for 8-9 days in DMEM media supplemented with 10% FBS and 120 μm/ml hygromycin, 0.3 μg/ml puromycin and 3.0 μm/ml blasticidin. NMD-deficient cell populations ($2 \times 10^5$ cells) were isolated from $4 \times 10^8$ transduced cells using a Bio-Rad S3e cell sorter (100 μm nozzle) and their genomic DNA was phenol-extracted. sgRNAs pools were PCR-amplified using RandomF (5'-TAACTTGAAAGTAT-TTCGATTTCTTGGCTTTATATATCTTGTGGAAAGG-ACGA AACACCG-3') (SEQ ID NO: 6) and RandomR (5'-ACTTTTTCAAGTTGATAACGGACTAGCCTTATTT-TAACTTGCTATTTCTAGCTC TAAAAC-3') (SEQ ID NO: 7) primers and Gibson-cloned into the BsmBI-inearized LentiCRISPR (Shalem et al., Science 2014, 343:84-87) vector to obtain a lentiviral library (represented by $1.5 \times 10^8$ independent transformants) for the next enrichment round (FIG. 5C). Three rounds of GeCKO Lt-CRISPR library enrichment were conducted; $1.4 \times 10^8$ and $1.2 \times 10^8$ cells were sorted in the 2nd and 3rd rounds, respectively. sgRNAs obtained from the 2nd round were deep-sequenced and ranked (Table 1) according to their (i) overall abundance in the enriched sgRNA pool and (ii) enrichment over the starting sgRNA population in this round (since successful enrichment increases both of these numbers).

Sixteen of the most abundant individual sgRNAs (Table 1), whose enrichment scores in the 2nd round exceeded 10.0, were individually cloned into linearized Lt-CRISPR vector and lentivirally transduced into the "green" Fireworks cell line. Resulting cells were propagated for 11 days (or 21 days for AVEN sgRNA) and FACS-analyzed to observe an increase in red fluorescence of the PTC(+) Fireworks reporter. Indeed, the vast majority of sgRNAs reproduced the shift when tested individually. RPS8 and AVEN were targeted with shRNAs (sh22: 5'CCGGCCGTGCCCT-GAGGTTGGACGTCTCGAGACGTCCAACCTCAG-GGCACG GTTTTTTG3' (SEQ ID NO: 8) and sh01: 5'CCGGGACCTGAAATCCAAGGAAGATCTCGAG-ATCTTCCTTGGATTTCAGGT CTTTTTTG3' (SEQ ID NO: 9) for RPS8 and AVEN, respectively) cloned into the pLKO.1 vector (Moffat et al., Cell 2006, 124:1283-1298) that was used to transduce "green" and "red" Fireworks cells followed by FACS-analysis to observe effects of mRNA knockdown on fluorescence of the PTC(+) reporters.

The results of the experiments are now described

The Fireworks approach provides the ability to perform forward genetic screens for human NMD factors at the speed of a FACS sorter. As designed, orthogonal Fireworks cell lines respond as expected to the introduction of a stop codon (PTC39) (Zhang et al., RNA 1998, 4:801-815) into the β-globin sequence by a 7- to 9-fold reduction in the reporter's fluorescence (FIGS. 1C, 1D and 2C). PTC39, which is upstream of the last intron in the β-globin pre-mRNA, induces NMD of the Fireworks reporter mRNA. This, in turn, decreases the steady-state levels of all proteins (including FPs) produced from the Fireworks reporter. Each of the two orthogonal cell lines shown in FIG. 2A and FIG. 3A (termed "green" and "red" cells, respectively) carries two genome-integrated Fireworks reporters. The "green" Fireworks cell line contains stably integrated PTC-containing RFP and PTC-lacking GFP reporters (FIGS. 1A and 1C, left panel). The PTC-containing RFP reporter allows rapid screening for PTC-dependent effects by FACS-isolating cells with increased RFP fluorescence; the fluorescence signal of the PTC-lacking GFP reporter serves as a same-cell control for variations in gene expression. This arrangement enables enrichment of NMD-defective cells at a rate approaching 50,000,000 cells/hour. In the "red" (FIG. 3A and FIG. 2C, right panel) Fireworks cell line, mRNAs transcribed from the PTC-containing GFP reporter are destabilized by NMD, whereas the PTC-lacking RFP reporter serves as an expression control. These two orthogonal cell lines enable enrichment, discovery, and preliminary validation of candidate genes at a high rate, providing (i) a powerful platform to screen libraries of mutant cells for NMD defects and (ii) sound controls for cell line- and fluorescent protein-specific effects.

The fluorescence of the Fireworks cell lines increases with NMD inhibition, enabling FACS-based genetic screening for NMD factors in human cells. Each of the following modes of NMD inhibition results in 4- to 8-fold increase in fluorescence of the Fireworks cell lines: (1) inhibition via transient expression of a dominant-negative UPF1 mutant (versus UPF1(WT)) increases fluorescence 4-fold (not shown); (2) inhibition via lentiviral expression of a UPF1-targeting shRNA (versus shRNA(CTRL)) increases fluorescence 8-fold (FIG. 5A); (3) inhibition via simultaneous lentiviral expression of wild-type Cas9 and an sgRNA targeting UPF1 (versus scrambled sgRNA) increases fluorescence 4-fold (FIG. 5B). As expected, NMD inhibition increases fluorescence of only the PTC(+), not the PTC(-), reporter in each of the orthogonal Fireworks cell lines (FIGS. 5A, 5B, and 3D), ruling out non-specific effects. These predicted responses to NMD inhibition demonstrate that the Fireworks system can be applied to various methods of human genome interrogation, including (1) transposon-mediated dominant-negative (Landrette et al., PLoS One 2011, 6:e26650), (2) shRNA pLKO.1 knockdown library-based (Moffat et al., Cell 2006, 124:1283-1298), and (3) GeCKO-lentiCRISPR knockout library-based (Shalem et al., Science 2014, 343:84-87) approaches.

CRISPR-Based Forward Genetic Screening for Human NMD Factors Using Fireworks.

The Fireworks system was tested with the CRIPR-based knockout screening using the lentiviral GeCKO-lentiCRISPR sgRNA library (Shalem et al., Science 2014, 343:84-87), which contains 64,751 sgRNAs targeting 18,080 human genes. Ease of amplification of chromosomally-integrated sgRNAs by PCR allows multiple rounds of sgRNA library enrichment (FIG. 5C) as sgRNAs are iteratively re-transduced into the original Fireworks cell line after the each round of FACS selection in a SELEX-like (Tuerk and Gold, Science 1990, 249:505-510) manner. Fireworks-driven FACS throughput permits completion of one FACS cycle of genome-wide GeCKO library screening with nearly 800-fold library coverage in less than one hour. In the experiments conducted, leakage of negative control cells into the positive control cell population was below 1% (FIGS. 5A, 5B and 3D), demonstrating outstanding prospects for an unbiased genome-wide forward genetic screen. Importantly, sgRNA-specific effects are amplified, whereas cell-specific fluorescence noise is completely reset at the beginning of each sgRNA enrichment round (FIG. 5C), effectively eliminating false-positives arising from spontaneous and lentiviral insertion-induced (and therefore sgRNA-independent) mutations affecting reporters or the NMD pathway. An increase in the population of cells with a defect in NMD becomes evident during FACS rounds 2 and 3 of sgRNA library enrichment, as shown in FIG. 5D for the GeCKO-lentiCRISPR (Shalem et al., Science 2014, 343:84-87) library in the "green" Fireworks cell line. Here, sorting gates were chosen so as to collect no more than 0.16% of the negative cell population.

CRISPR-Based Forward Genetic Screening in Fireworks Cells Identifies sgRNAs Targeting a Number of Known NMD Components and Regulators, as Well as Candidate Genes with Possible Roles in Human NMD.

The pool of sgRNAs isolated from round 2 (FIG. 5C, 5D) of NMD-deficient population enrichment was deep sequenced to determine (i) the overall abundance of each sgRNA in the enriched pool and (ii) the enrichment factor for each surviving sgRNA over the starting sgRNA pool at this round. Here, the sgRNA enrichment factor serves as a measure of the increased fluorescence of the PTC(+) Fireworks reporter achieved by that sgRNA. The top 24 most abundant sgRNAs (of 64,751 sgRNAs originally present in the GeCKO library), which attained enrichment scores higher than 10, are listed in Table 1 along with their intended (Shalem et al., Science 2014, 343:84-87) gene targets.

TABLE 1

| SEQ ID NO: | sgRNA | sgRNA abundance (%)[1] | sgRNA enrichment (2nd round)[2] | Targeted gene |
|---|---|---|---|---|
| 10 | TGATTACGTCCTCCACCTCG* | 1.081 | 47.0 | UPF1 |
| 11 | AGGTCCACTCACCATTGGAG | 0.888 | 113.9 | SMG7 |
| 12 | AGTGTCCTCCTTAGCTCTGC* | 0.872 | 118.7 | SMG7 |
| 13 | AGTGTCCTCCTTAGCTCTGC* | 0.440 | 33.8 | AVEN |
| 14 | GTTCTCTGATAATCAGAATG* | 0.439 | 14.7 | SMG6 |
| 15 | ACGCACCTGGTTGCTGGTAT* | 0.265 | 54.7 | SMG5 |
| 16 | GGATGACCAAGACGACATCA | 0.262 | 18.3 | SMG6 |
| 17 | CTATGAGGGGTCAGTGACA | 0.232 | 18.3 | SMG5 |
| 18 | TGAGCACATACTCTTCACAC* | 0.180 | 102.2 | YAE1D1 |
| 19 | CCGTGACATCACAGACCCGT* | 0.176 | 21.2 | EIF2B4 |
| 20 | CGCATTGAAAACGTTTGCCG* | 0.153 | 18.4 | UPF1 |
| 21 | GGTACCTTCACTGGAGCCAC* | 0.132 | 16.1 | WDR55 |
| 22 | TATGTCTTACCAGAAGCTGC | 0.132 | 23.3 | UPF2 |
| 23 | CTCAACCGATTCCTTAGACG | 0.125 | 19.5 | SMG6 |
| 24 | TCACGCTTCACGCTGACAGT* | 0.083 | 80.0 | FARSB |
| 25 | TGCTTTGTGTTTCTTTACAC* | 0.083 | 17.0 | ZNHIT6 |
| 26 | TTAGCATCAGCTACTGCCAG* | 0.076 | 14.2 | NOP58 |
| 27 | GAAAGACTGAGGAGCTGCTG | 0.062 | 38.0 | SMG5 |
| 28 | TTCAAACTAGTAAGCAACAC* | 0.054 | 18.4 | SPATA5 |
| 29 | TAAGTTGTCAGAAAACATGA* | 0.054 | 17.1 | GAR1 |
| 30 | TCACATCGGCAGCCACCCGT* | 0.043 | 30.7 | SLMO2 |
| 31 | GCGCCCAGCTGCCAACACCA* | 0.036 | 53.9 | RPS8 |
| 32 | AGCCCATAATGTACCAGTGC | 0.033 | 14.4 | EIF2B4 |
| 33 | TACCTATGTGCGTCAGCAGC | 0.023 | 49.5 | SFI1 |

Bold type denotes known NMD factor or regulator. sgRNAs marked with asterisks (*) were tested individually in the "green" Fireworks cell line as shown in FIGS. 5 and 6. [1]sgRNA abundance is the number of deep sequencing reads obtained for an sgRNA in the enriched (blue gates in FIG. 5D) cell population divided by the total number of all reads for all sgRNAs in that population and multiplied by 100. [2]sgRNA enrichment is the number of deep sequencing reads obtained for an sgRNA in the enriched cell population divided by the number of deep sequencing reads obtained for this sgRNA in total cells at the beginning of the 2nd (FIG. 5D) enrichment round.

Of these top 24 highly-enriched sgRNAs, 13 target well-established NMD factors (Kurosaki and Maquat, J Cell Sci 2016, 129:461-467): UPF1 (2 out of 4 sgRNAs present in the library (Table 1, SEQ ID NO:10 and SEQ ID NO:20)), SMG7 (2 out of 4 sgRNAs (SEQ ID NO:11 and SEQ ID NO:12)), SMG6 (3 out of 4 sgRNAs SEQ ID NO:14, SEQ ID NO:16, and SEQ ID NO:23)), SMG5 (3 out of 6 sgRNAs (SEQ ID NO:15, SEQ ID NO:17, and SEQ ID NO:27)), UPF2 (1 out of 4 sgRNAs (SEQ ID NO:22)), and a known human NMD regulator EIF2B4 (Gardner, Mol Cell Biol 2008, 28:3729-3741; Martin et al., J Biol Chem 2010, 285:31944-31953) (2 out of 5 sgRNAs SEQ ID NO:19 and SEQ ID NO:32)) (Table 1). Therefore, the Fireworks system allowed successful identification of NMD factors and regulators in a forward genetic screen performed directly in human cells. Additionally, Table 1 contains 11 highly enriched sgRNAs targeting the following genes: AVEN, YAE1D1, WDR55, FARSB, ZNHIT6, NOP58, SPATA5, GAR1, SLMO2, RPS8, and SFI1. Without being bound by a particular theory, it is hypothesized that these genes are involved in NMD.

Figures 6A, 6B:
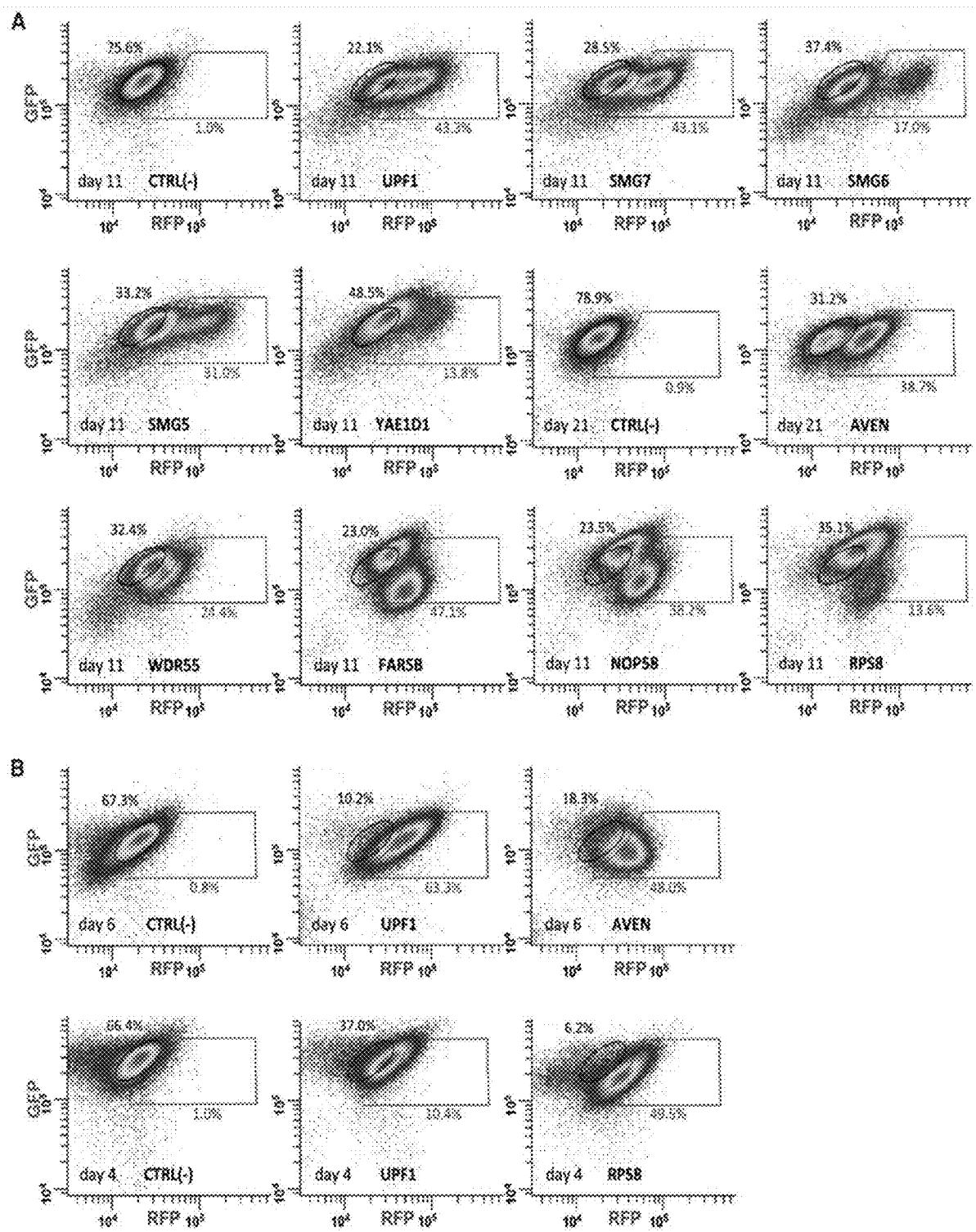
FIG. 6A and FIG. 6B, depicts FACS analysis of the fluorescence shift produced by individual sgRNAs identified by Fireworks screening of the GeCKO-LtCRISPR sgRNA library for factors affecting human NMD.

The results of the genome-wide screen were reproduced by individually transducing sgRNAs targeting 15 of the genes listed in Table 1 into the "green" Fireworks cell line and FACS-analyzing the fluorescence of the resulting cells. As shown in FIGS. 5A and 6A, cell sub-populations (albeit sometimes small) with increased fluorescence of the PTC-containing RFP reporter were observed for sgRNAs targeting each of the following genes: UPF1, SMG7, AVEN, SMG6, SMG5, YAE1D1, EIF2B4, WDR55, FARSB, ZNHIT6, NOP58, SPATA5, GAR1, SLMO2, and RPS8, demonstrating the high quality of the Fireworks approach for FACS-based pooled sgRNA library enrichment. Whereas individually-tested sgRNAs produced varying degrees of increase in fluorescence of the PTC-containing RFP reporter, these sgRNAs can be broadly divided into two categories based on their effects on fluorescence of the PTC-lacking GFP control (FIGS. 5A and 6A). SgRNAs of the 1st category (like those targeting UPF1, SMG7, AVEN, SMG6, SMG5, YAE1D1, SPATA5, and ZNHIT6) shift the CRISPR-affected population of "green" Fireworks cells right and, in some cases, slightly up, reflecting increased fluorescence of the PTC-containing RFP reporter and largely unaffected fluorescence of the PTC-lacking internal GFP expression control. SgRNAs of the 2nd category (like those targeting EIF2B4, WDR55, FARSB, NOP58, GAR1, and RPS8) shift the CRISPR-affected cell population right and downward, reflecting an increase in fluorescence of the PTC-containing RFP reporter and simultaneous decrease in fluorescence of the PTC-lacking internal GFP expression control. Whereas both categories contain sgRNAs targeting well-established bona fide NMD factors or regulators, concurrent decreases in fluorescence of the PTC-lacking GFP control produced by sgRNAs of the 2nd category suggest complexity of their effects or, possibly, negative effects on general protein translation. Potential off-target effects of sgRNAs on FP fluorescence for two of the genes, AVEN and RPS8, were excluded by targeting them with shRNAs. Unlike CRISPR-Cas9 guide RNAs (sgRNAs), which produce multiple diverse mutations at the targeted locus that result in widely varying degrees of NMD inhibition in individual cells, shRNAs do not produce mutations. Instead, shRNAs affect the level of the targeted transcript in transduced cells, resulting in a uniform fluorescence shift for the entire population of shRNA-transduced cells. FACS-analyzed fluorescence of the resulting Fireworks cell lines showed (FIGS. 5B and 6B) that shRNAs correctly reproduce the predicted fluorescence increase for PTC(+) but not PTC(−) reporters, eliminating the possibility of off-target sgRNA effects for these genes.

Since the discovery of the destabilizing effect of certain β-thalassemia mutations on spliced β-globin mRNAs in the early 1980s (Maquat et al., Cell 1981, 27:543-553), the NMD pathway has been studied extensively, with more than 1,800 PubMed publications to date. However, the scope of factors comprising the human NMD pathway has not yet been determined because of the technological difficulties of performing forward genetic interrogation of mRNA degradation pathways in human cells.

The Fireworks method successfully solves the problems that have hindered forward genetic identification of human mRNA degradation factors by providing a powerful experimental system to interrogate human NMD and mechanisms of its regulation. In just two iterative in vivo SELEX-like rounds of sgRNA library enrichment (FIG. 3C, D), 5 major known human NMD components (UPF1, UPF2, SMG5, SMG6, and SMG7), a known human NMD regulator (EIF2B4), and 11 candidate genes were identified in the screen. Finding that more than half (13 out of 24) of the top-scoring sgRNAs (Table 1) in the genetic screen target known human NMD components and modulators provides excellent validation of the method. The fact that for each of the aforementioned known NMD components (except UPF2) the method identified two or more targeting sgRNAs (Table 1)—out of, on average, four sgRNAs per gene targeted by the original GeCKO-LentiCRISPR knockout library—adds additional credibility.

Since PTC recognition depends on ongoing translation, interference with protein synthesis readily suppresses NMD (Belgrader et al., Proc Natl Acad Sci U S A 1993, 90:482-486) predicting that numerous components/regulators of translation machinery might overwhelmingly dominate an NMD screen. However, this is not the case for Fireworks (Table 1) because, by design, Fireworks assesses NMD inhibition by measuring the absolute increase (FIG. 3D) in fluorescence (i.e. absolute increase in protein levels) of the PTC(+) reporter. In contrast, inhibition of protein synthesis is expected to decrease protein levels, including those of PTC(+) and PTC(−) reporters. Inhibition of protein synthesis therefore results in diminished increase in PTC(+) reporter fluorescence and lower FACS enrichment scores as compared to those resulting from inactivation of bona fide NMD factors, reducing the number of translation components in the Fireworks screen.

Since potential interference with protein synthesis is readily reflected by decrease in fluorescence of the PTC(−) Fireworks reporter, a sizeable fraction of individually validated sgRNAs does not display noticeable defects in general protein translation (FIGS. 5A and 6A). For those sgRNAs that do decrease fluorescence of the control PTC(−) reporter, complex effects are possible, including NMD impairment in addition to or as a consequence of inhibition of general protein synthesis. Indeed, some of the genes obtained in the screen are known to act in translation: NOP58 and GAR1 are components of snoRNPs of the two different classes, C/D and H/ACA, involved in rRNA modifications; RPS8 is an essential constituent of the small (40S) subunit of the human ribosome; FARSB is a regulatory subunit of the only human phenylalanyl-tRNA synthetase; and EIF2B4 is one of the five subunits of a GTP exchange factor EIF2B (Eukaryotic Initiation Factor 2B), necessary for protein synthesis and known to be involved in regulation of the human NMD (Gardner, Mol Cell Biol 2008, 28:3729-3741; Martin et al., J Biol Chem 2010, 285:31944-31953). The candidate genes, obtained in the screen, must therefore be (i) tested to determine whether the increase in fluorescence of the PTC-containing reporter produced by an sgRNAs is solely due to a PTC-dependent decrease in mRNA stability, (ii) inspected for possible primary and secondary effects on stop codon recognition, and (iii) evaluated for possible roles in translation, considering potential effects of translation inhibition on NMD. Only then should prospective mechanistic roles in the NMD pathway be considered for these genes.

Undoubtedly, the list of human NMD factors identified in this screen is far from complete. In the currently employed GeCKO-LentiCRSPR sgRNA library (Shalem et al., Science 2014, 343:84-87) certain known NMD components (for example, SMG1) are targeted by only one sgRNA, decreasing the likelihood of their identification. Additionally, since only established genes are targeted by this library, unknown, undefined human genes and genomic elements escape interrogation. One could, therefore, envisage more detailed genetic screening strategies based on larger, more comprehensive sgRNA libraries to identify additional human NMD components and regulators. Since the FACS-driven throughput of Fireworks permits screening for NMD-affecting mutations at a rate approaching 50,000,000 mutants per hour (up to a billion mutants per day), the Fireworks approach is not limited by screening rate. SgRNA libraries several orders of magnitude larger than the one employed in this study could potentially be rapidly processed. Not only do sgRNAs vary in their efficiency of producing genomic mutations, but not all successfully produced genomic mutations result in bi-allelic gene inactivation (e.g., silent mutations or analogous amino acid substitutions may only partially, if at all, affect function of a gene's product). Therefore, substantially larger libraries combined with more comprehensive screens containing higher numbers of sgRNA enrichment rounds hold significant potential for identification of novel human NMD components. Additionally, libraries can be designed to deliberately lack sgRNAs targeting known NMD factors. Screening such libraries should be more sensitive to new, previously unknown NMD components and regulators since their (presumably moderate) effects on NMD will not be masked by strong effects of knockouts of known NMD factors.

The remarkable brightness of the Fireworks reporters underscores their potential use with other disease-related PTC-containing mRNAs that are naturally much less abundant than β-globin mRNA. The system can be easily extended to genetic identification of mRNA-destabilizing factors in pathways other than NMD, such as those affecting mRNA stability via 5'- and 3'-UTR sequences. Since Fireworks-CRISPR screening does not require specialized haploid human cell lines (the current Fireworks HeLa cells are diploid/polyploid), forward genetic identification of tissue-specific mechanisms underlying mRNA stability is also possible. Though in this work the Fireworks approach was applied to screen for genes involved in human NMD, Firework's main significance lies in its broad applicability to screening a variety of other human cellular pathways whose readout can be adjusted to result in fluorescent protein expression. Adaptations of the Fireworks approach are therefore poised to provide powerful forward genetic tools for a variety of different fields of human biology.

Example 2: Shotgun

Massive mutational interrogation of the entire genome provides enormous untapped opportunities for identifying novel components of human pathways and intervention targets for a wide variety of diseases, ranging from countless human genetic disorders to cancers. To date, massive mutational interrogation of the entire genome has been possible only in model organisms and not in human due to the (i) size and diploid nature of the human genome and (ii) lack of interrogation technology capable of creating and reliably evaluating billions of individual mutants. As human pathways are not always identical to those of model organisms, mutational screening in model organisms is inherently suboptimal and fails to identify human-specific components of the pathways. There is no alternative.

The Fireworks constructs paired with a massive Shotgun approach provides an ultra-high throughput technology that enables facile mutational interrogation of the entire human genome, allowing identification of human pathway components at unprecedented genomic resolution. First, the FACS-based fluorescence amplification approach named Fireworks provides the required sensitivity and screening throughput of more than 10⁹ genomic mutants per day. Second, empowered by Fireworks' immense screening capacity (which exceeds the sizes of existing sgRNA/shRNA libraries by several orders of magnitude), a massive Shotgun approach has been developed that employs billions of randomized Shotgun sgRNAs to achieve an unmatched—more than 400-fold—increase in genome-wide interrogation density compared to the best existing (including CRISPR-based) approaches. The Shotgun technology provides a fundamental breakthrough; it allows massive mutational interrogation of human cells on a genomic scale. Massive mutational interrogation is dramatically more advantageous and informative than traditional gene knockouts and knockdowns since knockouts and knockdowns invariably perturb all functions of a gene, whereas mutational interrogation can separate a gene's distinct functions, permitting not only identification of pathway components but also pinpointing clusters of residues suitable for pathway inhibition within multi-functional (many human genes are multi-functional) and essential proteins. The Shotgun method interrogates coding, non-coding, and intergenic genomic regions, providing the most unbiased and comprehensive tool for global mutational analysis of the diploid human genome.

Example 3: Vector Sequences

Provided are nucleotide sequences related to vectors for use in the methods of the invention.

SEQ ID NO:1: AVA2590, Launchpad, Puromycin$^R$: pSV40 promoter: 2525-2863; FRT1: 2871-2919; BGHpA: 2929-3149; GFP: 3152-3872; EF1alfa promoter: 3873-5381; PGK-PuroR: 5382-6516; FRT2: 6520-6567

SEQ ID NO:2: AVA2515[RFP(PTC−), Hygromycin$^R$]: tDNA1: 1045-1141; EF1alfa promoter: 1176-2679; 5×tdTomato: 2702-9994; TEV protease: 9995-10720; PEST (degradation sequence): 10748-10882; Human beta-globin(ΔI1): 10889-12271; BGH polyA: 12293-12517; tDNA2: 12803-12899; FRT: 12910-12957; HygromycinR (lacks promoter and 1$^{st}$ Methionine): 12977-14253

SEQ ID NO:3: AVA2626[RFP(PTC+), HygromycinR]: tDNA1: 1045-1141; EF1alfa promoter: 1176-2679; 5×tdTomato: 2702-9994; TEV protease: 9995-10720; PEST (degradation sequence): 10748-10882; Human beta-globin(ΔI1): 10889-12271; PTC39: 11003-11005; BGH polyA: 12293-12517; tDNA2: 12803-12899; FRT: 12910-12957; HygromycinR (lacks promoter and 1st Methionine): 12977-14253

SEQ ID NO:4: AVA2598[GFP(PTC−), PuromycinR]: tDNA1: 1045-1141; EF1alfa promoter: 1176-2679; 5×EGFP: 2702-6439; TEV protease: 6440-7165; PEST (degradation sequence): 7193-7327; Human beta-globin (HBB): 7334-8716; BGH polyA: 8783-8962; tDNA2: 9248-9344; FRT: 9355-9402; PuromycinR (lacks promoter and 1st Methionine): 9578-10407

SEQ ID NO:5: AVA2600[GFP(PTC+) PuromycinR]: tDNA1: 1045-1141; EF1alfa promoter: 1176-2679; 5×EGFP: 2702-6439; TEV protease: 6440-7165; PEST (degradation sequence): 7193-7327; Human beta-globin (HBB): 7334-8716; PTC39: 7448-7450; BGH polyA: 8783-8962; tDNA2: 9248-9344; FRT: 9355-9402; PuromycinR (lacks promoter and 1st Methionine): 9578-10407

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A composition comprising a tandem reporter construct, wherein the tandem reporter construct comprises a single promoter operably linked to at least five tandem reporter genes for providing a detectable signal, and a nucleotide sequence encoding a protease, wherein each of the at least five tandem reporter genes are separated by protease cleavage sequences, and further wherein the nucleotide sequence encoding the protease comprises an internal protease cleavage site, and further wherein the tandem reporter construct comprises the nucleotide sequence selected from the group consisting of SEQ ID NO:2, SEQ ID NO:3, SEQ ID NO:4 and SEQ ID NO:5.

2. The composition of claim 1, wherein the at least five tandem reporter genes are selected from the group consisting of:
   a) at least 5 tandem reporter genes that each encode the same reporter gene, and
   b) at least 5 tandem reporter genes that encode at least two different reporter genes.

3. An isolated cell comprising at least one composition of claim 1.

4. An isolated cell comprising at least two expression vectors, wherein each of the at least two expression vectors comprises a tandem reporter construct, wherein the tandem reporter construct comprises a single promoter operably linked to two or more tandem reporter genes for providing a detectable signal, and a nucleotide sequence encoding a protease, wherein each of the two or more tandem reporter genes are separated by protease cleavage sequences, and further wherein the nucleotide sequence encoding the protease comprises an internal protease cleavage site, wherein the cell is selected from the group consisting of:
   a) a cell transfected with a first expression vector and a second expression vector, wherein the first expression vector comprises the nucleotide sequence as set forth in SEQ ID NO:3, and wherein the second expression vector comprises the nucleotide sequence as set forth in SEQ ID NO:4, and
   b) a cell transfected with a first expression vector and a second expression vector, wherein the first expression vector comprises the nucleotide sequence as set forth in SEQ ID NO:2, and wherein the second expression vector comprises the nucleotide sequence as set forth in SEQ ID NO:5.

5. The cell of claim 4, wherein at least one of the tandem reporter constructs is integrated into the genome of the cell.

6. A composition comprising at least one tandem reporter construct, wherein the at least one tandem reporter construct comprises a single promoter operably linked to two or more tandem reporter genes for providing a detectable signal, and a nucleotide sequence encoding a protease, wherein each of the two or more tandem reporter genes are separated by protease cleavage sequences, and further wherein the nucleotide sequence encoding the protease comprises an internal protease cleavage site, wherein the at least one tandem reporter construct comprises a nucleotide sequence selected from the group consisting of SEQ ID NO:2, SEQ ID NO:3, SEQ ID NO:4 and SEQ ID NO:5.

7. The composition of claim 6 comprising a first tandem reporter construct and a second tandem reporter construct.

8. The method of claim 7, wherein the first tandem reporter construct comprises the nucleotide sequence as set forth in SEQ ID NO:3, and wherein the second tandem reporter construct comprises the nucleotide sequence as set forth in SEQ ID NO:4.

9. The method of claim 7, wherein the first tandem reporter construct comprises the nucleotide sequence as set forth in SEQ ID NO:2, and wherein the second tandem reporter construct comprises the nucleotide sequence as set forth in SEQ ID NO:5.

* * * * *